(12) United States Patent
Nair et al.

(10) Patent No.: US 10,738,075 B2
(45) Date of Patent: Aug. 11, 2020

(54) CYTOTOXIC AGENTS THAT PREFERENTIALLY TARGET LEUKEMIA INHIBITORY FACTOR (LIF) FOR THE TREATMENT OF MALIGNANCIES AND AS NEW CONTRACEPTIVE AGENTS

(71) Applicant: Evestra, Inc., Schertz, TX (US)

(72) Inventors: Hareesh Nair, San Antonio, TX (US); Bindu Santhamma, San Antonio, TX (US); Klaus Nickisch, Berlin (DE)

(73) Assignee: Evestra, Inc., Schertz, TX (US)

( * ) Notice: Subject to any disclaimer, the term of this patent is extended or adjusted under 35 U.S.C. 154(b) by 0 days.

(21) Appl. No.: 16/038,735

(22) Filed: Jul. 18, 2018

(65) Prior Publication Data
US 2019/0153018 A1    May 23, 2019

Related U.S. Application Data

(63) Continuation of application No. 15/077,099, filed on Mar. 22, 2016, now Pat. No. 10,053,485.

(60) Provisional application No. 62/136,813, filed on Mar. 23, 2015.

(51) Int. Cl.
| | | |
|---|---|---|
| *C07J 1/00* | (2006.01) |
| *C07J 11/00* | (2006.01) |
| *C07J 31/00* | (2006.01) |
| *C07J 41/00* | (2006.01) |
| *C07J 43/00* | (2006.01) |
| *C07J 21/00* | (2006.01) |
| *C07J 51/00* | (2006.01) |
| *C07J 71/00* | (2006.01) |

(52) U.S. Cl.
CPC ............ *C07J 1/0096* (2013.01); *C07J 11/00* (2013.01); *C07J 31/006* (2013.01); *C07J 41/0083* (2013.01); *C07J 43/003* (2013.01); *C07J 21/006* (2013.01); *C07J 51/00* (2013.01); *C07J 71/001* (2013.01)

(58) Field of Classification Search
CPC ........ C07J 11/00; C07J 1/0096; C07J 21/006; C07J 31/006; C07J 41/0083; C07J 43/003; C07J 51/00
USPC ........................................................ 514/176
See application file for complete search history.

(56) References Cited

U.S. PATENT DOCUMENTS

| | | | |
|---|---|---|---|
| 4,774,236 A | 9/1988 | Cook et al. | |
| 5,426,048 A | 6/1995 | Gearing | |
| 5,573,762 A | 11/1996 | Ferrara et al. | |
| 5,654,157 A | 8/1997 | Kim | |
| 5,837,241 A | 11/1998 | Ferrara et al. | |
| 5,948,822 A | 9/1999 | Pope et al. | |
| 5,962,321 A | 10/1999 | Gough et al. | |
| 6,011,025 A | 1/2000 | Gebhard | |
| 6,156,733 A | 12/2000 | Ferrara et al. | |
| 8,784,763 B2* | 7/2014 | Luly .................. | B01J 4/002 423/301 |
| 9,194,872 B2 | 11/2015 | Chang et al. | |
| 9,745,338 B2* | 8/2017 | Nickisch ............. | C07J 41/0072 |
| 10,053,485 B2* | 8/2018 | Nair .................... | C07J 1/0096 |
| 10,273,263 B2* | 4/2019 | Nickisch ............. | C07J 41/0072 |
| 2012/0114671 A1 | 5/2012 | Suarez et al. | |
| 2015/0133376 A1 | 5/2015 | Chang et al. | |
| 2019/0153018 A1* | 5/2019 | Nair .................... | C07J 1/0096 |

FOREIGN PATENT DOCUMENTS

| | | |
|---|---|---|
| EP | 2 371 860 | 5/2011 |
| WO | 95/10298 | 4/1995 |

OTHER PUBLICATIONS

Nickisch et al. "Synthesis and biological evaluation of partially fluorinated antiprogestins and mesoprogestins" Steroids 78 (2013) 255-267.
Rao et al. "New 11B-Aryl-Subsituted Steroids Exhibit Both Progestational and Anti progestational Activity" Steroids 63 (1998) 523-530.
International Search Report and Written Opinion for PCT Application No. PCT/US2016/023582 dated Jun. 10, 2016.
Vernallis et al. "An Antagonist for the Leukemia Inhibitory Factor Receptacle Inhibits Leukemia Inhibitory Factor, Cardiotrophin-1, Ciliary Neurotrophic Factor, and Oncostatin M" The Journal of Biological Chemistry vol. 272, No. 43 pp. 26947-26952 (1997).
International Search Report and Written Opinion for PCT Application No. PCT/US19/51143 dated Jan. 27, 2020.

* cited by examiner

*Primary Examiner* — Sabiha N Qazi
(74) *Attorney, Agent, or Firm* — Kowert, Hood, Munyon, Rankin & Goetzel, P.C.; Mark R. DeLuca

(57) ABSTRACT

Described herein are new anti-cancer compounds and methods of using such compounds, acting through a new mechanism of action by simultaneous inhibition of leukemia inhibitory factor (LIF) and MDM2.

9 Claims, 10 Drawing Sheets

CYTOTOXIC AGENTS THAT PREFERENTIALLY TARGET LEUKEMIA INHIBITORY FACTOR (LIF) FOR THE TREATMENT OF MALIGNANCIES AND AS NEW CONTRACEPTIVE AGENTS

PRIORITY CLAIM

The present application is a continuation of U.S. patent application Ser. No. 15/077,099, filed Mar. 22, 2016, which claims priority to U.S. Provisional Application Ser. No. 62/136,813 entitled "NOVEL CYTOTOXIC AGENTS THAT PREFERENTIALLY TARGET LEUKEMIA INHIBITORY FACTOR (LIF) AND MDM2 FOR THE TREATMENT OF MALIGNANCIES AND AS NEW CONTRACEPTIVE AGENTS" filed Mar. 23, 2015, both of which are incorporated herein by reference in their entirety.

BACKGROUND OF THE INVENTION

1. Field of the Invention

The invention generally relates to new anti-cancer compounds, acting through a new mechanism of action by simultaneous inhibition of leukemia inhibitory factor (LIF) and MDM2.

2. Description of the Relevant Art

Cancer is a group of diseases characterized by the uncontrolled growth and spread of abnormal cells. If the spread is not controlled, it can result in death. Cancer may affect people at all ages, but risk for the more common varieties tends to increase with age. Cancer is caused by external factors, such as tobacco, infectious organisms, and an unhealthy diet, and internal factors, such as inherited genetic mutations, hormones, and immune conditions. These factors may act together or in sequence to cause cancer. Treatments include surgery, radiation, chemotherapy, hormone therapy, immune therapy, and targeted therapy (drugs that specifically interfere with cancer cell growth). According to American Cancer Society, about 1,685,210 new cancer cases are expected to be diagnosed in 2016 and about 595,690 Americans are expected to die of cancer in 2016, which translates to about 1,630 people per day (Cancer Facts and Figures, 2016).

Conventional cancer diagnosis and therapies to date have attempted to selectively detect and eliminate cancer cells that are largely fast-growing. Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Chemotherapeutic strategies often involve administration of a combination of chemotherapeutic agents in order to increase the efficacy of treatment. Despite the availability of a large variety of chemotherapeutic agents, these therapies have many drawbacks includes bone marrow depression, immunosuppression, gastrointestinal distress, etc.

Other novel therapeutic approaches seek to utilize targeted therapies with increased selectivity and efficacy in preselected patient populations. A recent molecularly targeted therapy is established by inhibiting the enzyme poly (ADP-ribose) polymerase (PARP) by small molecule inhibitors such as Olaparib on tumors that have a defect in the homologous DNA recombination due to BRCA mutations.

Cancer stem cells have been identified in a large variety of cancer types. Many different cancers including breast, prostate ling, pancreas etc. have showed the presence of stem cell populations that are resistant to conventional chemotherapies. Therapies that could target cancer stem cells could be of great therapeutic potential in hormone/chemotherapy refractory cancers.

Leukemia inhibitory factor, or LIF, is an interleukin 6 class cytokine that affects cell growth by inhibiting cell differentiation. LIF binds to the specific LIF receptor (LIFR-α) which forms a heterodimer with a specific subunit common to all members of that family of receptors, the GP130 signal transducing subunit. This leads to activation of the JAK/STAT (Janus kinase/signal transducer and activator of transcription) and MAPK (mitogen activated protein kinase) cascades. LIF promotes STAT3 phosphorylation.

LIF promotes tumorigenesis in many solid tumors and mediates pro-invasive activation of stromal fibroblasts in cancer. LIF mediates TGF beta dependent actinomycin contractility, extracellular matrix remodeling leading to cancer cell invasion in fibroblasts. It is established that paracrine molecules such as TGF-beta, growth factors, and proinflammatory molecules (such as the IL-6 family of cytokines that includes LIF) are secreted by cancer cells and promote tumorigenesis. TGF-beta-mediated phosphorylation of Smad3 potentiates transcriptional regulation of many genes that assist in the proliferation of cancer cells. The role of TGF-beta/SMAD and JAK/STAT3 in signaling in tumor cell dependent proinvasive fibroblast activation and expression of alpha-smooth muscle actin (α-SMA) producing carcinoma associated fibroblast (CAF) hallmark is well known.

Leukemia Inhibitory Factor (LIF) is, thus important in sustaining pluripotency and stemcellness and embryogenesis. A critical point during mammalian pregnancy is the implantation of the blastocyst when the embryo attaches to the wall of the uterus. Females lacking a functional LIF gene are fertile, but their blastocysts fail to implant and do not develop. LIF may also be critical to endometrial receptivity in humans, as well as a wide range of other mammals, with reduced LIF expression being linked to several cases of female infertility.

LIF induces many genes that over express in cancer. One gene LIF induces over expression for is breast cancer antiestrogen resistance protein (p13Cas/BCAR1). Overexpression of p130Cas/BCAR1 has been detected in human breast cancer, prostate cancer, ovarian cancer, lung cancer, colorectal cancer, hepatocellular carcinoma, glioma, melanoma, anaplastic large cell lymphoma and chronic myelogenous leukemia. The presence of aberrant levels of hyperphosphorylated p130Cas/BCAR1 strongly promotes cell proliferation, migration, invasion, survival, angiogenesis and drug resistance.

Carcinoma-associated fibroblasts (CAF) are the most abundant population of non-cancer cells found in tumors, and their presence is often associated with poor clinical prognosis. LIF drives cancer cell-dependent pro-invasive extracellular matrix remodeling in carcinoma associated fibroblasts. It has been established that under the influence of bioactive molecules, such as LIF, within the tumor stroma, resident fibroblast are activated and promote tumorigenesis.

LIF is an important negative regulator of tumor suppressor gene p53. Down regulation of p53 by LIF is mediated by the activation of STAT3, which transcriptionally induces inhibitor of DNA binding 1 (ID1). ID1 upregulates MDM2, a natural negative regulator of p53 and promotes p53 degradation. EC330 was found to indirectly diminish the phosphorylation of SMAD thorough blocking TGF-beta. Overexpression of LIF is associated with poor prognosis and increase incidence of chemoresistance. Targeting LIF and MDM2 to reactivate p53 is a potential therapeutic strategy for chemotherapy as well as in combination with other agents to alleviate chemoresistance.

There have been few discoveries made in the field of LIF regarding the inhibition of LIF in medicine. Monoclonal antibodies against LIF have been described. For example, U.S. Pat. No. 6,156,729 claimed the use of leukemia inhibitory factor (LIF) antagonists to prevent or lessen hypertrophy.

EP Patent Application No. EP2371860 A1 claimed that LIF specific monoclonal antibody could be useful for the treatment for proliferative diseases such as cancer.

U.S. Pat. No. 9,194,872 B2 and U.S. Published Patent Application No. 2015/0133376 A1 taught the use of a leukemia inhibitory factor receptor inhibitor for the potentiation of cancer radiotherapy. U.S. Pat. No. 9,194,872 also claimed rapamycin and substituted quinoline as cancer therapy sensitizers that modulate LIF.

A receptor protein (DNA encoding fusion receptor) comprising a gp130 polypeptide linked to a single-chain leukemia inhibitory factor receptor (LIF-R) polypeptide is capable of binding both oncostatin M and leukemia inhibitory factor (LIF) has reported in U.S. Pat. No. 5,426,048.

A method for treating a mammal experiencing heart failure to prevent or lessen cardiac hypertrophy comprising administering therapeutically effective amount of LIF antagonist (antibody) and an endothelin antagonist to a mammal in need of such treatment was described in U.S. Pat. Nos. 6,156,733, 5,573,762 and 5,837,241.

The use of recombinant LIF from mammalian species to enhance implantation and development of embryos was described in U.S. Pat. No. 5,962,321.

In summary, all prior art among the area of LIF and LIFR targeting agents only included monoclonal antibodies (mAbs) and glycosylated or non-glycosylated antibody fragments. Some of these agents are in clinical trials and none has been approved to use in patients yet. Generally mAbs are expensive to produce and recognize only specific epitope(s) on an antigen. This drawback could lead to miss some variants. Moreover limited clones are available. It is therefore desirable to develop compounds that are small molecule inhibitors of LIF/LIFR and have targeted therapeutic advantage in treating cancers.

SUMMARY OF THE INVENTION

In one embodiment, a cytotoxic compound has the structure (I) or (II):

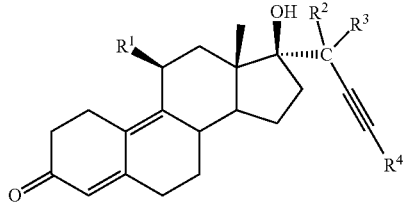

(I)

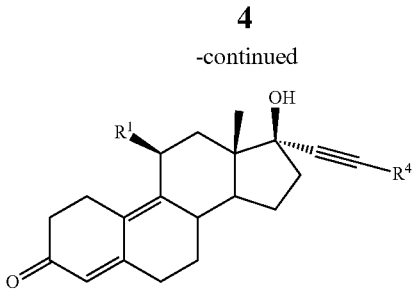

(II)

where:

$R^1$ is

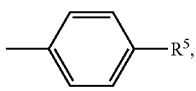

alkyl, alkenyl, or $-(CH_2)_n-X-(CH_2)_m-CH_3$;

X is O, NH, or S;

n=1-18; m=1-18;

$R^2$ is H, F, Cl, $-C(O)-R^6$, or $-CH_2(OH)$;

$R^3$ is H, F, Cl, $-C(O)-R^6$, or $-CH_2(OR^6)$;

$R^4$ is H, alkyl, $-CH_2-OH$, $-CO_2R^6$, $-CON(R^6)_2$;

$R^5$ is alkyl, alkenyl, alkylacyl, cycloalkyl, heterocycle, $-CN$, alkoxy, $-N(R^6)_2$, $-CON(R^6)_2$, $-S(O)R^6$, $-SR_6$, $-SO_2R^6$; or $-(CH_2)_p-CH_2-Y$;

Y is H, $OR^6$, $SCH_3$, $CF_3$, $-N(R^6)_2$; p=1-18; and $R^6$ is H, alkyl, or cycloalkyl.

In an embodiment, a cytotoxic compound has the structure (III):

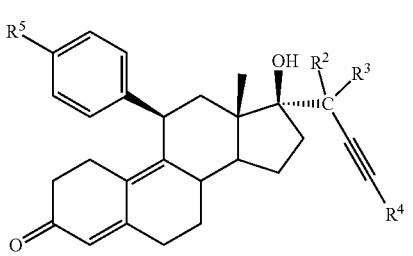

(III)

where:

$R^2$ is H, F, Cl, $-CO-$, or $-C(OH)-$;

$R^3$ is H, F, Cl, $-CO-$; or $-C(OH)-$; $R^4$ is H, alkyl, $-CH_2-OH$, $-CO_2R^6$, $-CON(R^6)_2$;

$R^5$ is alkyl, alkenyl, alkylacyl, cycloalkyl, heterocycle, $-CN$, alkoxy, $-N(R^6)_2$, $-CON(R^6)_2$, $-S(O)R^6$, $-SR_6$, $-SO_2R^6$; or $-(CH_2)_p-CH_2-Y$; and Y is H, $OR^6$, $SCH_3$, $CF_3$, $-N(R^6)_2$; p=1-18; and $R^6$ is H, alkyl, or cycloalkyl.

In an embodiment, a cytotoxic compound has the structure (IV):

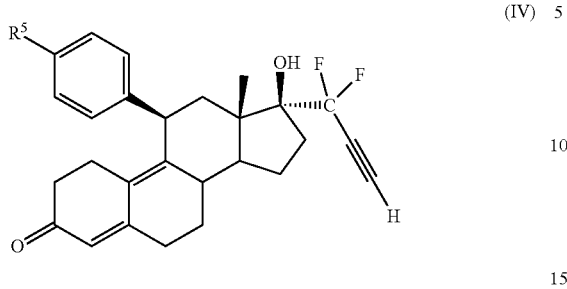

(IV)

where:
R$^5$ is alkyl, alkenyl, alkylacyl, cycloalkyl, heterocycle, —CN, alkoxy, —N(R$^6$)$_2$, —CON(R$^6$)$_2$, —S(O)R$^6$, —SR$_6$, or —SO$_2$R$^6$; and
R$^6$ is H, alkyl, or cycloalkyl.

In an embodiment, a cytotoxic compound has the structure (IV):

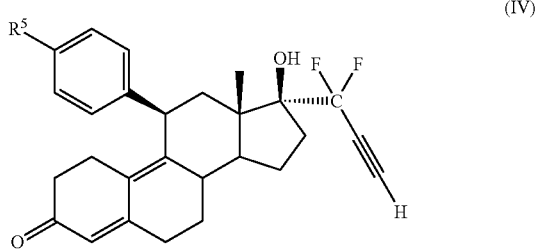

(IV)

where:
R$^5$ is alkyl, alkenyl, alkylacyl, cycloalkyl, 1,3-imidazolyl, alkoxy, —N(R$^6$)$_2$, —SR$_6$, or —SO$_2$R$^6$; and
R$^6$ is H, lower alkyl, or cycloalkyl.

In some embodiments, a cytotoxic compound has the structure (IV), where R$^5$ is alkyl, alkenyl, or cycloalkyl. In some embodiments, a cytotoxic compound has the structure (IV), where R$^5$ is 1,3-imidazolyl. In some embodiments, a cytotoxic compound has the structure (IV), where R$^5$ is alkoxy. In some embodiments, a cytotoxic compound has the structure (IV), where R$^5$ is —N(R$^6$)$_2$. In some embodiments, a cytotoxic compound has the structure (IV), where R$^5$ is —SR$_6$. In some embodiments, a cytotoxic compound has the structure (IV), where R$^5$ is —SO$_2$R$^6$.

In an embodiment, a method of treating cancer in a subject comprising administering to a subject a medicament comprising an effective amount of a cytotoxic small molecule compound that inhibits leukemia inhibitory factor or leukemia inhibitory factor receptor. The cancer may be a cancer that overexpresses leukemia inhibitory factor. The cancer may be a cancer that exhibits a desmoplastic stromal response. The cancer may be a cancer that exhibits cancer initiating stem cells (CISC) or cancer associated stem cells (CASC). The cytotoxic small molecule compound may have the structures as set forth above.

In some embodiments, in addition to inhibiting leukemia inhibitory factor or leukemia inhibitory factor receptor, the cytotoxic small molecule compound inhibits MDM2 and/or inhibits carcinoma associated fibroblast and/or stabilizes P53 levels.

In an embodiment, a synthetic intermediate useful for the formation of cytotoxic small molecule compounds has the structure (V):

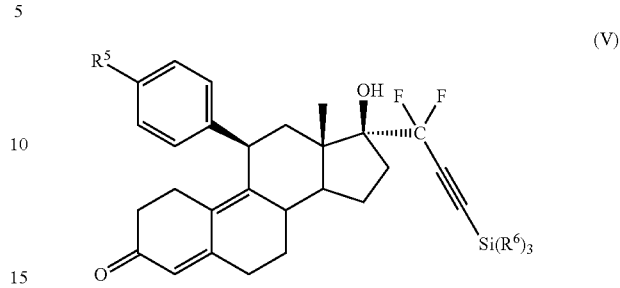

(V)

where:
R$^5$ is alkyl, alkenyl, alkylacyl, cycloalkyl, heterocycle, —CN, alkoxy, —N(R$^6$)$_2$, —CON(R$^6$)$_2$, —S(O)R$^6$, —SR$_6$, —SO$_2$R$^6$; or —(CH$_2$)$_p$—CH$_2$—Y; and
Y is H, OR$^6$, SCH$_3$, CF$_3$, —N(R$^6$)$_2$; p=1-18; and
R$^6$ is H, alkyl, or cycloalkyl.

In an embodiment, the synthetic intermediate has the structure (V) where:
R$^5$ is alkyl, alkenyl, alkylacyl, cycloalkyl, 1,3-imidazolyl, alkoxy, —N(R$^6$)$_2$, —SR$_6$, or —SO$_2$R$^6$; and
R$^6$ is H, lower alkyl, or cycloalkyl.

In an embodiment, a method of treating hypertrophic fibroblasts in a subject comprises administering to a subject a medicament comprising an effective amount of a cytotoxic small molecule compound, as described herein, that reduces the amount of hypertrophic fibroblasts in the subject.

In an embodiment, a cytotoxic small molecule compound, as described herein, as a biomarker/companion diagnostic (CDx) for selecting a suitable population to treat with LIF inhibitors by using the cytotoxic compounds to downregulate phosphorylation of STAT3.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
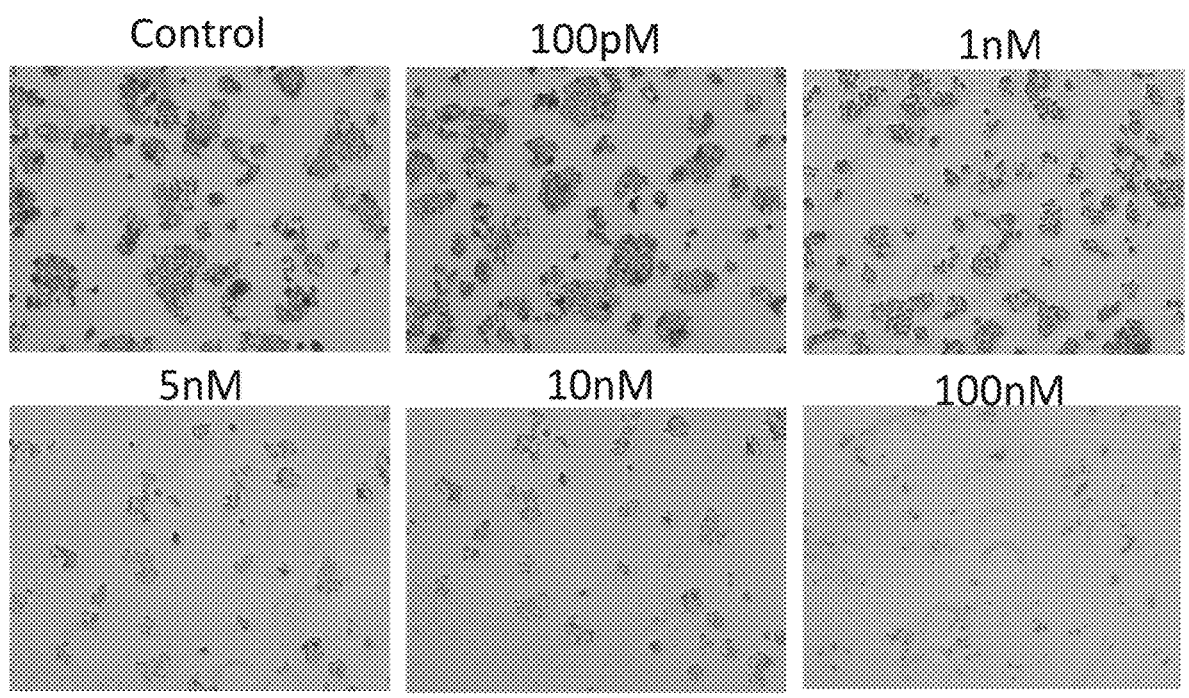
FIG. 1 depicts in vitro tumorigenicity potential of EC332 in T47D breast cancer cells

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Unless defined otherwise, all technical and scientific terms used herein have the same meaning as commonly understood by one of ordinary skill in the art.

Compounds described herein embrace both racemic and optically active compounds. Chemical structures depicted herein that do not designate specific stereochemistry are intended to embrace all possible stereochemistries.

It will be appreciated by those skilled in the art that compounds having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound. As used herein, the term "single stereoisomer" refers to a compound having one or more chiral center that, while it can exist as two or more stereoisomers, is isolated in greater than about 95% excess of one of the possible stereoisomers. As used herein a compound that has one or more chiral centers is considered to be "optically active" when isolated or used as a single stereoisomer.

The term "alkyl" as used herein generally refers to a radical substituent containing the monovalent group $C_nH_{2n}$, where n is an integer greater than zero. In some embodiments n is 1 to 12. The term "alkyl" includes a branched or unbranched monovalent hydrocarbon radical. Examples of alkyl radicals include, but are not limited to: methyl, ethyl, propyl, isopropyl, butyl, iso-butyl, sec-butyl, pentyl, 3-pentyl, hexyl, heptyl, octyl, nonyl, decyl, undecyl, dodecyl. When the alkyl group has from 1-6 carbon atoms, it is referred to as a "lower alkyl." Suitable lower alkyl radicals include, but are not limited to, methyl, ethyl, n-propyl, i-propyl, 2-propenyl (or allyl), n-butyl, t-butyl, and i-butyl (or 2-methylpropyl).

The term "cycloalkyl" as used herein generally refers to a radical substituent containing the monovalent group $C_nH_{2n-1}$, where n is an integer greater than zero and wherein the carbons $C_1$ and $C_n$ are coupled to each other to form a ring. In some embodiments n is 3 to 8. Examples of cycloalkyl radicals include, but are not limited to: cyclopropyl (n=3), cyclobutyl (n=4), cyclopentyl (n=5), cyclohexyl (n=6), cycloheptyl (n=7), and cyclooctyl (n=8).

The term "alkoxy" generally refers to an —OR group, where R is a lower alkyl, substituted lower alkyl, aryl, substituted aryl, aralkyl or substituted aralkyl. Suitable alkoxy radicals include, but are not limited to, methoxy, ethoxy, phenoxy, t-butoxy, methoxyethoxy, and methoxymethoxy.

The term "alkylacyl" denotes groups —C(O)R where R is alkyl as defined herein.

The term "cycloalkylacyl" denotes groups —C(O)R where R is a cycloalkyl. Examples of cycloalkylacyl compounds include, but are not limited to, cyclopropylacyl-, cyclopentylacyl and cyclohexylacyl.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogs of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom that results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

As used herein the terms "alkenyl" and "olefin" generally refer to any structure or moiety having the unsaturation C=C. Examples of alkenyl radicals include, but are not limited to vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

Cytotoxic Agents

Described herein are novel cytotoxic agent, which may be used in the treatment of cancer by acting through a new mechanism of action by simultaneous inhibition of leukemia inhibitory factor (LIF) and MDM2. One significant advantage of the described compounds is that they act directly on the tumor cells/tumor stem cells and on the surrounding stromal fibroblasts (tumors with desmoplastic stroma or hypertrophic cell mass) as well.

In one embodiment, a cytotoxic agent has the structure (I) or (II):

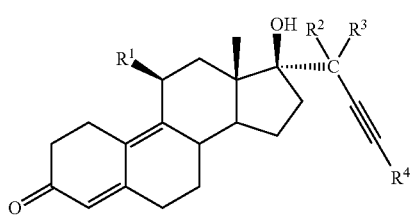

(I)

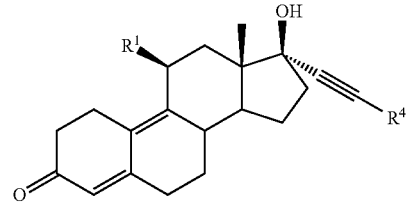

(II)

where:

$R^1$ is

alkyl, alkenyl, or —$(CH_2)_n$—X—$(CH_2)_m$—$CH_3$;

X is O, NH, or S;

n=1-18; m=1-18;

$R^2$ is H, F, Cl, —C(O)—$R^6$, or —$CH_2$(OH);

$R^3$ is H, F, Cl, —C(O)—$R^6$, or —$CH_2(OR^6)$;

$R^4$ is H, alkyl, —$CH_2$—OH, —$CO_2R^6$, —$CON(R^6)_2$;

$R^5$ is alkyl, alkenyl, alkylacyl, cycloalkyl, heterocycle, —CN, alkoxy, —$N(R^6)_2$, —$CON(R^6)_2$, —$S(O)R^6$, —$SR_6$, —$SO_2R^6$; or —$(CH_2)_p$—$CH_2$—Y;

Y is H, $OR^6$, $SCH_3$, $CF_3$, —$N(R^6)_2$; p=1-18; and $R^6$ is H, alkyl, or cycloalkyl.

In one embodiment, a cytotoxic agent has the structure (III):

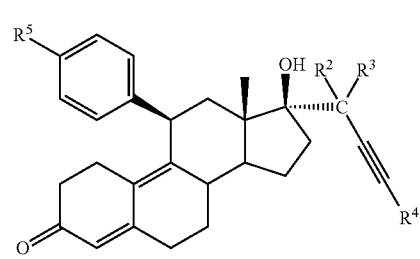

(III)

Where:

$R^2$ is H, F, Cl, —CO—, or —C(OH)—;

$R^3$ is H, F, Cl, —CO—; or —C(OH)—;

$R^4$ is H, alkyl, —$CH_2$—OH, —$CO_2R^6$, —$CON(R^6)_2$;

$R^5$ is alkyl, alkenyl, alkylacyl, cycloalkyl, heterocycle, —CN, alkoxy, —$N(R^6)_2$, —$CON(R^6)_2$, —$S(O)R^6$, —$SR_6$, —$SO_2R^6$; or —$(CH_2)_p$—$CH_2$—Y; and Y is H, $OR^6$, $SCH_3$, $CF_3$, —$N(R^6)_2$; p=1-18; and $R^6$ is H, alkyl, or cycloalkyl.

In one embodiment, a cytotoxic agent has the structure (IV):

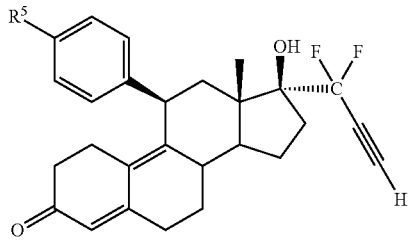

(IV)

Where:
$R^5$ is alkyl, alkenyl, alkylacyl, cycloalkyl, heterocycle, —CN, alkoxy, —N($R^6$)$_2$, —CON($R^6$)$_2$, —S(O)$R^6$, —S$R_6$, or —SO$_2R^6$; and
$R^6$ is H, alkyl, or cycloalkyl.

In a specific embodiment, a cytotoxic agent has the structure (IV):

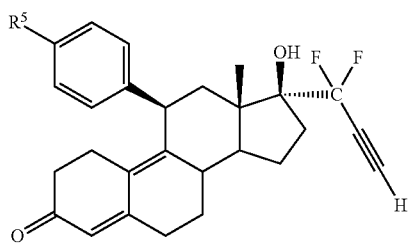

(IV)

Where:
$R^5$ is alkyl, alkenyl, alkylacyl, cycloalkyl, 1,3-imidazolyl, alkoxy, —N($R^6$)$_2$, —S$R_6$, or —SO$_2R^6$; and
$R^6$ is H, lower alkyl, or cycloalkyl.

In a specific embodiment, a cytotoxic agent has the structure (IV), where $R^5$ is alkyl, alkenyl, or cycloalkyl. In a specific embodiment, a cytotoxic agent has the structure (IV), where $R^5$ is 1,3-imidazolyl. In a specific embodiment, a cytotoxic agent has the structure (IV), where $R^5$ is alkoxy. In a specific embodiment, a cytotoxic agent has the structure (IV), where $R^5$ is —N($R^6$)$_2$. In a specific embodiment, a cytotoxic agent has the structure (IV), where $R^5$ is —S$R_6$. In a specific embodiment, a cytotoxic agent has the structure (IV), where $R^5$ is —SO$_2R^6$. For each of these embodiments, where appropriate, $R^6$ is H, lower alkyl, or cycloalkyl.

Specific examples of cytotoxic agents include:

EC330

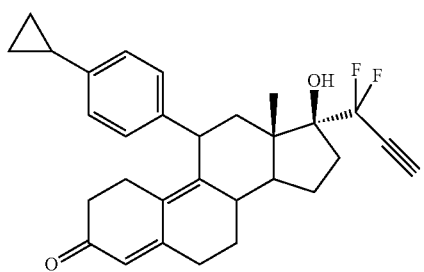

EC332

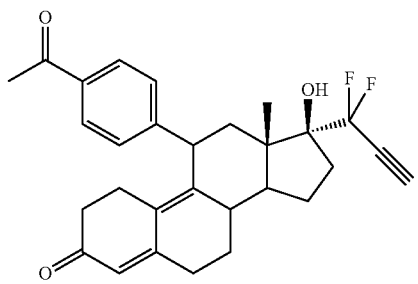

EC351

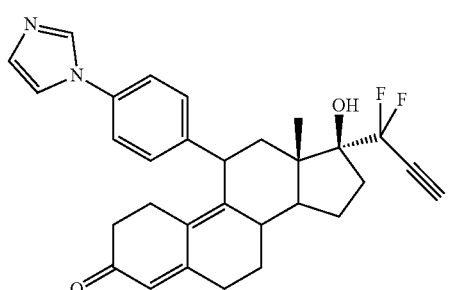

EC352

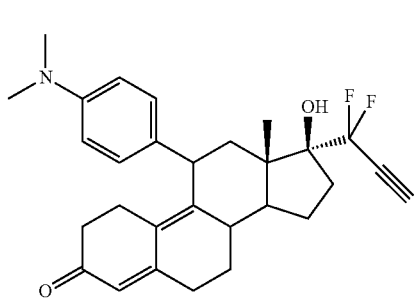

EC356

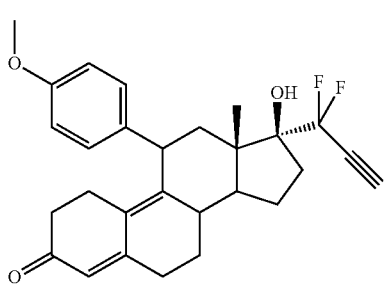

EC357

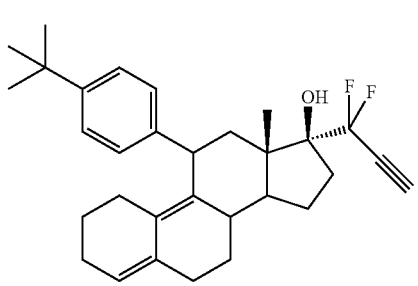

EC358
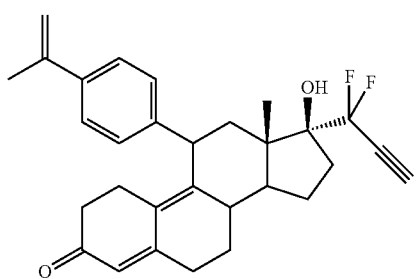
EC359
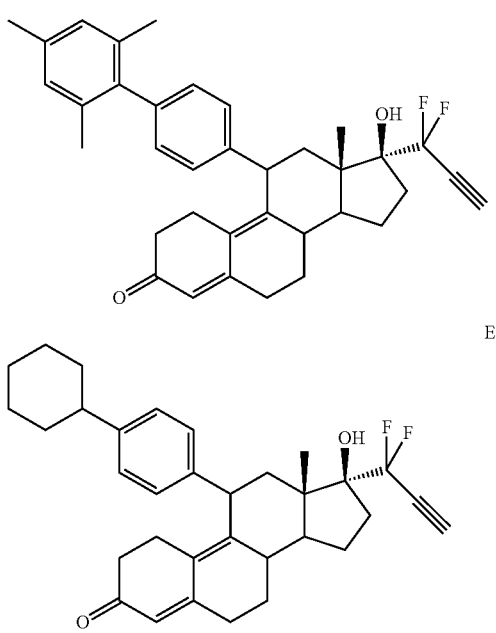
EC360
EC361
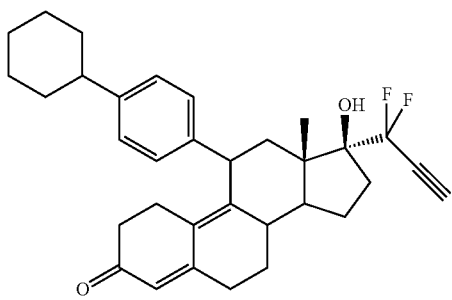
EC362
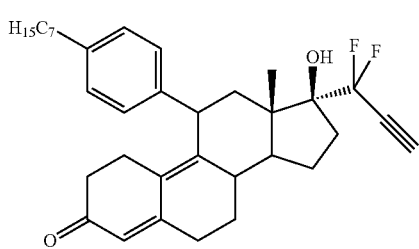
EC363
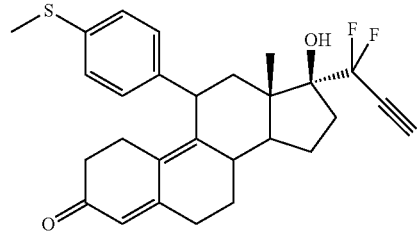
Synthesis of Cytotoxic Agents
Compounds having general formula (I) may be synthesized as outlined in the following general scheme (Scheme 1).
Scheme 1.
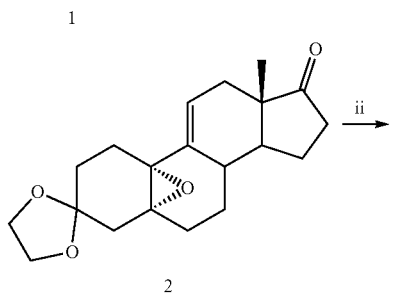
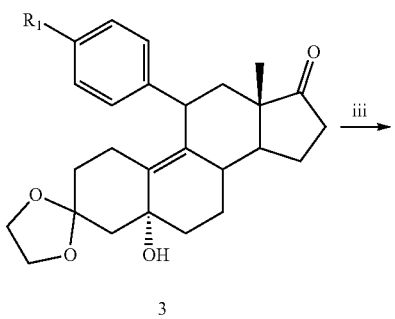
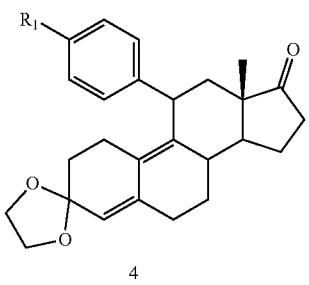

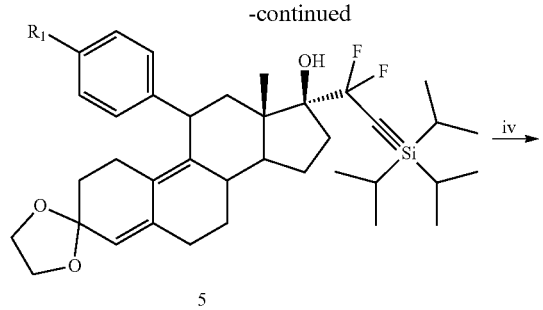
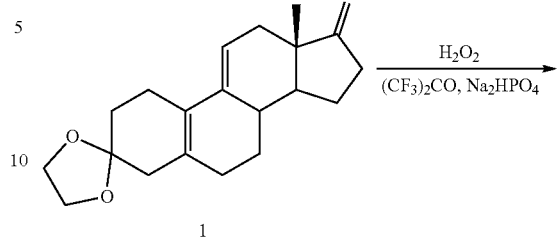

Scheme 2

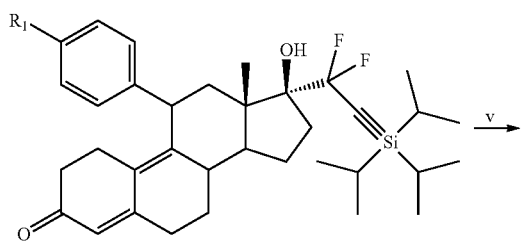

i) Epoxidation; ii) Grignard reaction; ii) Ac₂O, DMAP, Py; iii) 3-bromo-3,3-difluoro-1-triisopropylsilylpropyne, n-BuLi, THF; iv) 4N, HCl; v) TBAF, THF.

The general synthesis of the cytotoxic compounds described herein is generally accomplished by the use of a triisopropylsilyl (TIPS) protecting group to protect the 17a acetylenic hydrogen. Thus, an important intermediate in the synthesis of compounds having an acetylenic hydrogen is the compound of structure (V):

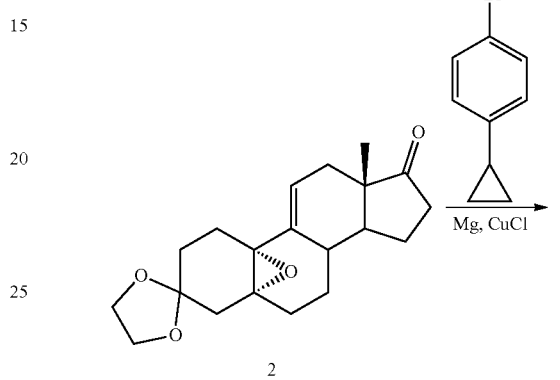

(V)

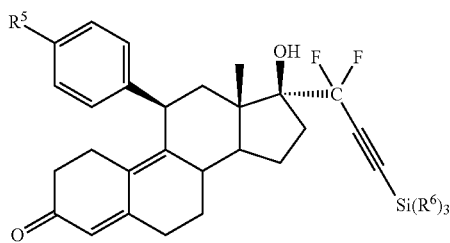

where:
$R^5$ is alkyl, alkenyl, alkylacyl, cycloalkyl, heterocycle, —CN, alkoxy, —N($R^6$)₂, —CON($R^6$)₂, —S(O)$R^6$, —S$R_6$, —SO₂$R^6$; or —(CH₂)$_p$—CH₂—Y; and
Y is H, O$R^6$, SCH₃, CF₃, —N($R^6$)₂; p=1-18; and
$R^6$ is H, alkyl, or cycloalkyl.
Specific examples of synthetic intermediates include compounds having the structure (V), where: $R^5$ is alkyl, alkenyl, alkylacyl, cycloalkyl, 1,3-imidazolyl, alkoxy, —N($R^6$)₂, —S$R_6$, or —SO₂$R^6$; and $R^6$ is H, lower alkyl, or cycloalkyl.

Synthesis of EC 330

EC330 may be synthesized by following the scheme outlined below (Scheme 2).

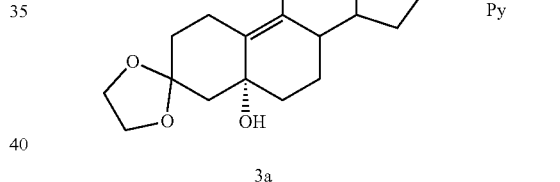
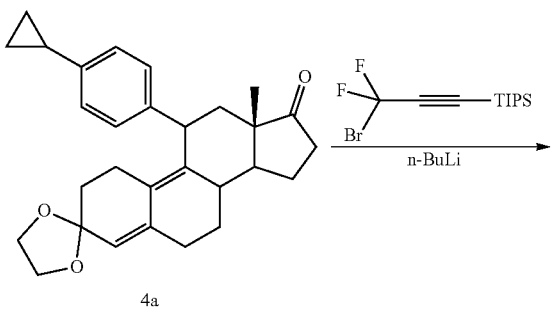
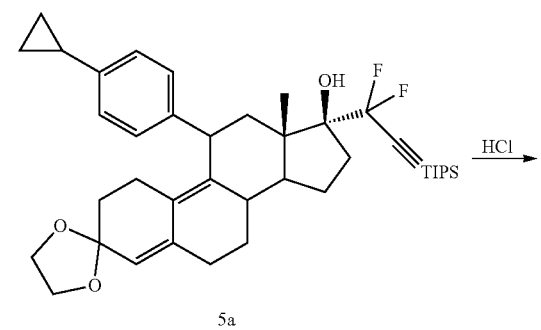

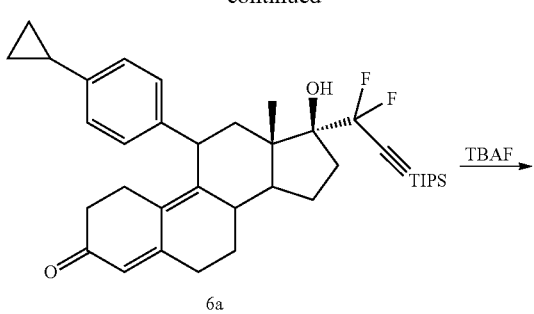

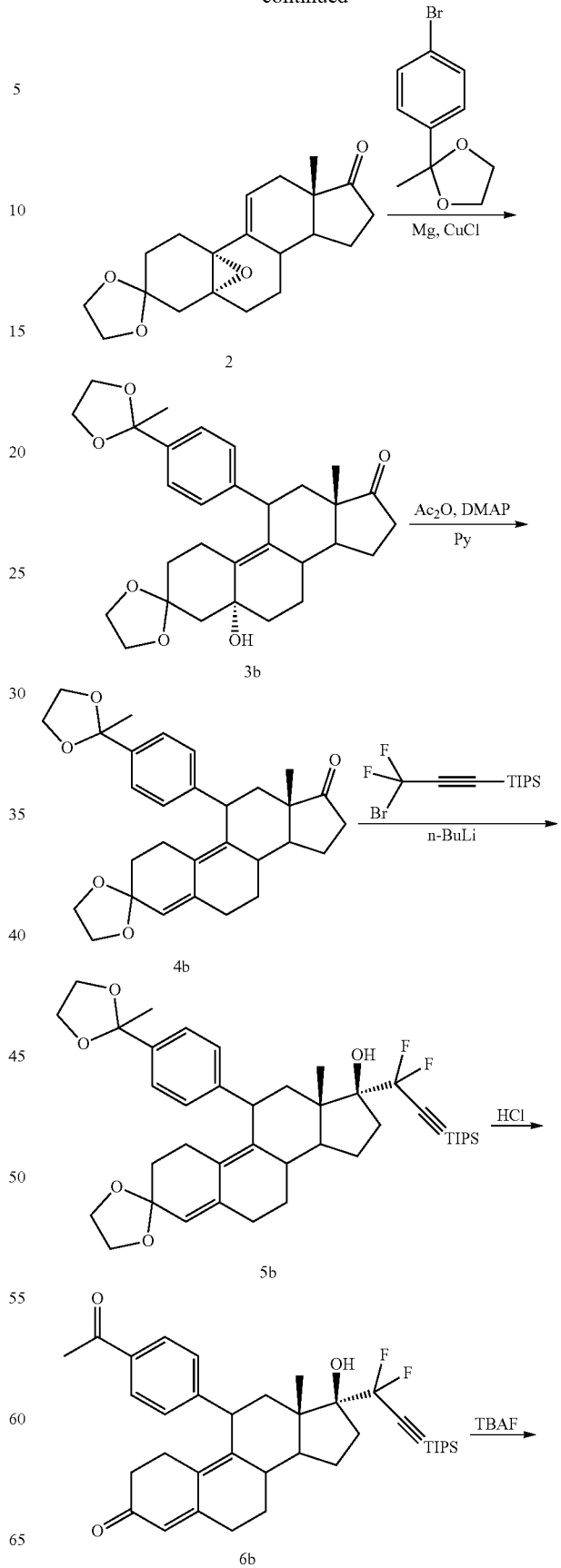

Intermediate 2 may be synthesized following the procedure reported in Rao et al. "New 11β-aryl-substituted Steroids Exhibit Both Progestational and Antiprogestational Activity", Steroids, 1998, 63, 523, which is incorporated herein by reference. Conjugate Grignard addition of the aryl cuprate reagent, generated by the reaction of 4-bromo-4'-cyclopropylbenzene with magnesium and cuprous chloride, at the 11 position of 2 afforded intermediate 3a. The cyclopropyl aryl derivative 3a was subjected to 5-hydroxy elimination using acetic anhydride and pyridine in presence of DMAP to afford 4a. The 17 addition of 3-lithium 3,3-difluoro-1-triisopropylsilylpropyne, generated by the reaction of 3-bromo-3,3-difluoro-1-triisopropylsilyl propyne with n-butyl lithium at −78° C. afforded compound 5a, which was hydrolyzed by 4N hydrochloric acid to give the key intermediate 6a. Removal of the triisopropylsilyl (TIPS) group by tetrabutylammonium fluoride (TBAF) afforded the final compound EC330.

Synthesis of EC 332

EC332 may be synthesized by following the scheme outlined below (Scheme 3).

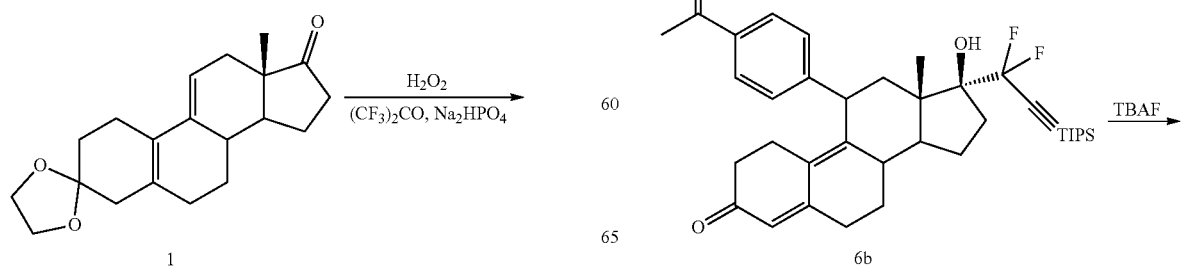

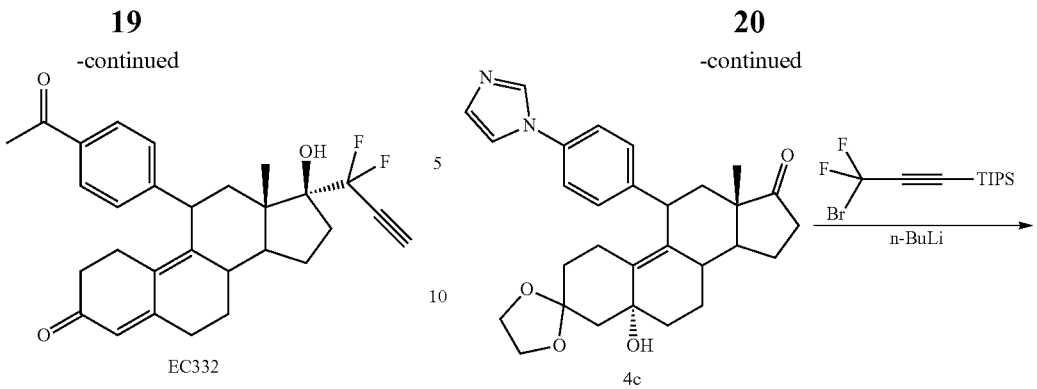

EC332

Synthesis of intermediates up to 4b may be accomplished following the procedure reported in Nickisch et al. "Synthesis and Biological Evaluation of Partially Fluorinated Antiprogestins and Mesoprogestins", Steroids, 2013, 78, 255, which is incorporated herein by reference. The 17 addition of lithium 3,3-difluoro-1-triisopropylsilylpropyne on 4b afforded 5b, which upon 3-ketal hydrolysis followed by removal of the TIPS group using TBAF provided EC-332.

Synthesis of EC 351

EC351 may be synthesized by following the scheme outlined below (Scheme 4).

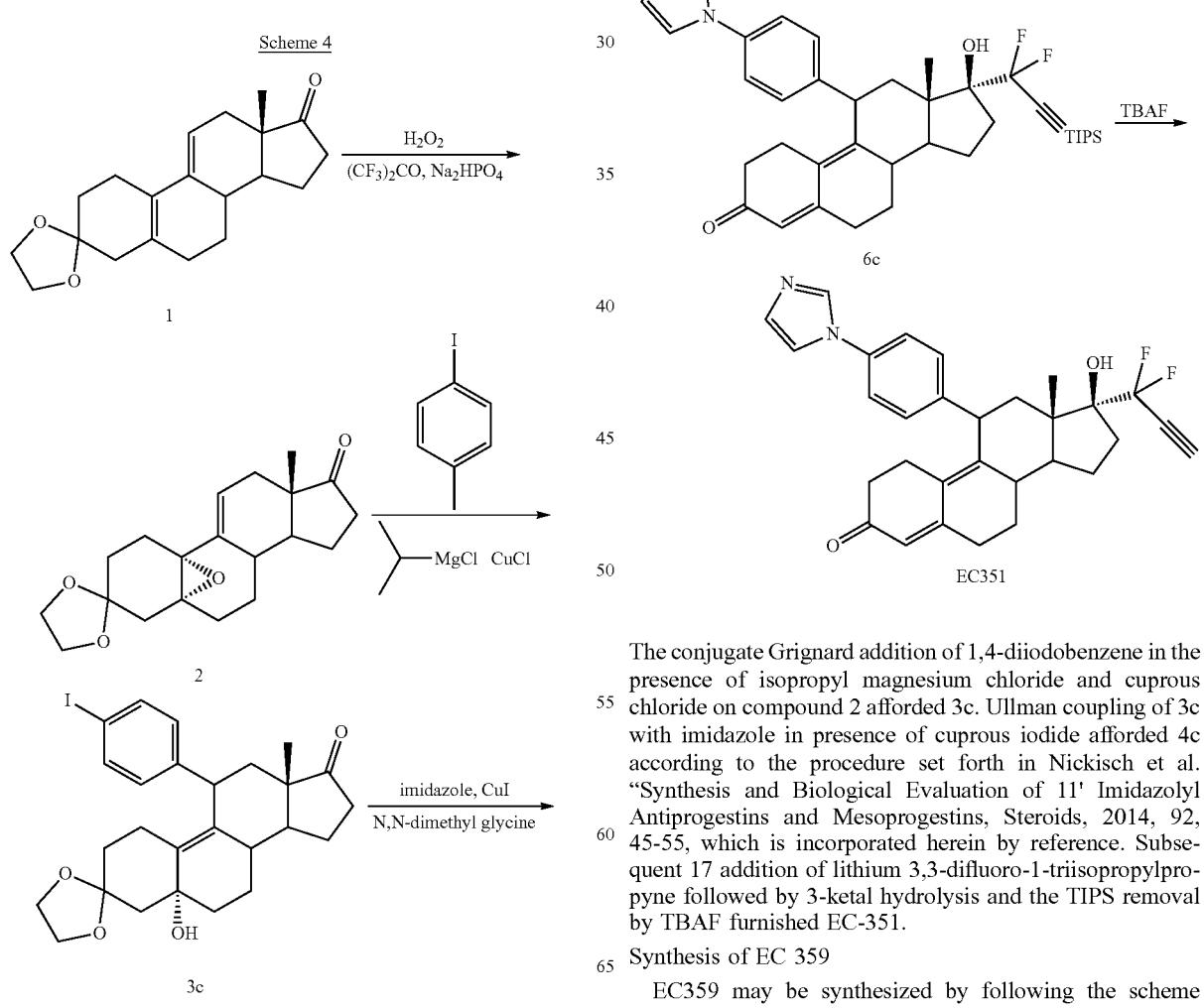

The conjugate Grignard addition of 1,4-diiodobenzene in the presence of isopropyl magnesium chloride and cuprous chloride on compound 2 afforded 3c. Ullman coupling of 3c with imidazole in presence of cuprous iodide afforded 4c according to the procedure set forth in Nickisch et al. "Synthesis and Biological Evaluation of 11' Imidazolyl Antiprogestins and Mesoprogestins, Steroids, 2014, 92, 45-55, which is incorporated herein by reference. Subsequent 17 addition of lithium 3,3-difluoro-1-triisopropylpropyne followed by 3-ketal hydrolysis and the TIPS removal by TBAF furnished EC-351.

Synthesis of EC 359

EC359 may be synthesized by following the scheme outlined below (Scheme 5).

Scheme 5
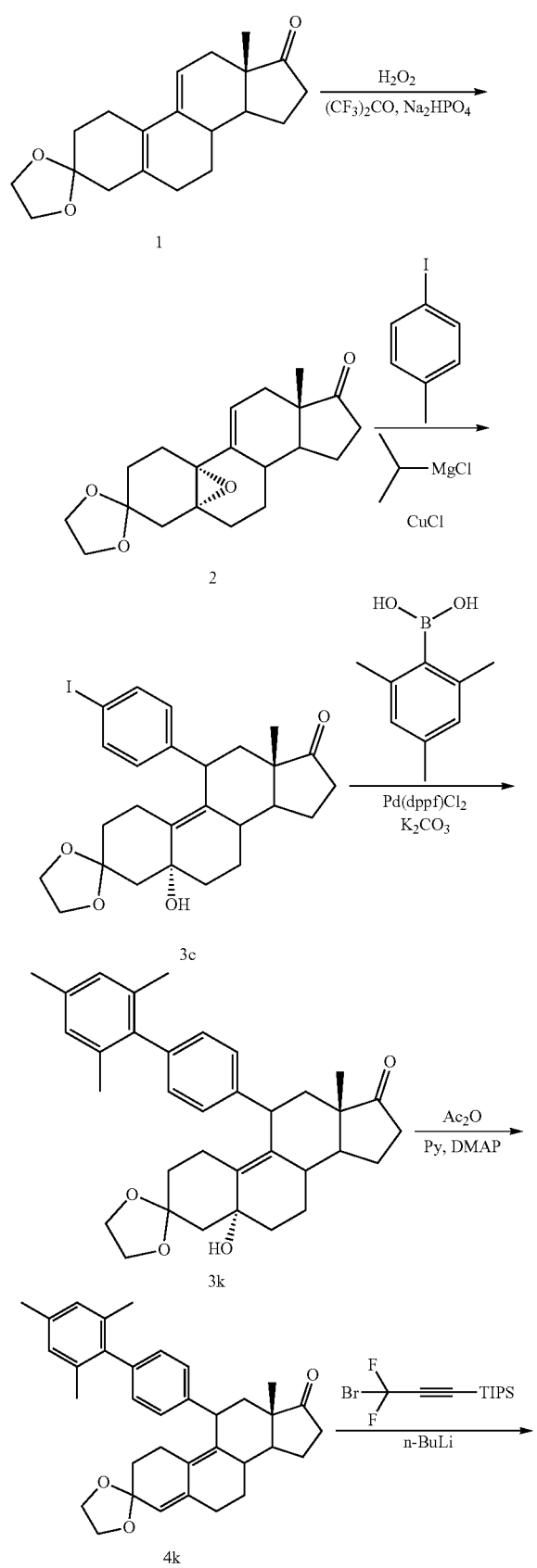
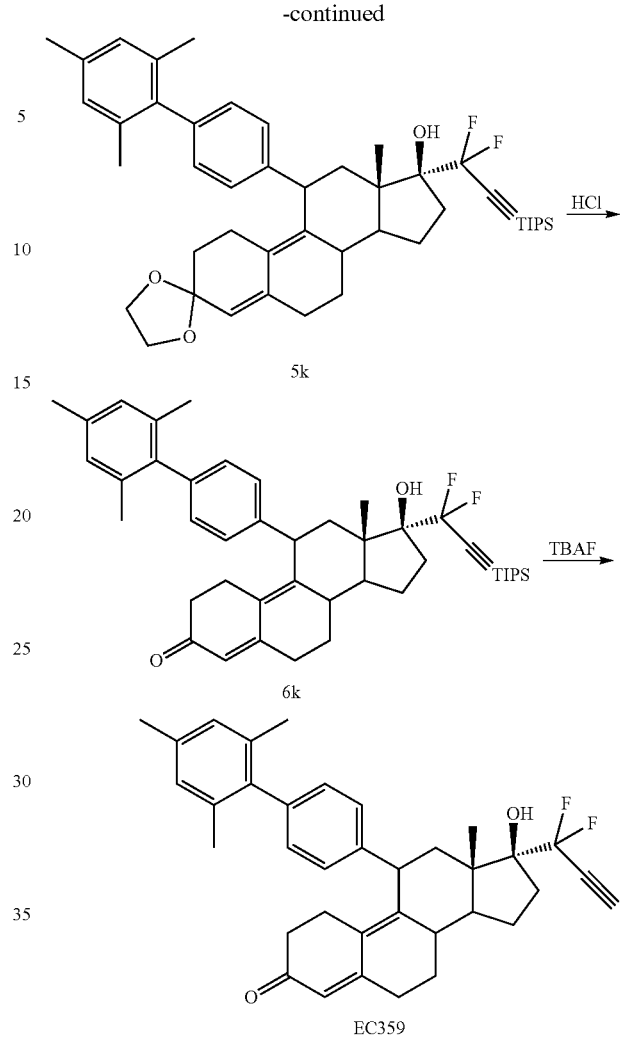
EC359 synthesis followed the same pattern as the previous schemes, except the synthesis of compound 3k which was prepared by the Suzuki coupling of 3c with the corresponding aryl boronic acid in presence of a palladium catalyst.
Synthesis of EC352, EC356, EC357, EC358, EC360, EC362 and EC363
EC352, EC356, EC357, EC358, EC360, EC362 and EC363 may be synthesized by following the scheme outlined below (Scheme 6).
Scheme 6
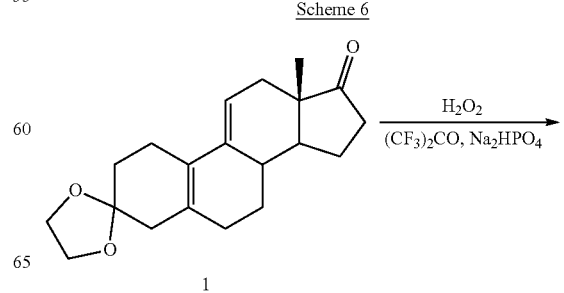

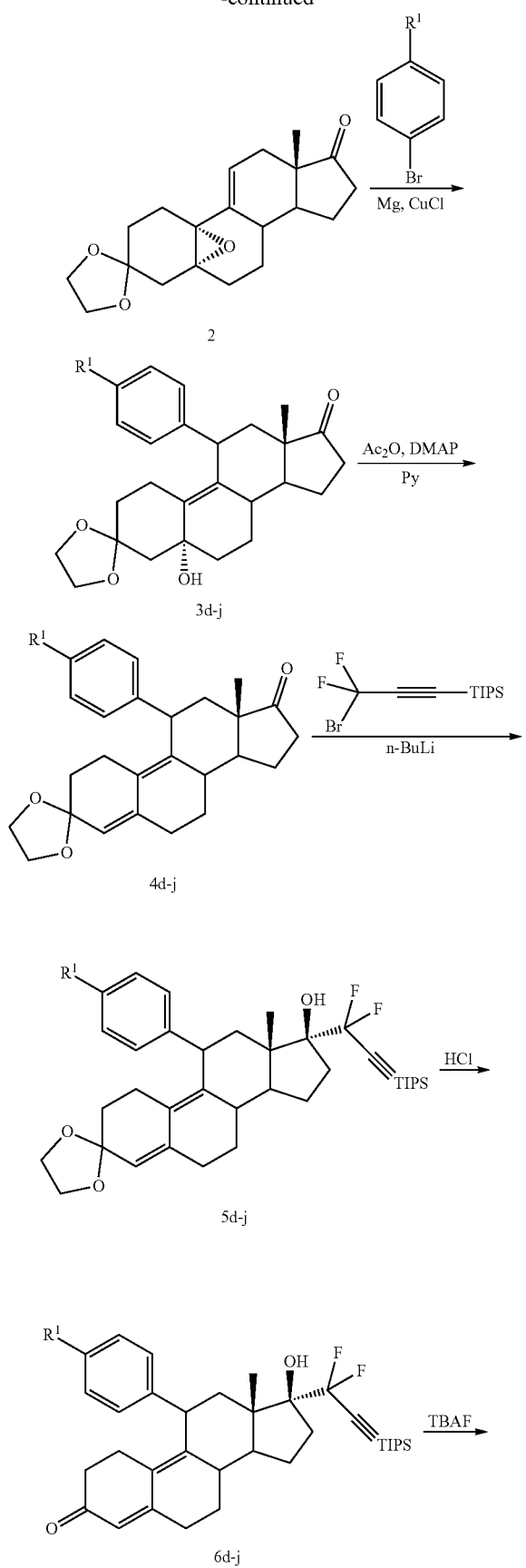

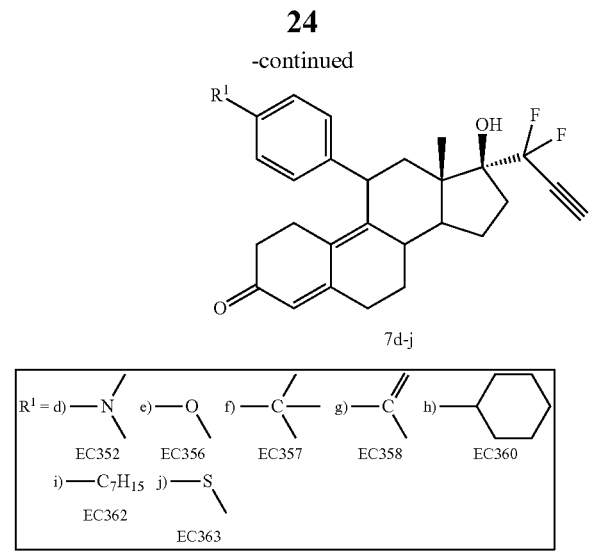

Epoxide 2 was subjected to conjugate Grignard addition with the corresponding 4-bromobenzene derivative in presence of magnesium and cuprous chloride to afford compounds 3d-j. Acetic anhydride and pyridine mediated 5-hydroxy elimination gave compounds 4d-j. Subsequent 17 addition of lithium 3,3-difluoro-1-triisoprylpropyne followed by 3-ketal hydrolysis and TIPS removal by TBAF furnished the respective EC compounds as shown in the scheme.

Synthesis of EC361

EC361 may be synthesized by following the scheme outlined below (Scheme 7).

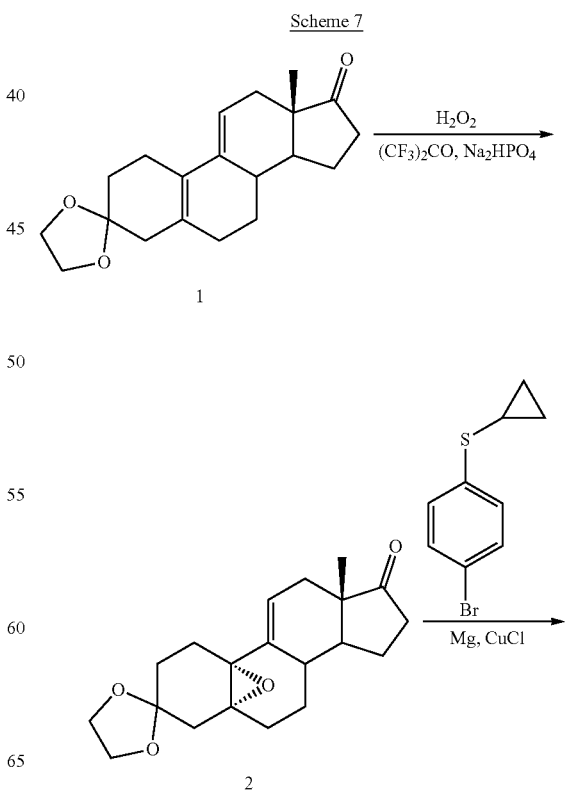

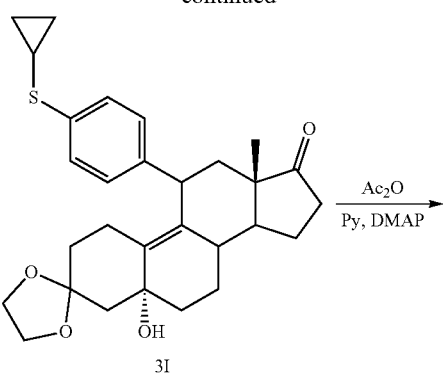

31

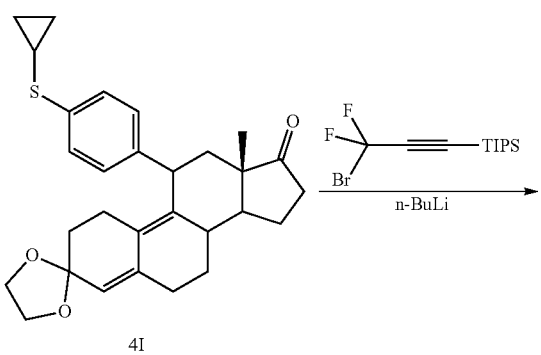

4I

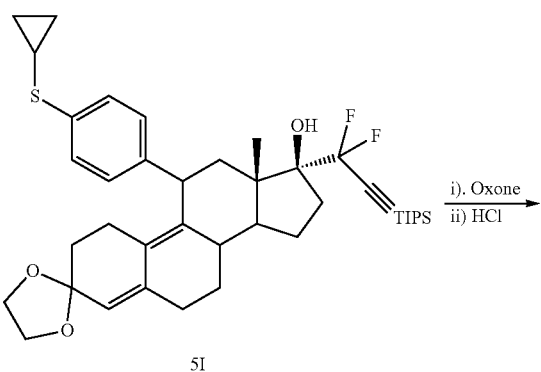

5I

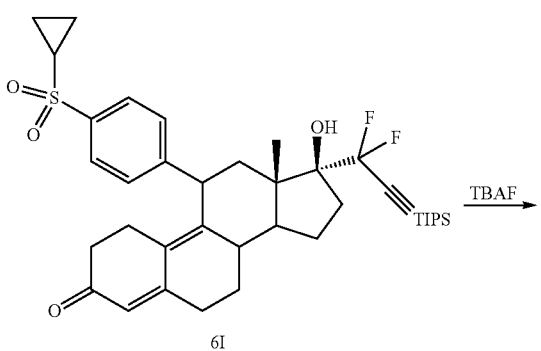

6I

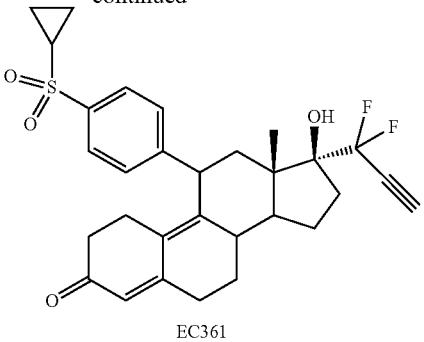

EC361

Conjugate Grignard reaction of 4-bromo-4'-cyclopropylphenyl sulfide and epoxide 2 in the presence of magnesium and cuprous chloride furnished compound 3I. Acetic anhydride and pyridine mediated 5-hydroxy elimination gave 4I, which upon 17 addition of lithium 3,3-difluoro-1-triisoprylpropyne afforded 5I. The 3-ketal hydrolysis of 5I by 4N hydrochloric acid followed by TIPS removal by TBAF gave EC361.

Cytotoxicity Studies—Use as Anticancer Agents

Compounds having the above described structures showed potent cytotoxicity in routine screening. These compounds were further tested to confirm the cytotoxicity in various cancer cell lines. The activity was confirmed to be dose dependent in a NCI-60 cell line panel that includes leukemia, non-small cell lung cancer, colon cancer, CNS cancer, melanoma, ovarian cancer, renal cancer, breast and prostate cancer cell lines. The high cytotoxic effects of these compounds were totally unexpected. Further studies showed the compound to reduce the tumor burden in human breast cancer and ovarian cancer xenograft models in mice. The compound exhibited specificity towards artificially induced LIF overexpressing cells over regular cancer cells. One significant advantage of the described compounds is that they act directly on the tumor cells/tumor stem cells and on the surrounding stromal fibroblasts (tumors with desmoplastic stroma or hypertrophic cell mass) as well.

Mechanism of Action Studies

Decidualization studies: The above compounds were investigated originally for the treatment of endometriosis. The compounds were tested in a decidualization assay using human endometrial stromal fibroblast (HESC) cells. In preparation for the possibility of embryonic attachment, the stromal cells in the endometrium undergo extensive waves of proliferation, remodeling, and terminal differentiation that transforms the endometrium into an endocrine gland, called decidua. This transformation is called decidualization and it is under the control by ovarian hormones.

Apoptosis has been shown to be important for endometrial function. The level of apoptosis increases from the proliferative phase through menstrual cycle and peaks at menses. This experiment will demonstrate that disruption of actin filaments will induce apoptosis in endometrial stromal fibroblast cells. However if the cells are subjected to conditions that induce decidualization, stromal cells will begin to differentiate instead of undergoing apoptosis. The above described compounds showed potent actin cytoskeletal disruption evident from phalloidin staining.

The above opens up various possibilities to study the mechanism of these compounds. First of all, the most common type of stromal cells are fibroblasts. In preparation for the implanting blastocyst, the endometrium becomes increasingly vascular with prominent increase in the levels of VEGF and PDGF and other cytokines and chemokines as well as alpha-smooth muscle actin is also induced in fibroblasts. Leukemia inhibitory factor (LIF) is a pleotropic cytokine from interleukin-6 (IL-6) family and has been shown to enhance oocyte maturation and preimplantation development. Recently evidence shows that LIF mediates proinvasive activation of tumor associated fibroblasts (CAF) in cancers. Moreover, additional evidence proved that LIF negatively regulates tumor suppressor p53 though STAT3/ID1/MDM2 axis in colorectal cancers. These recent studies prompt us to investigate whether the compounds above (specific examples of which are referred to herein as EC330/332) possess anticancer activity that mediated through LIF.

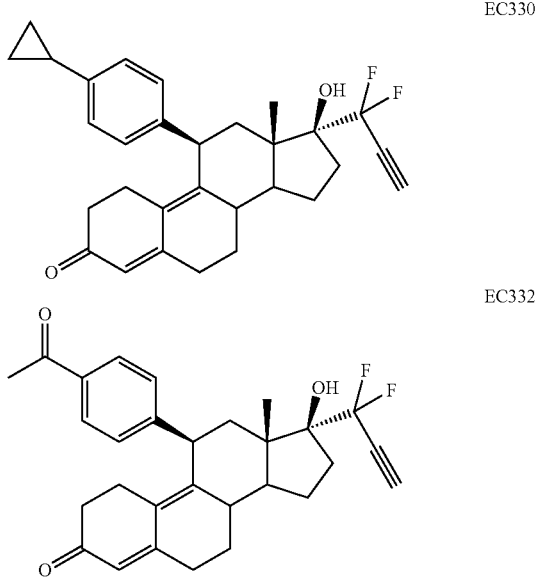

EC330 and EC332 exhibited IC50's in the low nanomolar concentrations in cytotoxicity assays (Table 1). They also exhibited 50% inhibition in the number of colonies formed at 5 nM concentration and a complete inhibition or no colonies were formed at 100 nM concentration (FIG. 2) in the soft agar colony formation assay.

EC330 and EC332 also showed complete abrogation of tube formation at 1 μM concentration at all measured time points in a human umbilical vein endothelial cells (HUVEC) tube formation assay. These results clearly underscore the anti-angiogenic activity of the compounds. Vascular endothelial growth factor (VEGF) is the most prominent among the angiogenic cytokines and is believed to play a central role in the process of neovascularization, both in cancer as well as other inflammatory diseases. A compound that inhibits angiogenesis can be used as monotherapy or in combination with conventional chemotherapy.

The compounds described herein exhibit indirect diminishment of the phosphorylation of SMAD thorough blocking TGF-beta. p53 levels in tumors were increased with treatment and levels of MDM2 were reduced. The downstream effecter of LIF, STAT3 phosphorylation was found reduced in the treated samples when compared to untreated control.

STAT3 phosphorylation may be utilized as a diagnostic maker/companion diagnostic to identify suitable patient population those could get benefit of LIF inhibition. Overexpression of LIF is associated with poor prognosis and increase incidence of chemoresistance. Targeting LIF and MDM2 to reactivate p53 is a potential therapeutic strategy for chemotherapy as well as in combination with other agents to alleviate chemoresistance. The dual inhibition of LIF and MDM2 would benefit a complete inhibition of tumor cells by inhibiting both tumor epithelium and it surrounding stromal fibroblast or desmoplastic stroma.

Clinical presentation of a lump in the breast is histologically viewed as a collagenous tumor or desmoplastic response created by myofibroblasts of the tumor stroma. The stroma of the prostate is characteristically muscular and diagnosis of reactive stroma associated with prostate cancer is one of poor prognosis. Recent studies show that targeting the stromal compartment in pancreatic cancer may have antitumor effects and may enhance sensitivity to radiation and chemotherapy. Disease progression in pancreatic cancer is associated with a robust fibrotic response, or desmoplasia, that promotes tumor progression and inhibits the entrance of therapeutic agents.

However, when we artificially induced LIF in human breast cancer cells (MCF-7), the compounds showed specificity towards these cells over regular breast cancer cells. The compounds prepared in the EC330 series showed specificity towards LIF in a range of 2 to 20 fold in term of cytotoxicity. We have found that the disclosed compounds showed antagonistic/agonistic property towards PR in vitro. Further studies revealed that the compound (EC330) significantly reduced the tumor growth in human triple negative breast cancer (TNBC) and ovarian cancer models.

Biological Testing

The following assays were performed:

Cytotoxicity Assays

In order to identify the mechanism of action of EC330/332, we checked cytotoxicity of these compounds in various cancer cells lines and derived IC50 values. Briefly, $5\times10^3$ cells were seeded in 96-well plates and incubated with compounds (0.0001-10 μmol/L) or dimethyl sulfoxide (DMSO; 0.02% v/v) for 24, 48, and 72 hours at 37° C. and cell viability was measured using a Fluoroscan plate reader. Results of cytotoxicity testing is presented in Table 11.

EC 330 was also tested using the NCI-60 Screening Methodology. The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). EC330 was solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80 TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% (GI0) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested. Results of testing for EC330 are presented in Tables 2-10.

TABLE 2

| Panel | Cell Line | | |
|---|---|---|---|
| | GI50 ($\log_{10}$GI50) | TGI ($\log_{10}$TGI) | LC50 ($\log_{10}$LC50) |
| Leukemia | | | |
| CCRF-CEM | <−8.00 | <−8.00 | <−8.00 |
| HL-60(TB) | <−8.00 | <−8.00 | <−8.00 |
| K-562 | −5.66 | >−4.00 | >−4.00 |
| MOLT-4 | −5.77 | −5.30 | >−4.00 |
| RPMI-8226 | −6.95 | −6.24 | >−4.00 |

TABLE 3

| Panel | Cell Line | | |
|---|---|---|---|
| | GI50 ($\log_{10}$GI50) | TGI ($\log_{10}$TGI) | LC50 ($\log_{10}$LC50) |
| Non-Small Cell Lung Cancer | | | |
| A549/ATCC | −5.61 | −4.61 | >−4.00 |
| EKVX | <−8.00 | <−8.00 | −7.44 |
| HOP-62 | −7.85 | −6.79 | −5.52 |
| HOP-92 | <−8.00 | <−8.00 | −7.72 |
| NCI-H226 | −5.58 | −5.04 | >−4.00 |
| NCI-H23 | <−8.00 | <−8.00 | >−4.00 |
| NCI-H332M | −5.42 | >−4.00 | >−4.00 |
| NCI-H460 | −5.57 | −4.80 | >−4.00 |
| NCI-H522 | <−8.00 | <−8.00 | <−8.00 |

TABLE 4

| Panel | Cell Line | | |
|---|---|---|---|
| | GI50 ($\log_{10}$GI50) | TGI ($\log_{10}$TGI) | LC50 ($\log_{10}$LC50) |
| Colon Cancer | | | |
| COLO 205 | −6.10 | −5.53 | −5.05 |
| HCC-2998 | −5.53 | −4.37 | >−4.00 |
| HCT-116 | −5.55 | −4.55 | >−4.00 |
| HCT-15 | −5.83 | >−4.00 | >−4.00 |
| HT29 | <−8.00 | −6.72 | −6.16 |
| KM12 | <−8.00 | −5.91 | −4.35 |
| SW-620 | −5.60 | −4.79 | >−4.00 |

TABLE 5

| Panel | Cell Line | | |
|---|---|---|---|
| | GI50 ($\log_{10}$GI50) | TGI ($\log_{10}$TGI) | LC50 ($\log_{10}$LC50) |
| CNS Cancer | | | |
| SF-268 | −6.90 | −6.43 | −5.81 |
| SF-295 | <−8.00 | <−8.00 | <−8.00 |
| SF-539 | <−8.00 | −7.77 | −7.28 |
| SNB-19 | −5.42 | >−4.00 | >−4.00 |
| U251 | −6.82 | −5.78 | −5.27 |

TABLE 6

| Panel | Cell Line | | |
|---|---|---|---|
| | GI50 ($\log_{10}$GI50) | TGI ($\log_{10}$TGI) | LC50 ($\log_{10}$LC50) |
| Melanoma | | | |
| LOX IMVI | <−8.00 | <−8.00 | <−8.00 |
| MALME-3M | <−8.00 | <−8.00 | −7.09 |
| M14 | −5.56 | −4.45 | >−4.00 |
| MDA-MB-435 | −5.73 | −5.03 | >−4.00 |
| SK-MEL-2 | −5.67 | −5.19 | −4.52 |
| SK-MEL-28 | −5.75 | −5.43 | −5.11 |
| SK-MEL-5 | −5.33 | −4.79 | −4.36 |
| UACC-257 | −5.15 | >−4.00 | >−4.00 |
| UACC-62 | −5.71 | −5.27 | >−4.00 |

TABLE 7

| Panel | Cell Line | | |
|---|---|---|---|
| | GI50 (log$_{10}$GI50) | TGI (log$_{10}$TGI) | LC50 (log$_{10}$LC50) |
| Ovarian Cancer | | | |
| IGROV1 | <−8.00 | <−8.00 | |
| OVCAR-3 | −7.89 | −6.85 | −6.03 |
| OVCAR-4 | −5.41 | >−4.00 | >−4.00 |
| OVCAR-5 | −5.97 | −5.25 | >−4.00 |
| OVCAR-8 | −5.81 | −4.43 | >−4.00 |
| NCI/ADR-RES | −7.59 | −5.41 | >−4.00 |
| SK-OV-3 | −6.93 | −6.55 | −6.18 |

TABLE 8

| Panel | Cell Line | | |
|---|---|---|---|
| | GI50 (log$_{10}$GI50) | TGI (log$_{10}$TGI) | LC50 (log$_{10}$LC50) |
| Prostate Cancer | | | |
| PC-3 | −6.29 | −5.53 | >−4.00 |
| DU-145 | −5.72 | −4.75 | >−4.00 |

TABLE 9

| Panel | Cell Line | | |
|---|---|---|---|
| | GI50 (log$_{10}$GI50) | TGI (log$_{10}$TGI) | LC50 (log$_{10}$LC50) |
| Renal Cancer | | | |
| 786-0 | <−8.00 | <−8.00 | <−8.00 |
| A498 | −6.58 | −6.01 | −5.41 |
| ACHN | −5.82 | −5.09 | >−4.00 |
| CAKI-1 | −7.53 | −6.41 | >−4.00 |
| RXF 393 | −5.97 | −5.09 | >−4.00 |
| SN12C | −5.42 | −4.58 | >−4.00 |
| TK-10 | −5.58 | −4.91 | >−4.00 |
| UO-31 | <−8.00 | <−8.00 | <−8.00 |

TABLE 10

| Panel | Cell Line | | |
|---|---|---|---|
| | GI50 (log$_{10}$GI50) | TGI (log$_{10}$TGI) | LC50 (log$_{10}$LC50) |
| Breast Cancer | | | |
| MCF7 | −5.91 | −4.96 | >−4.00 |
| MDA-MB-231 ATCC | −6.26 | −5.46 | >−4.00 |
| HS 578T | −5.64 | −4.99 | >−4.00 |
| BT-549 | −5.68 | −5.30 | >−4.00 |
| T-47D | <−8.00 | −5.00 | >−4.00 |
| MDA-MB-468 | −6.69 | −6.09 | −4.30 |

Soft Agar Colony Formation Assay

Colonies of cancer cells formed in soft agar in the presence and absence of the testing compounds is a standard assay to interpret in-vitro tumorigenic potential in the basal layer. Agar was prepared by mixing 1% DNA grade agar melted and cooled to 40° C. with an equal volume of (2×) Dulbecco's Modified Eagle's Medium (DMEM) to obtain 0.5% agar that was dispersed in a 6-well plate and allowed to solidify. A total of 0.6% agar was prepared in RPMI medium and mixed together with T47D cells (0.5×10$^6$ cells/mL) and immediately plated on the basal layer in the presence or absence of testing compounds. The cultures were incubated at 37° C. in a CO$_2$ incubator for 2 weeks, and colonies were stained with 0.005% crystal violet and observed under a light microscope. FIG. 1 depicts in vitro tumorigenicity potential of EC332 in T47D breast cancer cells.

Angiogenesis Assay

Figure 2:
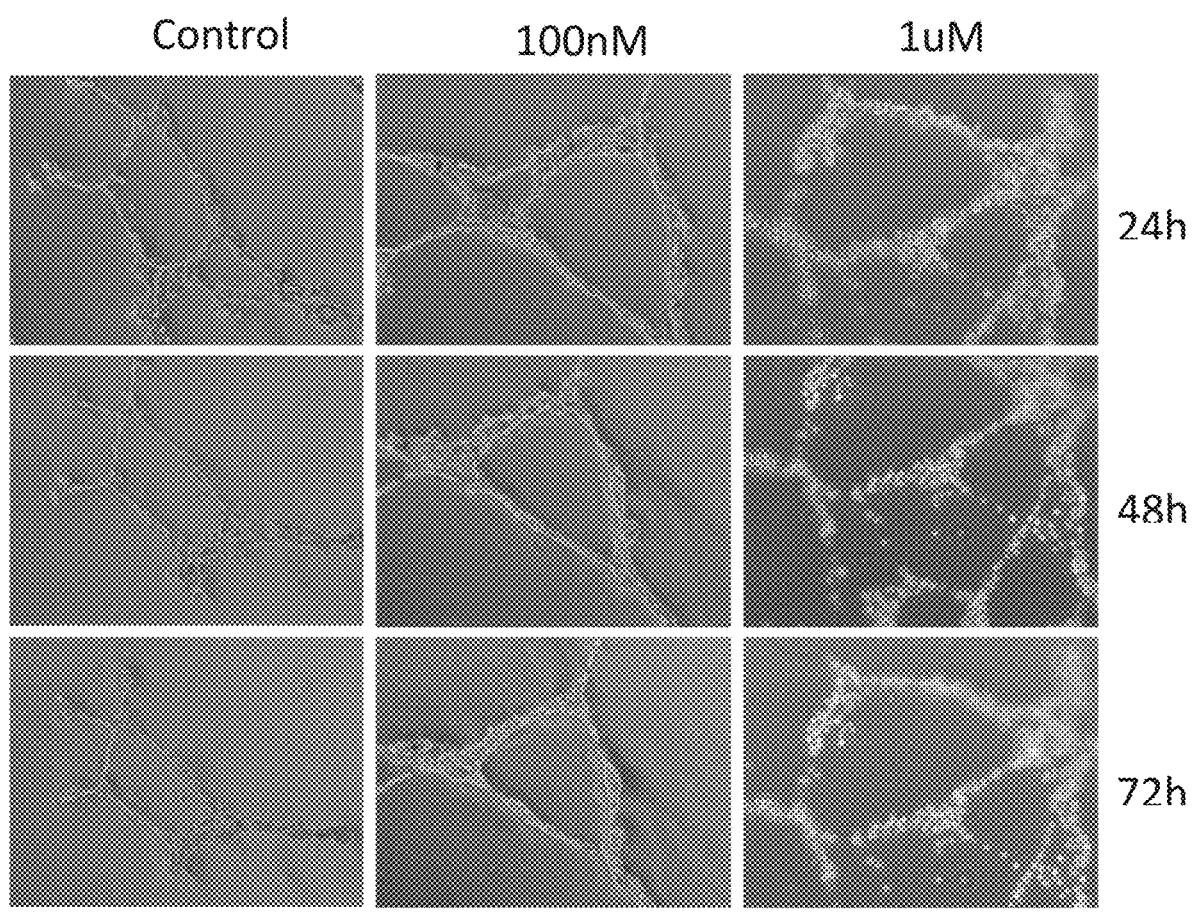
FIG. 2 shows that EC330 inhibited angiogenesis in vitro (tube formation assay)

Matrigel in vitro HUVECs tube formation assay: The tube formation assay was performed using 12-well plate coated with 100 μL Matrigel basement membrane matrix (BD Bioscience) per well and polymerized at 37° C. for 30 min. Human umbilical vascular endothelial cells (HUVECs) suspended in M199 medium containing 2% FBS were plated on the Matrigel at a density of 2×10$^5$ cells/well. Compounds (0.0001-10 μM) were then added together with VEGF. After 8 h, the Matrigel-induced morphological changes were photographed and the extent of capillary tube formation was evaluated by measuring the total tube length per field. FIG. 2 shows that EC330 inhibited angiogenesis in vitro (tube formation assay).

Decidualization Assay

Figure 3:
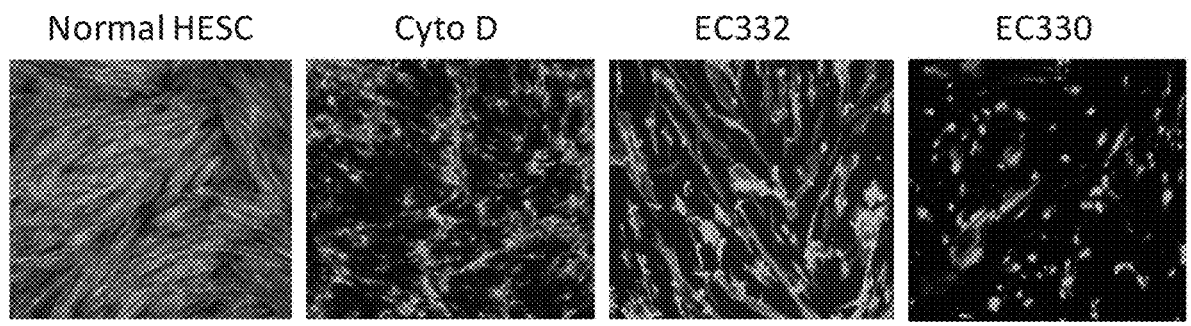
FIG. 3 shows that alpha-smooth muscle mediated cytoskeletal disruption of fibroblast in human endometrial stromal cells (HESC) cells treated with EC330/332.

Rationale of this assay is described above in mechanism of action studies section. Briefly, human stromal endometrial cells were plated in the presence and absence of progesterone and allow undergoing decidualization. The cells treated with test compounds of different concentrations and stained for actin cytocketal morphology using phalloidin staining and monitored under fluorescent microscope. The compounds that inhibited actin cytoskeletal polymerization was detected and compared with cytochalasin D. FIG. 3 shows that alpha-smooth muscle mediated cytoskeletal disruption of fibroblast in human endometrial stromal cells (HESC) cells treated with EC330/332.

Apoptosis Assay

Figure 4A:
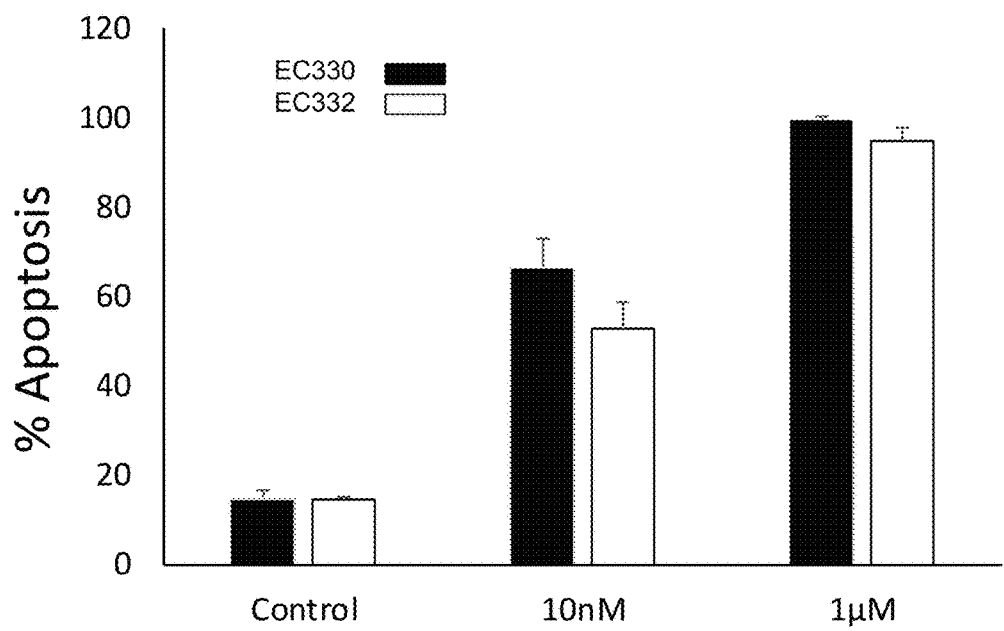
FIG. 4A shows the percent of apoptosis induced by treatment with EC330/332.
Figure 4B:
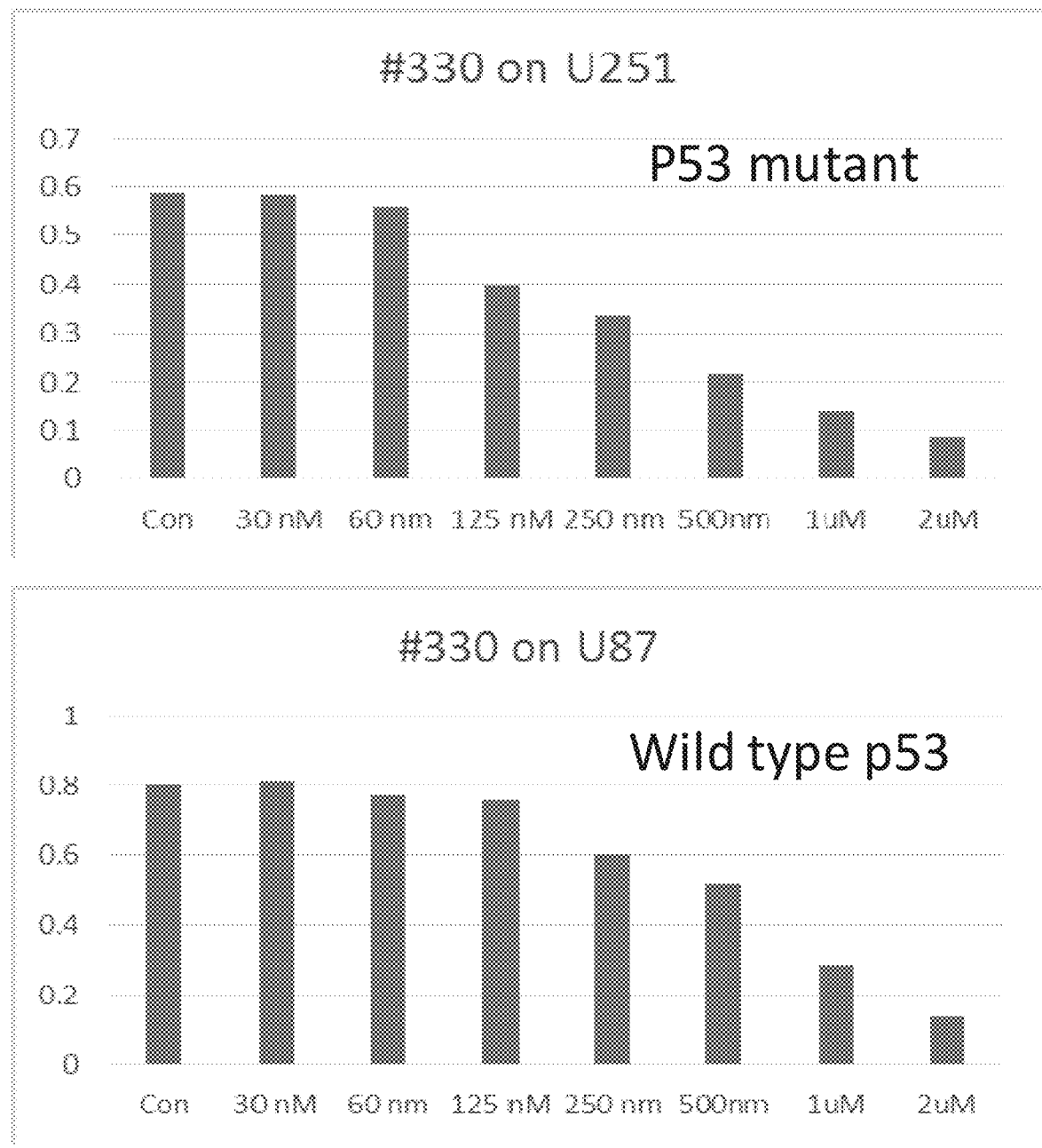
FIG. 4B shows the effect of EC330 on P53 for mutant vs. wild type glioma cells.
Figure 5:
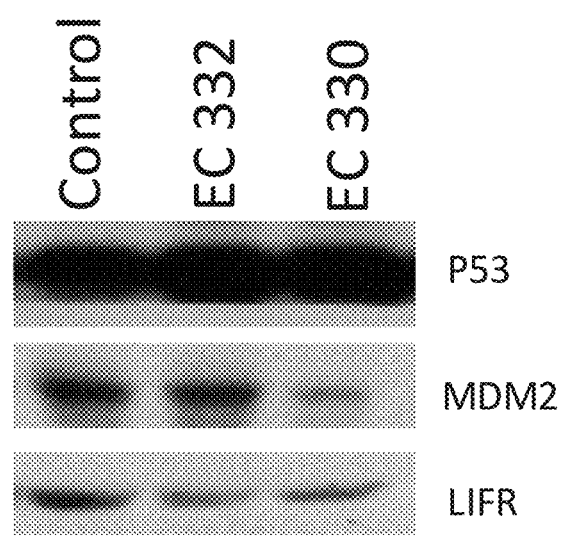
FIG. 5 shows that EC330/332 restore P53 levels by inhibiting MDM2 in MCF-7 cells.

Caspase-3/7 activity in HESE cells was measured using Caspase-Glo assay kit (Promega), as described before. Briefly, cells were homogenized in homogenization buffer (25 mmol/L HEPES, pH 7.5, 5 mmol/L —MgCl$_2$, and 1 mmol/L EGTA), protease inhibitors, and the homogenate was centrifuged at 13,000 rpm at 4° C. for 15 minutes. To 10 μL of the supernatant containing protein was added to an equal volume of the assay reagent and incubated at room temperature for 2 hours. The luminescence was measured using a luminometer. The percent of apoptosis induced by treatment with EC330/332 is shown in FIG. 4A. FIG. 4B shows the effect of EC330 on P53 for mutant vs. wild type glioma cells. FIG. 5 shows that EC330/332 restore P53 levels by inhibiting MDM2 in MCF-7 cells.

Immunohistochemistry Analysis

Figure 10:
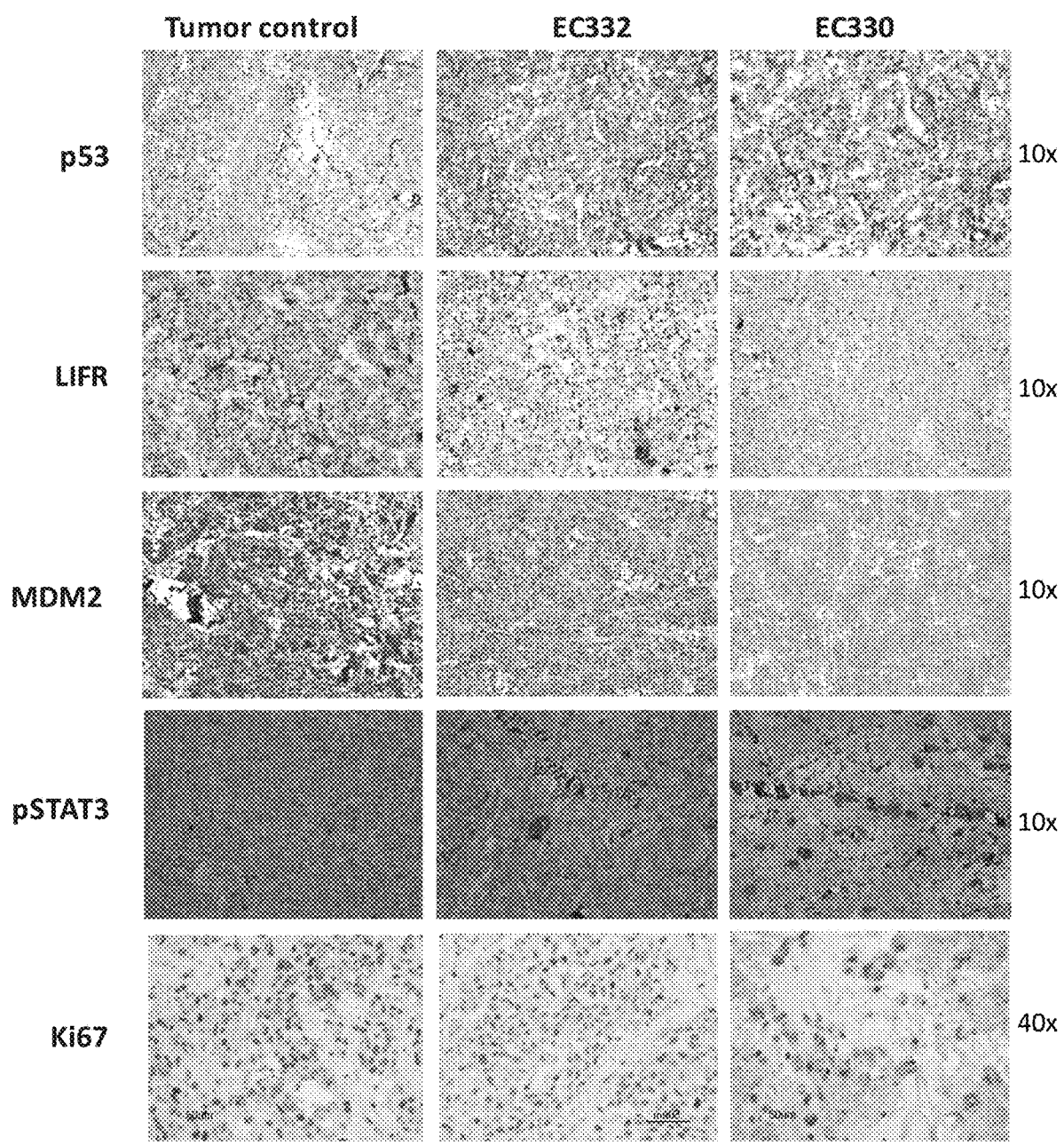
FIG. 10 shows the results of immunohistochemical analysis of various cells treated with EC330 and EC332.

Patient derived tumor (melanoma) was treated with the compounds at 10 nM and 1 uM for 5 days in RPMI medium and harvested on day 6 using established protocol and immunohistochemistry was performed for different antibodies including p53, LIF, MDM2, pSTAT$_3$, Ki67. Results of immunohistochemical analysis are shown in FIG. 10. The results show that EC332 & EC330 induce apoptosis and restore p53 by inhibiting MDM2 and LIF mediated STAT3 phosphorylation.

Western Blotting

In brief, T47D cells were treated with compounds for 3 days at different concentrations (10, 100 nM) and cell lysates were separated by 8% SDS-PAGE and transferred to polyvinylidene difluoride membranes. Membranes were then incubated with primary antibodies including phosphorylated and/or total p53, MDM2, actin, pSTAT3. After overnight incubation at 4° C., membranes were incubated with secondary antibodies. Immunoreactive bands were then visualized by the enhanced chemiluminescence (ECL) detection system (GE healthcare).

Tumor Xenograft Study

Figure 6A:
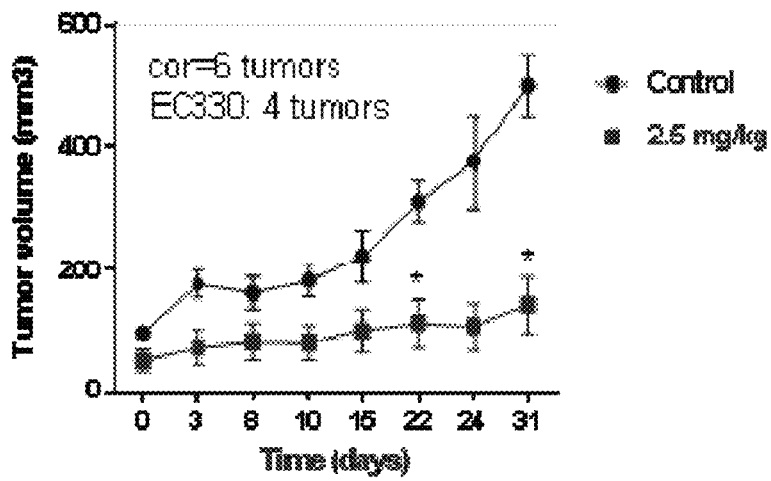
FIG. 6A depicts a graph of tumor volume vs. time for the administration of EC330 at 0.5 mg/kg 5 days per week in the MDA-MB-231 (TNBC) Xenograft (*p<0.001)
Figure 6B:
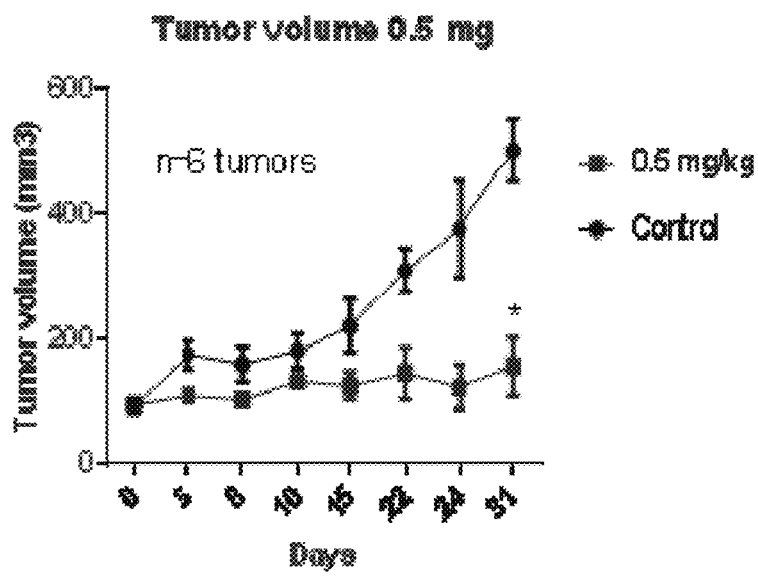
FIG. 6B depicts a graph of tumor volume vs. time for the administration of EC330 at 2.5 mg/kg twice weekly in the MDA-MB-231 (TNBC) Xenograft (*p<0.001)
Figure 7:
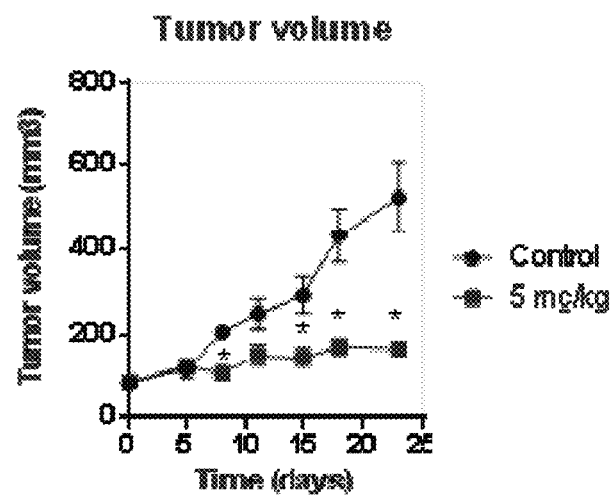
FIG. 7 depicts a graph of tumor volume vs. time for the administration of EC330 at 5 mg/kg 5 days per week in the IGROV1 (Ovarian) Xenograft (*p<0.001)
Figure 8:
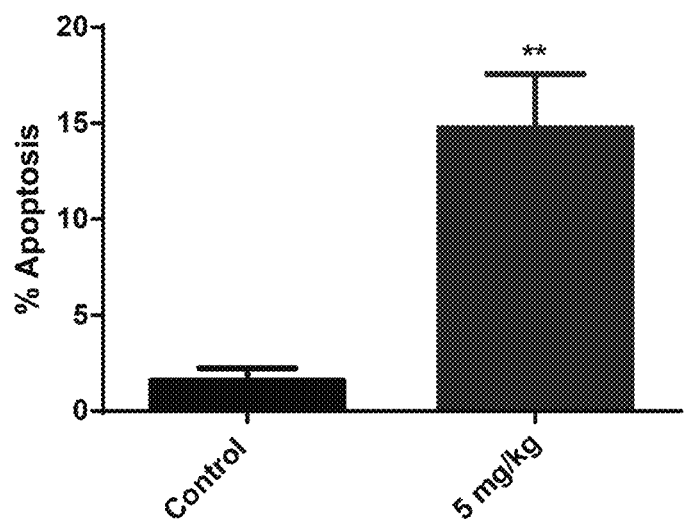
FIG. 8 depicts the percentage of apoptosis induced by EC330 measured in IGROV1 ovarian cancer xenograft tumors (**p<0.001)
Figure 9:
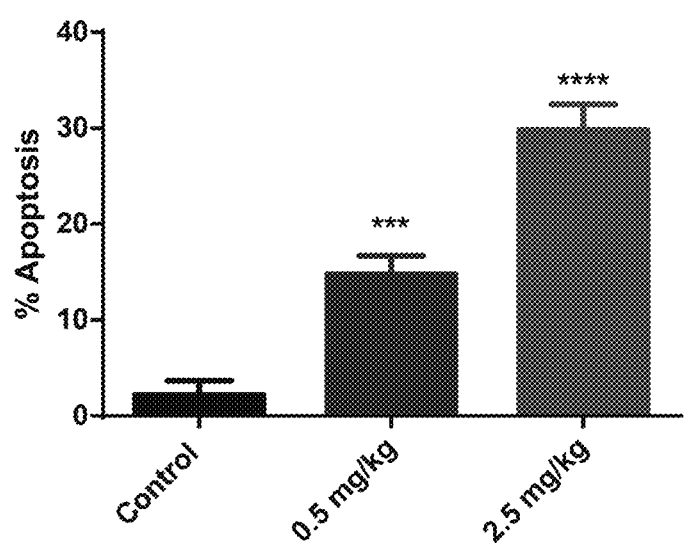
FIG. 9 depicts the percentage of apoptosis induced by EC330 measured in MDA-MB-231 breast cancer xenograft tumors (***p<0.001)

Uniform suspensions of human breast cancer MDA-MB-231 and human ovarian cancer IGROV1 cells (2×10$^6$) in 100 μL (0.02 carboxymethyl cellulose in phosphate buffered saline) were injected subcutaneously into the right and left flanks of 4- to 5-week-old female athymic nude mice (Charles River Laboratories). After 10 days, when the tumor diameter reaches 100 mm$^3$, the mice were randomly allocated to 3 groups of each containing 6 animals. Group 1 served as the untreated control, groups 2 and 3 received EC330 intraperitoneally at 0.5 mg/kg (daily dose for 5 days/week for 4 weeks) and 2.5 mg/kg (twice a week for 4 weeks), respectively. All drug was suspended in PBS followed by sonication (15 seconds with an intermittent interval of 5 seconds) for 1 minute. Tumors were allowed to reach palpability before drug intervention. Tumor size was measured every 3 days using digital Vernier Calipers and tumor volume was calculated using the ellipsoid formula [D×(d2)]/2, where D is the large diameter of the tumor and d represents the small diameter. On day 31, the mice were euthanized and tumors were harvested for protein and gene expression studies. FIG. 6A depicts a graph of tumor volume vs. time for the administration of EC330 at 0.5 mg/kg 5 days per week in the MDA-MB-231 (TNBC) Xenograft. FIG. 6B depicts a graph of tumor volume vs. time for the administration of EC300 at 2.5 mg/kg twice weekly in the MDA-MB-231 (TNBC) Xenograft. It is believed that STAT3 phosphorylation is reduced in tumors that underwent treatment with EC330 comparted to control as an indication of LIF downstream targets. FIG. 7 depicts a graph of tumor volume vs. time for the administration of EC300 at 5 mg/kg 5 days per week in the IGROV1 (Ovarian) Xenograft. The compound EC330 showed potent antitumor activity at doses of 5 mg/kg (5 days per week) and post tumor treatment for 4 weeks. STAT3 phosphorylation is reduced in tumors that underwent treatment compared to control which is an indication of LIF downstream target. FIG. 8 depicts the percentage of apoptosis induced by EC330 measured in IGR—OV1 ovarian cancer xenograft tumors. FIG. 9 depicts the percentage of apoptosis induced by EC330 measured in MDA-MB-231 breast cancer xenograft tumors. FIGS. 8 and 9 show that EC330 induced apoptosis dose dependently.

Figure 11:
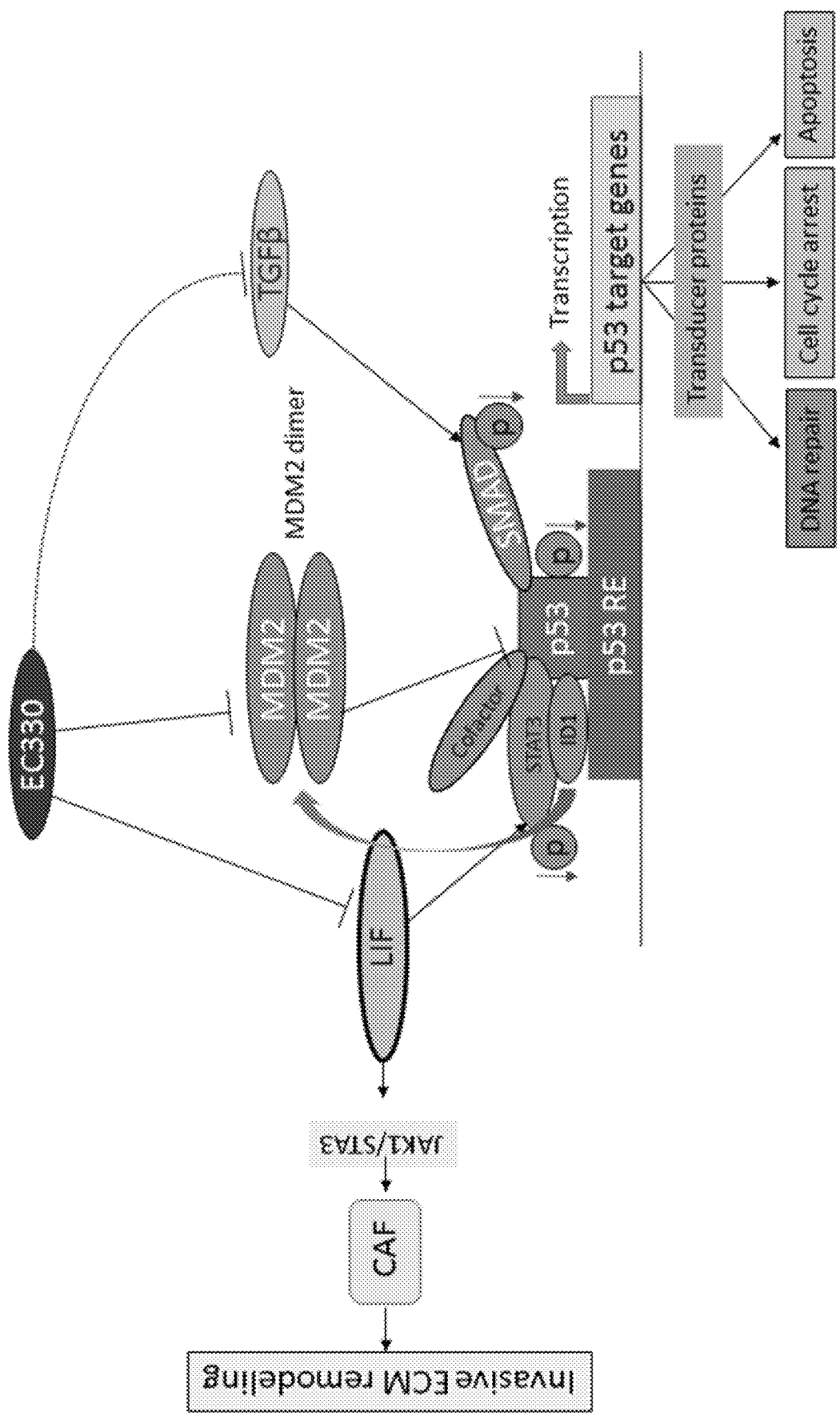
FIG. 11 shows the proposed mechanism of action of EC330/EC332 on cancer cells.

The proposed mechanism of action of EC330/EC332 on cancer cells is shown in FIG. 11.

Table 11 depicts short term (72 h) cytotoxicity of various cytotoxic compounds described herein in various cancer cell lines.

TABLE 11

| Compounds | IC50 (nM) | Cell line tested |
|---|---|---|
| EC330 | 35 | IGROV-1 (Ovarian cancer cells) |
|  | 34 | MDA-MB-231 (TNBC cells) |
|  | 25 | U87-MU (Glioma cells) |
|  | 20 | U251 (Glioma) |
|  | 25 | A549 (Lung cancer) |
|  | 80 | T47D (ER+ PR+ Breast Cancer) |
|  | 100 | MCF-7 (ER+ Breast Cancer) |
|  | 30 | PC3 (AR− Prostate Cancer) |
|  | 53 | LNCaP (AR+ Prostate) |
|  | 5 | Ishikawa (Endometrial Cancer) |
| EC332 | 90 | U87-MU (Glioma cells) |
|  | 40 | U251 (Glioma) |
|  | 75 | A549 (Lung cancer) |
|  | 110 | MDA-MB-231 (TNBC Cells) |

TABLE 11-continued

| Compounds | IC50 (nM) | Cell line tested |
|---|---|---|
|  | 45 | MCF-7 (ER+ Breast Cancer) |
|  | 200 | T47D (ER+ PR+ Breast Cancer) |
|  | 300 | PC3 (AR− Prostate Cancer) |
|  | 96 | LNCaP (AR+ Prostate) |
|  | 10 | Ishikawa (Endometrial Cancer) |
| EC358 | 35 | IGROV-1 |
|  | 40 | MDA-MB-231 (TNBC cells) |
|  | 25 | U87-MU (Glioma cells) |
| EC359 | 25 | IGROV-1 |
|  | 30 | MDA-MB-231 (TNBC cells) |
|  | 10 | U87-MU (Glioma cells) |
| EC360 | 22 | IGROV-1 |
|  | 40 | MDA-MB-231 (TNBC cells) |
|  | 73 | U87-MU (Glioma cells) |
| EC361 | 350 | IGROV-1 |
|  | 750 | MDA-MB-231 (TNBC cells) |
|  | 230 | U87-MU (Glioma cells) |
| EC351 | 500 | U251 (Glioma) |
| EC352 | 40 | U251 (Glioma) |
|  | 45 | A549 (Lung cancer) |
|  | 50 | U87-MU (Glioma) |
| EC355 | >10 (uM) | U87-MU (Glioma) |
|  | >10 (uM) | MDA-MB-231 (TNBC) |
| EC356 | 40 | A549 (Lung cancer) |
|  | 45 | U251 (Glioma) |
|  | 45 | U87-MU (Glioma cells) |
| EC362 | 25 | T47D (Breast cancer) |
|  | 7.5 | IGROV1 (Ovarian cancer) |
| EC363 | 30 | IGROV-1 (Ovarian cancer cells) |
|  | 30 | U87-MU (Glioma) |
| EC357 | 35 | A549 (Lung cancer) |
|  | 30 | U251 (Glioma) |
|  | 35 | U87-MU (Glioma cells) |

LIF Specificity Assay

LIF specificity of EC330 and related compounds synthesized in this series was conducted by comparing cytotoxicity of LIF-overexpressing MCF-7 ("MCF-7 LIF") vs. unmodified MCF-7 ("MCF-7") human breast cancer cells. Table 12 presents the results of this assay. The screening results show that LIF overexpressing cells were more vulnerable to cell death by EC330 and related compounds.

TABLE 12

| Compound | MCF-7 IC50 (nm) | MCF-7 LIF IC50 (nm) | Fold Change |
|---|---|---|---|
| EC330 | 250 | 80 | 3 |
| EC352 | >10000 | >10000 | 0 |
| EC356 | 500 | 250 | 2 |
| EC358 | 100 | 50 | 2 |
| EC360 | 500 | 250 | 2 |
| EC359 | 240 | 30 | 8 |
| EC361 | >10000 | 500 | 20 |
| EC362 | 50 | 25 | 2 |

Contraceptive Use

Embryo implantation is a critical step in the establishment of pregnancy in humans and other higher vertebrates. It has been showed in the literature that uterine LIF is expressed in the luminal epithelium on the day 3 of pregnancy and mediates via STAT3 in mouse and LIF overexpression during implantation in women. Hence inhibitors that block LIF action during early pregnancy would block embryo implantation and terminate the pregnancy. The above compounds, as shown, can act as LIF inhibitors which will terminate pregnancy and, therefore, can be used as a contraceptive.

Synthesis—Detailed Procedures

All the reagents and solvents were analytical grade and used without further purification. Thin-layer chromatography (TLC) analyses were carried out on silica gel GF (Analtech) glass plates (2.5 cm×10 cm with 250 µM layer and pre-scored) and visualized by UV light (254 nm). Flash column chromatography was performed on 32-64 µM silica gel obtained from EM Science, Gibbstown, N.J. Melting points were determined on an Electro thermal MEL-TEMP apparatus and are uncorrected. Nuclear magnetic resonance spectra were recorded on a Bruker ARX (300 MHz) spectrometer as deuterochloroform (CDCl$_3$) solutions using tetramethylsilane (TMS) as an internal standard (δ=0) unless noted otherwise. IR spectra were recorded on an Avatar spectrophotometer 370 FT-IR.

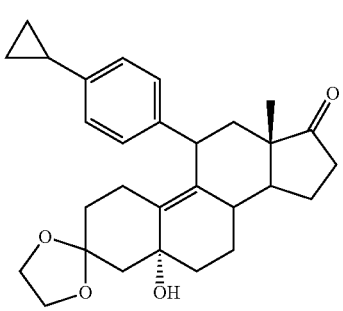

3a 3,3-Ethylenedioxy-5α-hydroxy-11β-[4'-cyclopropylphenyl]-estr-9-ene-17-one (3a)

A three neck dried flask was charged with Mg turnings (674 mg, 28.1 mmol), a crystal of I2 was added and swirled over the Mg and kept for 5 min. 30 mL of anhydrous THF was added followed by 1 mL of 1,2-dibromoethane. The reaction was slightly warmed with a heat gun. When Mg starts reacting, a solution of 4-bromocyclopropylbenzene (5.36 g, 27.2 mmol) in 50 mL of THF was added dropwise over a period of 10 min. The reaction was stirred under reflux for 1 h. Afterward, the reaction was cooled to room temperature and CuCl (816 mg, 8.16 mmol) was added. The reaction was stirred for 30 min and then a solution of the epoxide 2 (2 g, 9.07 mmol) in THF (30 mL) was added dropwise and stirred for 1 h. The TLC showed a more polar product with respect to the epoxide. The reaction was cooled and quenched by the addition of sat. solution of NH$_4$Cl and extracted with ethyl acetate (3×100 mL); the organic layers were washed with water and brine and the solvent was removed under vacuum. The crude was purified by column chromatography using 50% of ethyl acetate in hexane to get 3.6 g of a white foam (89% yield). mp 181-182° C. UV (nm): 200, 231. RE 0.15 (5:5, Hex:EtOAc). FT IR (ATR, cm$^{-1}$): 3521, 2927, 1735, 1512.

$^1$H NMR (CDCl$_3$, 300 MHz) δ 0.48 (s, 3H, H-18), 0.64 (m, 2H, cyclopropyl), 0.91 (m, 2H, cyclopropyl), 3.9 (m, 4H, ketal), 4.28 (d, J=6.3 Hz, H-11), 4.3 (s, 1H, —OH), 6.9 (d, J=8.1 Hz, 2H, H—Ar), 7.1 (d, J=8.1 Hz, 2H, H—Ar).

$^{13}$C NMR (CDCl$_3$, 75 MHz) δ 9.10 (cyclopropyl), 9.21 (cyclopropyl), 14.28 (C-18), 14.87 (cyclopropyl), 64.02 (ketal), 64.64 (ketal), 69.98 (C-5), 108.64 (C-3), 125.50 (C—Ar), 126.94 (C—Ar), 133.66 (C-10), 135.02 (C-9), 141.10 (C—Ar), 143.04 (C—Ar), 219.93 (C-17).

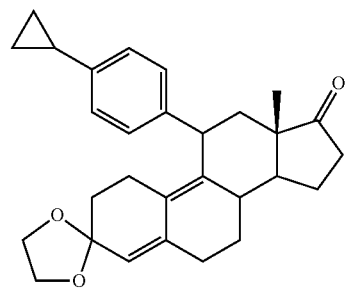

4a 3,3-Ethylendioxy-11β-[4-p-(cyclopropyl)phenyl]estra-4,9-dien-17-one (4a)

To a solution of compound 3a (3 g, 6.68 mmol) in pyridine (30 mL), acetic anhydride (3.2 mL, 33.4 mmol) and DMAP (81.6 mg, 0.66 mmol) were added and the mixture was heated at 65° C. for 36 h. TLC showed a less polar product compared to the starting material. Solvents were distilled off under high vacuum. The purification of this compound was done by column chromatography using basic alumina with a mixture of 20% ethyl acetate in hexane to get 2.41 g of a white powder of 4a (67% yield), mp 182-186° C. R$_f$ 0.66 (5:5, Hex:EtOAc). UV (nm): 200,250. FT IR (ATR, cm$^{-1}$): 2959, 2921, 1737, 1624.

$^1$H NMR (CDCl$_3$, 300 MHz) δ 0.50 (s, 3H, H-18), 0.64 (m, 2H, cyclopropyl), 0.91 (m, 2H, cyclopropyl), 3.9 (m, 4H, ketal), 4.26 (d, J=6.3 Hz, H-11), 5.38 (s, 1H, H-4), 6.9 (d, J=8.1 Hz, 2H, H—Ar), 7.1 (d, J=8.1 Hz, 2H, H—Ar).

$^{13}$C NMR (CDCl$_3$, 75 MHz) δ 9.13 (cyclopropyl), 9.21 (cyclopropyl), 14.42 (C-18), 14.88 (cyclopropyl), 64.39 (ketal), 64.53 (ketal), 106.13 (C-3), 121.7 (C-4), 125.61 (C—Ar), 126.99 (C—Ar), 130.10 (C-10), 137.63 (C-9), 139.33 (C-5), 141.16 (C—Ar), 141.75 (C—Ar), 219.69 (C-17).

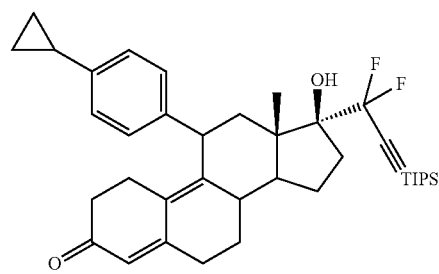

6a

17α-[1,1-difluoro-3-[tris(1-methylethyl)silyl]-2-propyn-1-yl]-17β-hydroxy-11β-[4-p-(cyclopropyl) phenyl]estra-4,9-dien-3-one. (6a)

2.3 g of the steroid 4a (5.3 mmol) and 3.92 g (12.6 mmol) of the 3-bromo-3,3-difluoro-1-triisopropylsilylpropyne were dissolved in THF (230 mL) and cooled to −78° C. After this, 5 mL (12.6 mmol) of 2.5 M solution of n-BuLi was added dropwise and the reaction was stirred for 1 h in which time the TLC showed a less polar product compared to the starting material. The reaction was quenched by adding sat solution of NH$_4$Cl and extracted with ethyl acetate and the organic layer was washed with water and brine. The solvent was removed under vacuum to afford crude 5a which was dissolved in 75 mL of methanol and 75 mL of THF. 3.7 mL (15 mmol) of a 4N solution of HCl was added dropwise and stirred for 1 h. The TLC showed completion of the reaction. The reaction was quenched by adding a sat solution of sodium bicarbonate and extracted with ethyl acetate (3×100 mL). The combined organic layers were washed with water and brine and the solvent was removed under vacuum. The crude was purified by column chromatography using 30% of ethyl acetate in hexane to get a beige powder of 6a (quantitative yield). mp 99-101° C. $R_f$: 0.45 (7:3, Hex:EtOAc). UV (nm): 200, 230, 299. FT IR (ATR, cm$^{-1}$): 3412, 2940, 2873, 1651, 1591.

$^1$H NMR (CDCl$_3$, 300 MHz) δ 0.60 (s, 3H, H-18), 0.64 (m, 2H, cyclopropyl), 0.91 (m, 2H, cyclopropyl), 1.03 (s, 3H, Si(C$\underline{H}$)$_3$(CH$_3$)$_6$), 1.08 (s, 18H, Si(CH)$_3$(C$\underline{H}_3$)$_6$), 4.3 (s, H-11), 5.76 (s, 1H, H-4), 6.9 (d, J=8.4 Hz, 2H, H—Ar), 7.04 (d, J=8.4 Hz, 2H, H—Ar).

$^{13}$C NMR (CDCl$_3$, 75 MHz) δ 9.17 (cyclopropyl), 9.26 (cyclopropyl), 10.92 (C-18), 14.51 (cyclopropyl), 18.51 (Si(CH)$_3$(C$\underline{H}_3$)$_6$), 24.40 (Si(C$\underline{H}$)$_3$(CH$_3$)$_6$), 86.63 (t, J=24 Hz, (C$\underline{F}_2$CC)), 122.90 (C-4), 125.74 (C—Ar), 126.66 (C—Ar), 129.46 (C-10), 141.29 (C—Ar), 141.39 (C—Ar), 145.24 (C-9), 156.50 (C-5), 199.45 (C-3).

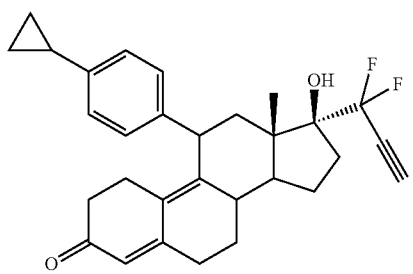

17α-(1,1-difluoro-2-propyn-1-yl)-17β-hydroxy-11β-[4-p-(cyclopropyl)phenyl]estra-4,9-dien-3-one (EC330)

To a solution of compound 6a (2 g, 3.3 mmol) in 200 mL of THF was added a 1 M solution of TBAF (6.7 mL) and the mixture was stirred for 30 min. TLC showed a more polar product. The reaction was quenched by adding water and extracted with ethyl acetate (3×100 mL). The combined organic layers were washed with water and brine and the solvent was removed under vacuum. The crude was purified by column chromatography using 50% of ethyl acetate in hexane to get 1.08 g of a white powder of EC330. (71% yield), mp 187-188° C. $R_f$: 0.26 (7:3, Hex:EtOAc). UV (nm): 200, 230, 303. FT IR (ATR, cm$^{-1}$): 3284, 3217, 2947, 2124, 1645, 1604.

$^1$H NMR (CDCl$_3$, 300 MHz) δ 0.61 (s, 3H, H-18), 0.65 (m, 2H, cyclopropyl), 0.93 (m, 2H, cyclopropyl), 2.90 (t, J=5.4 Hz, 1H, acetylenic hydrogen), 4.3 (d, J=7.2 Hz, 1H, H-11), 5.76 (s, 1H, H-4), 6.9 (d, J=8.4 Hz, 2H, H—Ar), 7.06 (d, J=8.4 Hz, 2H, H—Ar).

$^{13}$C NMR (CDCl$_3$, 75 MHz) δ 9.17 (cyclopropyl), 9.26 (cyclopropyl), 14.89 (C-18), 16.61 (cyclopropyl), 86.17 (t, J=24 Hz, (C$\underline{F}_2$CC)), 123.01 (C-4), 125.76 (C—Ar), 126.67 (C—Ar), 129.56 (C-10), 141.18 (C—Ar), 141.44 (C—Ar), 145.05 (C-9), 156.34 (C-5), 199.46 (C-3).

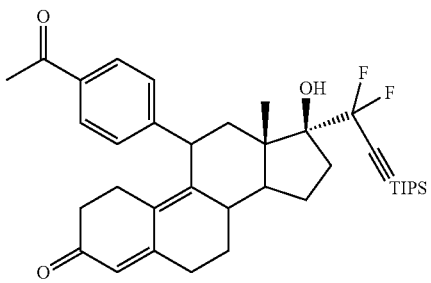

17α-[1,1-difluoro-3-[tris(1-methylethyl)silyl]-2-propyn-1-yl]-17β-hydroxy-11β-[4-p-(acetyl) phenyl]estra-4,9-dien-3-one. (6b)

Following the procedure described for compound 6a, 0.77 g of compound 4b (1.61 mmol) was reacted with 2.5 g of 3-bromo-3,3-difluoro-1-triisopropylsilylpropyne (8.1 mmol) and 3.1 mL of 2.5M solution of n-BuLi to afford crude 5b which was hydrolysed by 1.4 ml 4N hydrochloric acid to afford 440 mg of 6b as an amorphous solid in 60% yield. UV (nm): 200, 230, 290 FT IR (ATR, cm$^{-1}$): 3284, 3217, 2947, 2124, 1732, 1645, 1604.

$^1$H NMR (CDCl$_3$, 300 MHz) δ 0.58 (s, 3H, H-18), 1.11 (s, 18H, Si(CH)$_3$(CH$_3$)$_6$), 2.73 (s, 3H), 4.45 (m, H-11), 5.79 (s, 1H, H-4), 7.28 (d, J=8.3 Hz, 2H, H—Ar), 7.88 (d, J=8.3 Hz, 2H, H—Ar).

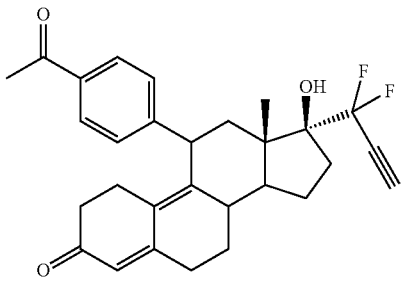

17α-(1,1-difluoro-2-propyn-1-yl)-17β-hydroxy-11β-[4-p-(acetyl)phenyl]estra-4,9-dien-3-one (EC332)

To a solution of compound 6b (750 mg, 1.03 mmol) in 50 mL of methanol was cooled to 0° C. as 0.7 ml of 4N HCl was added dropwise. The reaction was stirred for an hour during which time TLC showed complete conversion of the starting material to the product. Reaction was quenched by the addition of sat. sodium bicarbonate and extracted with EtOAc (3×100 ml). The combined organic layers were washed with water and brine and the solvent was removed under vacuum to get the crude which was dissolved in 50 ml of THF and was treated with a 1M solution of TBAF (1.25 mL) and the mixture was stirred for 30 min. TLC showed a more polar product. The reaction was quenched by adding water and extracted with ethyl acetate (3×100 mL). The combined organic layers were washed with water and brine and the solvent was removed under vacuum. The crude was purified by column chromatography using 50% of ethyl acetate in hexane to get 400 mg of EC332 as an off white powder. (83% yield), UV (nm): 200, 230, 303 FT IR (ATR, cm$^{-1}$): 3284, 3217, 2947, 2124, 1732, 1645, 1604.

$^{-1}$H NMR (CDCl$_3$, 300 MHz) δ 0.57 (s, 3H, H-18), 2.73 (s, 3H), 2.91 (t, J=5.3 Hz, 1H, acetylenic hydrogen), 4.1 (d, J=7.2 Hz, 1H, H-11), 5.79 (s, 1H, H-4), 7.28 (d, J=8.3 Hz, 2H, H—Ar), 7.87 (d, J=8.3 Hz, 2H, H—Ar).

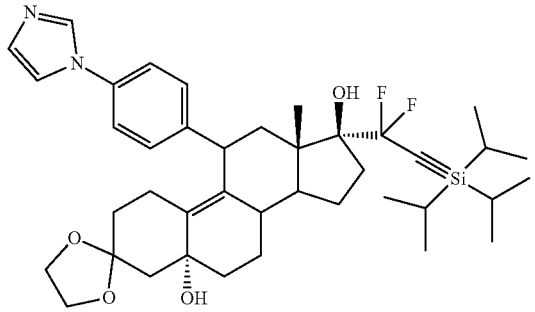

5c 3,3-Ethylendioxy-17α-[1,1-difluoro-3-[tris(1-methyl-ethyl)silyl]-2-propyn-1-yl]-5α-hidroxy-11β-[4-p-(1,3-imidazolyl)phenyl]estra-9-ene(5c)

Following the procedure described for compound 6a, 1 g of compound 4c (2.1 mmol) was reacted with 3.3 g of 3-bromo-3,3-difluoro-1-triisopropylsilylpropyne (10.5 mmol) and 4.3 mL of 2.5M solution of n-BuLi to afford 300 mg of 5c as a brown oil, yield: 21%. RE 0.61 (7:3, EtAc:Acetone). UV (nm): 200, 244. FT IR (ATR, cm$^{-1}$): 3517, 2938, 1519, 1456.

$^1$H NMR (CDCl$_3$, 300 MHz) δ 0.56 (s, 3H, H-18), 1.01 (s, 3H, Si(C$\underline{H}$)$_3$(CH$_3$)$_6$), 1.11 (s, 18H, Si(CH)$_3$(C$\underline{H}_3$)$_6$), 3.8 (s, 1H, —OH), 3.9 (m, 4H, ketal), 4.2 (s, 1H, —OH), 4.3 (d, J=6.3 Hz, H-11), 7.3 (m, 6H, H—Ar), 7.83 (s, 1H, H—Ar).

$^{13}$C NMR (CDCl$_3$, 75 MHz) δ 16.48 (C-18), 18.50 (Si(CH)$_3$(C$\underline{H}_3$)$_6$), 23.25 (Si(C$\underline{H}$)$_3$(CH$_3$)$_6$), 64.04 (ketal), 64.66 (ketal), 69.78 (C-5), 86.5 (t, J=24 Hz, (CF$_2$CC)), 108.51 (C-3), 121.11 (C—Ar), 128.50 (C—Ar), 132.61 (C-10), 134.82 (C—Ar), 135.18 (C-9), 146.71 (C—Ar).

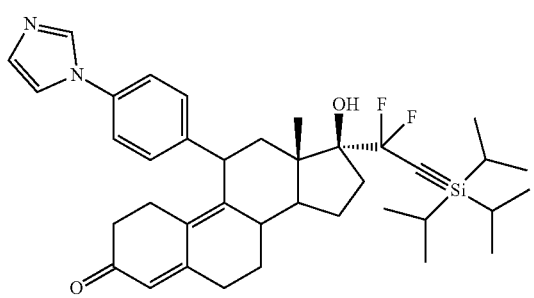

6c 3,3-Ethylendioxy-17α-[1,1-difluoro-3-[tris(1-methyl-ethyl)silyl]-2-propyn-1-yl]-5α-hydroxy-11β[4-p-(1,3-imidazolyl)phenyl]estra-2,9-dien-3-one.(6c)

225 mg of compound 5c was dissolved in 5 mL of methanol and cooled to −10° C. A 4N solution of HCl (0.32 mL, 1.3 mmol) was added dropwise. The mixture was stirred at room temperature for 1 hr. The reaction was quenched by the careful addition of saturated sodium bicarbonate solution and extracted with ethyl acetate. Combined organic layers were washed with water, brine and dried over anhydrous sodium sulfate. The crude was purified by column chromatography to get 210 mg of 6c as a yellow powder (quantitative yield), mp 127-129° C. R$_f$: 0.43 (5:5, EtAc:Acetone).

UV (nm): 200, 244. FT IR (ATR, cm$^{-1}$): 3116, 2947, 2852, 1651. NMR (CDCl$_3$, 300 MHz) δ 0.57 (s, 3H, H-18), 1.02 (s, 3H, Si(CH)$_3$(C$\underline{H}_3$)$_6$), 1.09 (s, 18H, Si(CH)$_3$(CH$_3$)$_6$), 4.45 (d, J=5.7 Hz, H-11), 5.7 (s, 1H, H-5), 7.27 (m, 6H, H—Ar), 7.82 (s, 1H, H—Ar).

$^{13}$C NMR (CDCl$_3$, 75 MHz) δ $^{13}$C NMR (CDCl$_3$, 75 MHz) δ 16.63 (C-18), 18.87 (Si(CH)$_3$(C$\underline{H}_3$)$_6$), 24.46 (Si(C$\underline{H}$)$_3$(CH$_3$)$_6$), 60.36 (CF$_2$CC), 76.3 (CF$_2$C$\underline{C}$), 86.22 (t, J=24 Hz, (CF$_2$CC)), 118.17 (C-17), 121.54 (C—Ar), 123.35 (C-4), 128.30 (C—Ar), 130.04 (C-10), 130.17 (C—Ar), 135.10 (C—Ar), 135.44 (C—Ar), 143.98 (C-9), 144.26 (C—Ar), 155.96 (C-5), 199.05 (C-3).

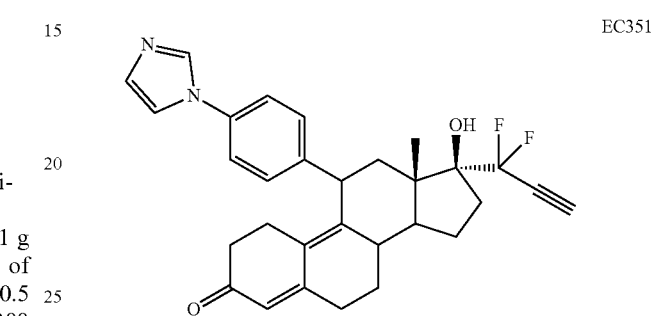

EC351

3,3-Ethylendioxy-17α-(1,1-difluoro-2-propyn-1-yl)-5α-hydroxy-11β-[4-p-(1,3-imidazolyl)phenyl]estra-2,9-dien-3-one (EC351)

Following the procedure described for EC330, 180 mg of compound 6c (0.28 mmol) was treated with 0.56 mL of a 1M solution of TBAF to obtain 70 mg of EC351 as a beige powder. (yield: 51%), mp 175-178° C. RE 0.42 (5:5, EtOAc:Acetone). UV (nm): 200, 242, 302. FT IR (ATR, cm$^{-1}$): 3230, 2947, 2117, 1651, 1523.

$^{-1}$H NMR (CDCl$_3$, 300 MHz) δ 0.65 (s, 3H, H-18), 2.89 (t, J=5.4 Hz, 1H, acetylenic hydrogen), 4.49 (d, J=5.7 Hz, H-11), 5.8 (s, 1H, H-5), 7.27 (m, 6H, H—Ar), 7.82 (s, 1H, H—Ar).

$^{13}$C NMR (CDCl$_3$, 75 MHz) δ 16.83 (C-18), 59.1 (CF$_2$CC), 76.16 (CF$_2$C$\underline{C}$), 85.73 (t, J=24 Hz, (CF$_2$CC)), 118.1 (C-17), 121.57 (C—Ar), 123.44 (C-4), 128.34 (C—Ar), 130.14 (C-10), 130.28 (C—Ar), 135.14 (C—Ar), 143.9 (C-9), 144.25 (C—Ar), 155.92 (C-5), 199.13 (C-3).

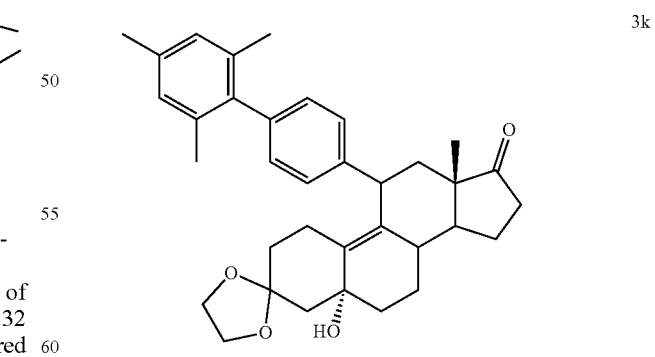

3k 3,3-Ethylendioxy-5α-hidroxy-11β-[4-p-(2,4,6-trimethyl-phenyl)phenyl]estra-9-en-17-one (3k)

Compound 3c (5.8 g, 10.8 mmol), 2,4,6-trimethylphenyl-boronic acid (2.6 g, 16.2 mmol), Pd(dppfCl$_2$) (394 mg, 0.54 mmol) and potassium carbonate (2.2 g, 16.2 mmol) were introduced in a flask fitted with a condenser and the system was connected to nitrogen-vacuum inlet; dioxane (120 mL) and water (12 mL) were added and the flask was evacuated and backfilled with nitrogen 7-10 times. The flask was immersed in a pre-heated oil bath at 100° C. and refluxed overnight. The TLC showed complete conversion of the starting material to the product. The reaction was cooled in an ice bath and water was added, the reaction was extracted with ethyl acetate and the organic layer was washed with water and brine and dried over sodium sulfate. The crude was purified by column chromatography using 50% ethyl acetate in hexane to get 4.61 g of 3k as a white powder (81% yield), mp 126-128° C. $R_f$:0.37 (5:5, Hex:EtOAc). UV (nm): 204. FT IR (ATR, cm$^{-1}$): 3520, 2920, 2866, 1732, 1618.

$^1$H NMR (CDCl$_3$, 300 MHz) δ 0.53 (s, 3H, H-18), 1.95 (s, 6H, Ar—C$\underline{H}$), 2.32 (s, 3H, Ar—C$\underline{H}$), 3.9 (m, 4H, ketal), 4.39 (s, 1H, H-11), 6.92 (s, 2H, H—Ar), 7.01 (d, J=8.1 Hz, 2H, H—Ar), 7.26 (d, J=5.4 Hz, 2H, H—Ar).

$^{13}$C NMR (CDCl$_3$, 75 MHz) δ 13.98 (C-18), 22.12 (Ar—$\underline{C}$H$_3$), 23.36 (Ar—$\underline{C}$H$_3$), 23.39 (Ar—$\underline{C}$H$_3$), 64.07 (ketal), 64.65 (ketal), 70.02 (C-5), 108.68 (C-3), 127.17 (C—Ar), 127.92 (C—Ar), 127.96 (C—Ar), 129.15 (C—Ar), 133.65 (C-10), 135.23(C—Ar), 135.99 (C—Ar), 136.42 (C—Ar), 138.32 (C—Ar), 138.74 (C—Ar), 144.49 (C-9), 219.85 (C-17).

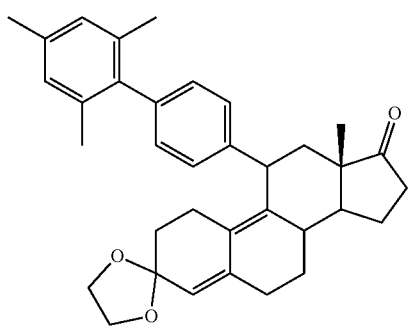

4k 3,3-Ethylendioxy-11β-[4-p-(2,4,6-trimethylphenyl)phenyl]estra-4,9-dien-17-one (4k)

The synthesis of compound 4k was done following the procedure described for the synthesis of 4a where 4.96 g of 3k (9.4 mmol) was treated with 5 mL of acetic anhydride (47 mmol), 114.8 mg of DMAP (0.94 mmol) and 50 mL of pyridine, to get 4 g of 4k as a white powder (84% yield), mp 201-203° C. $R_f$: 0.57 (5:5, Hex:EtOAc). UV (nm): 200, 249. FT IR (ATR, cm$^{-1}$): 2920, 2852, 1739, 1631.

$^1$H NMR (CDCl$_3$, 300 MHz) δ 0.54 (s, 3H, H-18), 1.95 (s, 6H, Ar—C$\underline{H}_3$), 2.32 (s, 3H, Ar—C$\underline{H}_3$), 3.9 (m, 4H, ketal), 4.42 (d, J=6.9 Hz, 1H, H-11), 5.40 (s, 1H, H-4), 6.92 (s, 2H, H—Ar), 7.01 (d, J=8.1 Hz, 2H, H—Ar), 7.26 (d, J=5.4 Hz, 2H, H—Ar).

$^{13}$C NMR (CDCl$_3$, 75 MHz) δ 14.17 (C-18), 21.00 (Ar—$\underline{C}$H$_3$), 24.32 (Ar—$\underline{C}$H$_3$), 25.79 (Ar—$\underline{C}$H$_3$), 64.07 (ketal), 64.65 (ketal), 107.42 (C-3), 122.98 (C-4), 126.5 (C—Ar), 126.7 (C—Ar), 128.94 (C—Ar), 129.58 (C-10), 136.82 (C—Ar), 137.15 (C—Ar), 142.85 (C—Ar), 144.95 (C—Ar), 145.0 (C—Ar), 145.13 (C-9), 199.36 (C-17).

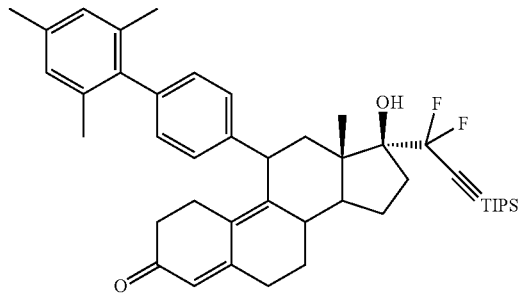

6k

17α-[1,1-difluoro-3-[tris(1-methylethyl)silyl]-2-propyn-1-yl]-17β-hydroxy-11β-[4-p-(2,4,6-trimethylphenyl) phenyl]estra-4,9-dien-3-one (6k)

This reaction was done following the same procedure described for the synthesis of compound 6a where 3.9 g of compound 6k (7.6 mmol) was treated with 9.4 g of 3-bromo-3,3-difluoro-1-triisopropylsilylpropyne (30.4 mmol), and 15.2 mL of a 2M solution of n-BuLi (38 mmol). The crude 5k obtained was hydrolyzed with 5.7 mL (22.8 mmol) of a 4N solution of HCl to afford 4.1 g of 6k as a beige powder, yield: 79%, mp 112-115° C. $R_f$: 0.77 (5:5, Hex:EtOAc). UV (nm): 200, 231, 312. FT IR (ATR, cm$^{-1}$): 3385, 2947, 2852, 1658, 1597.

$^1$H NMR (CDCl$_3$, 300 MHz) δ 0.65 (s, 3H, H-18), 1.04 (s, 3H, Si(C$\underline{H}$)$_3$(CH$_3$)$_6$), 1.05 (s, 18H, Si(CH)$_3$(C$\underline{H}_3$)$_6$), 1.96 (s, 6H, Ar—C$\underline{H}_3$), 2.32 (s, 3H, Ar—C$\underline{H}_3$), 4.48 (s, 1H, H-11), 5.78 (s, 1H, H-4), 6.92 (s, 2H, H—Ar), 7.01 (d, J=8.1 Hz, 2H, H—Ar), 7.2 (d, J=7.8 Hz, 2H, H—Ar).

$^{13}$C NMR (CDCl$_3$, 75 MHz) δ 10.94 (C-18), 18.53 (Si(CH)$_3$($\underline{C}$H$_3$)$_6$), 20.99 (Ar—$\underline{C}$H$_3$), 21.32 (—CCH$_2$CH$_3$), 24.45 (Si($\underline{C}$H)$_3$(CH$_3$)$_6$), 25.79 (Ar—$\underline{C}$H$_3$), 27.72 (Ar—$\underline{C}$H$_3$), 86.4 (t, J=23 Hz, ($\underline{C}$F$_2$CC)), 122.98 (C-4), 126.87 (C—Ar), 128.0 (C—Ar), 129.40 (C—Ar), 129.61 (C-10), 135.98 (C—Ar), 136.5 (C—Ar), 138.48 (C—Ar), 138.63 (C—Ar), 142.63 (C—Ar), 145.21 (C-9), 156.54 (C-5), 199.46 (C-3).

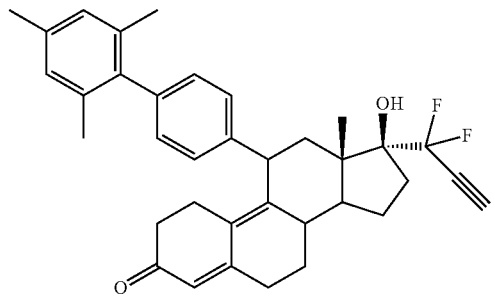

EC359

17α-(1,1-difluoro-2-propyn-1-yl)-17β-hydroxy-11β-[4-p-(2,4,6-trimethylphenyl) phenyl]estra-4,9-dien-3-one (EC359)

Following the same procedure reported for EC330, 4.1 g of compound 6k (5.8 mmol) was treated with 8.7 mL of a 1M solution of TBAF to get 1.62 g of EC359 as a white powder, yield: 52%, mp 255-256° C. $R_f$:0.33 (5:5, Hex: EtOAc). UV (nm): 300. FT IR (ATR, cm$^{-1}$): 3305, 2947, 2873, 2130, 1638.

¹H NMR (CDCl₃, 300 MHz) δ 0.65 (s, 3H, H-18), 1.96 (s, 6H, Ar—CH₃), 2.32 (s, 3H, Ar—CH₃), 2.9 (t, J=5.4 Hz, 1H, acetylenic hydrogen), 4.52 (d, J=6.9 Hz, 1H, H-11), 5.78 (s, 1H, H-4), 6.93 (s, 2H, H—Ar), 7.05 (d, J=8.4 Hz, 2H, H—Ar), 7.23 (d, J=8.1 Hz, 2H, H—Ar).

¹³C NMR (CDCl₃, 75 MHz) δ 16.40 (C-18), 20.61 (Ar—CH₃), 25.84 (Ar—CH₃), 27.69 (Ar—CH₃), 85.92 (t, J=23 Hz, (CF₂CC)), 123.08 (C-4), 126.87 (C—Ar), 128.0 (C—Ar), 129.43 (C—Ar), 129.70 (C-10), 135.99 (C—Ar), 136.54 (C—Ar), 138.53 (C—Ar), 138.61 (C—Ar), 142.51 (C—Ar), 145.04 (C-9), 156.45 (C-5), 199.52 (C-3).

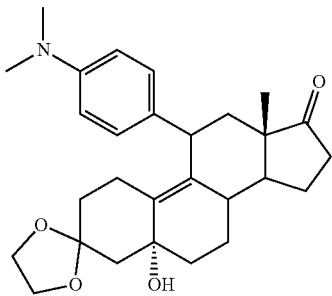

3,3-Ethylendioxy-5α-hidroxy-11β-[4-p-(dimethylamino)phenyl]estra-9-en-17-one (3d)

Following the procedure described for compound 3a, 4 g of compound 2 (12.1 mmol) was reacted with 1.75 g of Mg (72.6 mmol), 12 g of 4-Br—N,N-dimethylanilin (60.4 mmol) and 600 mg of CuCl (6.04 mmol) to afford 3d as a white powder (5 g), yield: 93%, mp 116-118° C. $R_f$: 0.28 (5:5, Hex:EtOAc). UV (nm): 201, 259, 302. FT IR (ATR, cm⁻¹): 3507, 2927, 2873, 1749, 1604.

¹H NMR (CDCl₃, 300 MHz) δ 0.51 (s, 3H, H-18), 2.90 (s, 6H, —N(CH₃)₂), 3.9 (m, 4H, ketal), 4.2 (d, J=6.3 Hz, H-11), 4.3 (s, 1H, —OH), 6.65 (d, J=8.7 Hz, 2H, H—Ar), 7.07 (d, J=8.4 Hz, 2H, H—Ar).

¹³C NMR (CDCl₃, 75 MHz) δ 14.26 (C-18), 64.02 (ketal), 64.63 (ketal), 70.03 (C-5), 108.73 (C-3), 112.60 (C—Ar), 127.61 (C—Ar), 133.57 (C-10), 134.08 (C—Ar), 134.65 (C-9), 148.44 (C—Ar), 220.17 (C-17).

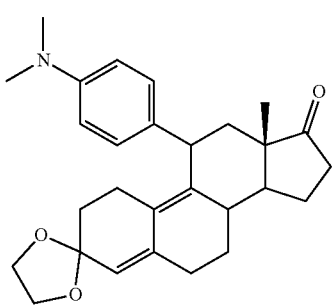

3,3-Ethylendioxy-11β-[4-p-(dimethylamino)phenyl]estra-4,9-dien-17-one (4d)

The synthesis of compound 4d was done following the procedure described for compound 4a where 4.55 g of 3d (10 mmol) was reacted with 4.8 mL of acetic anhydride (50 mmol), 122.1 mg of DMAP (1 mmol) and 30 mL of pyridine, to get 2.76 g of a beige powder of 4d (64% yield), mp 125-127° C. $R_f$: 0.6 (5:5, Hex:EtOAc). UV (nm): 202, 255. FT IR (ATR, cm⁻¹): 2906, 1739, 1620.

¹H NMR (CDCl₃, 300 MHz) δ 0.53 (s, 3H, H-18), 2.93 (s, 6H, —N(CH₃)₂), 3.9 (m, 4H, ketal), 4.2 (d, J=6.3 Hz, 1H, H-11), 6.37 (s, 1H, H-4), 6.64 (d, J=8.7 Hz, 2H, H—Ar), 7.07 (d, J=8.4 Hz, 2H, H—Ar).

¹³C NMR (CDCl₃, 75 MHz) δ 14.16 (C-18), 64.34 (ketal), 64.51 (ketal), 106.20 (C-3), 112.60 (C—Ar), 121.52 (C-4), 127.61 (C—Ar), 129.79 (C—Ar), 132.40 (C-10), 138.15 (C-9), 139.49 (C-5), 148.49 (C—Ar), 219.95 (C-17).

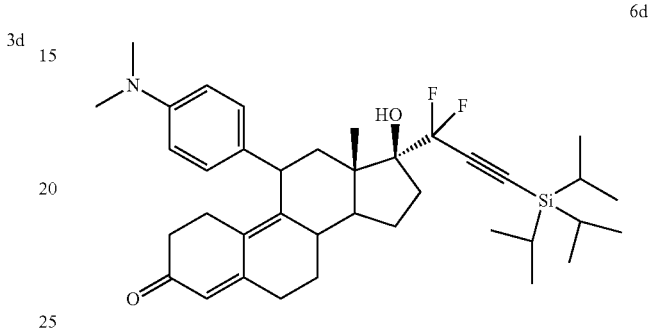

17α-[1,1-difluoro-3-[tris(1-methylethyl)silyl]-2-propyn-1-yl]-17β-hydroxy-11β-[4-p-(dimethylamino) phenyl]estra-4,9-dien-3-one (6d)

Following the same procedure described for the syntheses of compound 5a, 0.5 g of compound 4d (1.15 mmol) was treated with 1.7 g of 3-bromo-3,3-difluoro-1-triisopropylsilylpropyne (5.75 mmol), and 2.3 mL (5.75 mmol) of a 2M solution of n-BuLi. The crude obtained was hydrolysed with 0.3 mL (1.5 mmol) of a 4N solution of HCl to afford 6d as a brown powder, yield: 63%, mp 113-116° C. $R_f$: 0.52 (7:3, Hex:EtOAc). FT IR (ATR, cm⁻¹): 3399, 2947, 2866, 1658, 1608.

¹H NMR (CDCl₃, 300 MHz) δ 0.64 (s, 3H, H-18), 1.03 (s, 3H, Si(CC)₃(CH₃)₆), 1.08 (s, 18H, Si(CH₃)₃(CH₃)₆), 2.91 (s, 6H, —N(CH₃)₂), 4.34 (s, 1H, H-4), 5.75 (s, 1H, H-4), 6.66 (d, J=9 Hz, 2H, H—Ar), 7.01 (d, J=8.7 Hz, 2H, H—Ar).

¹³C NMR (CDCl₃, 75 MHz) δ 16.38 (C-18), 18.51 (Si(CH₃)₃(CH₃)₆), 24.40 (Si(CH)₃(CH₃)₆), 86.30 (t, J=21 Hz, (CF₂CC)), 102.20 (C-17), 112.76 (C—Ar), 122.75 (C-4), 127.43 (C—Ar), 129.22 (C—Ar), 131.89 (C-10), 145.84 (C-9), 148.55 (C—Ar), 156.63 (C-5), 199.54 (C-3).

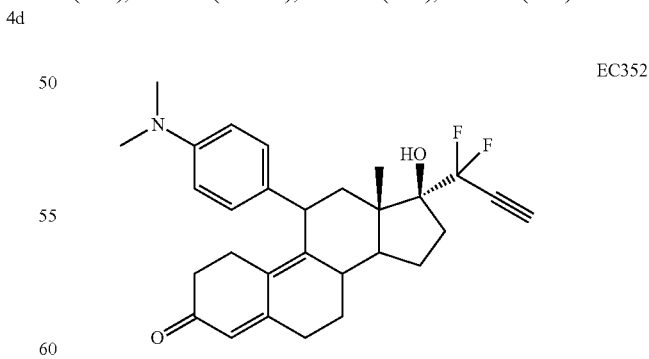

17α-(1,1-difluoro-2-propyn-1-yl)-17β-hydroxy-11β-[4-p-(dimethylamino) phenyl]estra-4,9-dien-3-one (EC352)

The reaction was done following the same procedure described for EC330 where 80 mg of compound 5d (0.128 mmol) was treated with 0.15 mL of a 1M solution of TBAF to get 60 mg of EC352 as a yellow powder (yield 99%), mp 138-140° C. R$_f$:0.15 (7:3, Hex:EtOAc). UV (nm): 203, 259, 301. FT IR (ATR, cm$^{-1}$): 3999, 3284, 2130, 1645, 1604.

$^1$H NMR (CDCl$_3$, 300 MHz) δ 0.64 (s, 3H, H-18), 2.89 (t, J=5.4 Hz, 1H, acetylenic hydrogen), 2.91 (s, 6H, —N(CH$_3$)$_2$), 4.37 (d, J=6.3 Hz, 1H, H-11), 5.29 (s, 1H, H-4), 5.75 (s, 1H, H-4), 6.67 (d, J=8.7 Hz, 2H, H—Ar), 7.02 (d, J=8.7 Hz, 2H, H—Ar).

$^{13}$C NMR (CDCl$_3$, 75 MHz) δ 16.53 (C-18), 85.86 (t, J=24 Hz, (CF$_2$CC)), 112.78 (C—Ar), 122.81 (C-4), 127.37 (C—Ar), 129.29 (C—Ar), 131.86 (C-10), 145.78 (C-9), 148.55 (C—Ar), 156.64 (C-5), 199.63 (C-3).

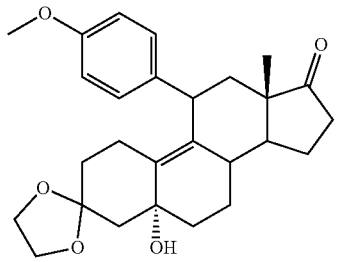

3e 3,3-Ethylendioxy-5α-hidroxy-11β-[4-p-(methoxy)phenyl]estra-9-en-17-one (3e)

This compound was synthesized following the procedure described for compound 3a, where 3 g of compound 2 (9 mmol) was reacted with 1.3 g of Mg (54 mmol), 8.4 g of 4-Br-anisole (45 mmol) and 445 mg of CuCl (4.5 mmol) to afford 3e as a white powder (3.81 g), yield: 97%, mp 104-108° C. R.f: 0.22 (5:5, Hex:EtOAc). UV (nm): 200,230. FT IR (ATR, cm$^{-1}$): 3507, 2927, 2879, 1739, 1611.

—$^1$H NMR (CDCl$_3$, 300 MHz) δ 0.49 (s, 3H, H-18), 3.77 (s, 3H, —OCH$_3$), 3.9 (m, 4H, ketal), 4.28 (d, J=6.9 Hz, H-11), 4.37 (s, 1H, —OH), 6.8 (d, J=9 Hz, 2H, H—Ar), 7.1 (d, J=8.7 Hz, 2H, H—Ar).

$^{13}$C NMR (CDCl$_3$, 75 MHz) δ 14.37 (C-18), 64.0 (ketal), 64.6 (ketal), 70.1 (C-5), 112.3 (C-3), 114.01 (C—Ar), 130.02 (C—Ar), 133.5 (C-10), 135.76 (C—Ar), 134.6 (C-9), 157.71 (C—Ar), 218.99 (C-17).

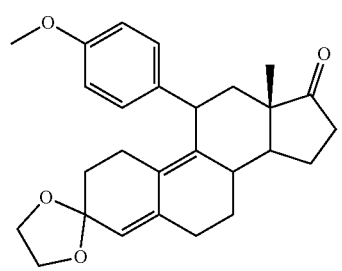

4e 3,3-Ethylendioxy-11β-[4-p-(methoxy)phenyl]estra-4,9-dien-17-one (4e)

The synthesis of compound 4e was done following the procedure described for compound 4a where 3.7 g of 3e (8.4 mmol) was heated at 70° C. with 4.8 mL of acetic anhydride (45.5 mmol), 111.2 mg of DMAP (0.91 mmol) and 40 mL of pyridine, to get 1.6 g of 4e as a white powder (45% yield), mp 107-110° C. RE 0.63 (5:5, Hex:EtOAc). UV (nm): 200, 250. FT IR (ATR, cm$^{-1}$): 2940, 2866, 1732, 1604.

$^1$H NMR (CDCl$_3$, 300 MHz) δ 0.51 (s, 3H, H-18), 3.76 (s, 3H, —OCH$_3$), 3.9 (m, 4H, ketal), 4.12 (d, J=6.9 Hz, H-11), 5.38 (s, 1H, H-4), 6.77 (d, J=8.7 Hz, 2H, H—Ar), 7.13 (d, J=8.7 Hz, 2H, H—Ar).

$^{13}$C NMR (CDCl$_3$, 75 MHz) δ 14.37 (C-18), 55.17 (—OCH$_3$), 64.0 (ketal), 64.6 (ketal), 114.02 (C-3), 123.34 (C-4), 130.02 (C-10), 135.76 (C—Ar), 144.99 (C-9), 156.01 (C—Ar), 157.71 (C—Ar), 218.96 (C-17).

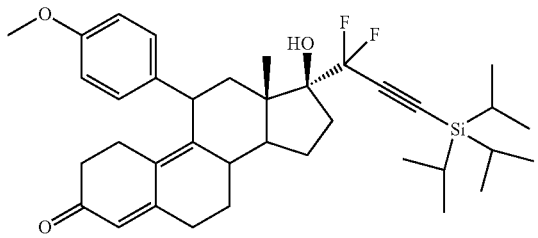

6e

17α-[1,1-difluoro-3-[tris(1-methylethyl)silyl]-2-propyn-1-yl]-17β-hydroxy-11β-[4-p-(methoxy)phenyl]estra-4,9-dien-3-one (6e)

Following the same procedure described for 5a, 1.4 g of compound 4e (3.3 mmol) was reacted with 4.1 g of 3-bromo-3,3-difluoro-1-triisopropylsilylpropyne (13.2 mmol), and 6.6 mL of a 2M solution of n-BuLi (16.5 mmol). The crude obtained was hydrolysed with 2.6 mL (10.6 mmol) of a 4N solution of HCl to get 1.25 g of 6e as a brown powder, yield: 98%, mp 99-102° C. R$_f$: 0.18 (9:1, Hex:EtOAc). UV (nm): 229, 300. FT IR (ATR, cm$^{-1}$): 3412, 2940, 2866, 1665, 1618.

$^1$H NMR (CDCl$_3$, 300 MHz) δ 0.60 (s, 3H, H-18), 1.03 (s, 3H, Si(CH$_3$)$_3$(CH$_3$)$_6$), 1.06 (s, 18H, Si(CH$_3$)$_3$(CH$_3$)$_6$), 3.77 (s, 3H, —OCH$_3$), 4.36 (d, J=6.9 Hz, H-11), 5.75 (s, 1H, H-4), 6.80 (d, 8.7 Hz, 2H, H—Ar), 7.06 (d, J=8.7 Hz, 2H, H—Ar).

$^{13}$C NMR (CDCl$_3$, 75 MHz) δ 10.91 (C-18), 18.51 (Si(CH$_3$)$_3$(CH$_3$)$_6$), 24.41 (Si(CH$_3$)$_3$(CH$_3$)$_6$), 55.1 (—OCH$_3$), 86.32 (t, J=21 Hz, (CF$_2$CC)), 113.89 (C—Ar), 122.93 (C-4), 127.72 (C—Ar), 129.48 (C-10), 136.30 (C—Ar), 145.31 (C-9), 156.47 (C-5), 157.53 (C—Ar), 199.42 (C-3).

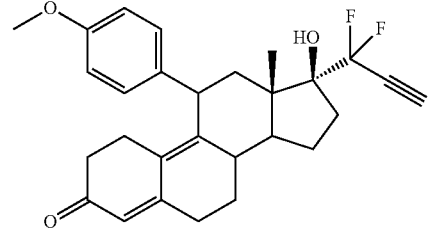

EC356

17α-(1,1-difluoro-2-propyn-1-yl)-17β-hydroxy-11β-[4-p-(methoxy)phenyl]estra-4,9-dien-3-one (EC356)

The reaction was done following the same procedure reported for EC330 where 1.2 g of compound 5e (1.97 mmol) was treated with 3 mL of a 1M solution of TBAF to get 530 mg of EC356 as a beige powder, yield: 60%, mp 173-174° C. R$_f$: 0.33 (5:5, Hex:EtOAc). UV (nm): 228, 303. FT IR (ATR, cm$^{-1}$): 3325, 3271, 2940, 2130, 1638, 1597.

$^1$H NMR (CDCl$_3$, 300 MHz) δ 0.61 (s, 3H, H-18), 2.89 (t, J=5.4 Hz, 1H, acetylenic hydrogen), 3.77 (s, 3H, —OCH$_3$), 4.3 (d, J=7.2 Hz, 1H, H-11), 5.76 (s, 1H, H-4), 6.8 (d, J=8.4 Hz, 2H, H—Ar), 7.06 (d, J=8.4 Hz, 2H, H—Ar).

$^{13}$C NMR (CDCl$_3$, 75 MHz) δ 16.55 (C-18), 55.1 (—OCH$_3$), 85.85 (t, J=24 Hz, (CF$_2$CC)), 113.89 (C—Ar), 123.04 (C-4), 127.74 (C—Ar), 129.57 (C-10), 136.47 (C—Ar), 145.12 (C-9), 156.35 (C-5), 157.56 (C—Ar), 199.44 (C-3).

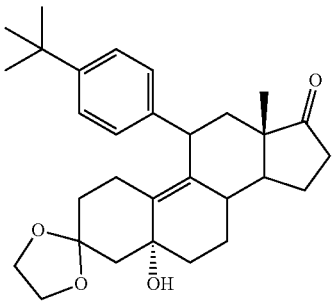

3,3-Ethylendioxy-5α-hidroxy-11β-[4-p-(t-butyl) phenyl]estra-9-en-17-one (3f)

1-tert-butyl-4-iodobenzene (3 g, 11.53 mmol) was dissolved in 25 mL of THF and cooled to −10° C. as a 2M solution of isopropyl magnesium chloride (7.9 mL, 15.72 mmol) was added dropwise over a period of 2-3 min. The resulting solution was stirred for 30 min. Solid CuCl (466 mg, 4.71 mmol) was added and stirred for another 30 min at 0° C. A solution of the epoxide 2 (2.5 g, 7.56 mmol) in 20 mL of THF was added dropwise and the flask was taken out of the cooling bath after 15 min and allowed to stir for 1 hr at room temperature. The TLC showed complete conversion of starting material to product. The reaction was quenched by adding sat NH$_4$Cl, extracted with ethyl acetate and washed with water and brine. The organic layer was dried over sodium sulfate and evaporated under vacuum to get the crude. The crude was purified by column chromatography using 60% ethyl acetate in hexane to get 2.91 g of 3f as a white powder (83% yield), mp 94-96° C. UV (nm): 200,230. R$_f$: 0.4 (5:5, Hex:EtOAc). FT IR (ATR, cm$^{-1}$): 3514, 2947, 2873, 1736.

$^1$H NMR (CDCl$_3$, 300 MHz) δ 0.46 (s, 3H, H-18), 1.27 (s, 9H, —C(CH$_3$)$_3$), 3.9 (m, 4H, ketal), 4.27 (d, J=6.9 Hz, H-11), 7.13 (d, J=8.4 Hz, 2H, H—Ar), 7.22 (d, J=8.7 Hz, 2H, H—Ar).

$^{13}$C NMR (CDCl$_3$, 75 MHz) δ 14.4 (C-18), 63.69 (ketal), 64.0 (ketal), 108.73 (C-3), 123.25 (C—Ar), 126.43 (C—Ar), 140.47 (C-10), 145.15 (C—Ar), 148.88 (C—Ar), 219.03 (C-17).

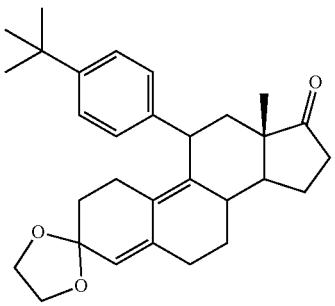

3,3-Ethylendioxy-11β-[4-p-(t-butyl)phenyl]estra-4,9-dien-17-one (4f)

The synthesis of compound 4f was accomplished following the procedure described 4a where 2.8 g of 3f (6 mmol) was heated at 70° C. with 3.2 mL of acetic anhydride (30 mmol), 73.3 mg of DMAP (0.6 mmol) and 30 mL of pyridine, to get 1.7 g of 4f as a white powder (65% yield), mp 85-88° C. R$_f$:0.72 (5:5, Hex:EtOAc). UV (nm): 200, 250. FT IR (ATR, cm$^{-1}$): 2947, 2873, 1732, 1631.

$^1$H NMR (CDCl$_3$, 300 MHz) δ 0.52 (s, 3H, H-18), 1.28 (s, 9H, —C(CH$_3$)$_3$), 3.9 (m, 4H, ketal), 4.3 (d, J=6.9 Hz, H-11), 5.78 (s, 1H, H-4), 7.1 (d, J=8.4 Hz, 2H, H—Ar), 7.28 (d, J=8.7 Hz, 2H, H—Ar). $^{13}$C NMR (CDCl$_3$, 75 MHz) M4.42 (C-18), 31.29 (—C(CH$_3$)$_3$), 34.26 (—C(CH$_3$)$_3$), 64.1 (ketal), 64.16 (ketal), 107.95 (C-3), 122.49 (C-4), 123.26 (C—Ar), 124.67 (C—Ar), 125.49 (C—Ar), 126.42 (C—Ar), 130.81 (C-10), 140.47 (C-5), 141.94 (C-9), 145.09 (C—Ar), 148.86 (C—Ar), 218.93 (C-17).

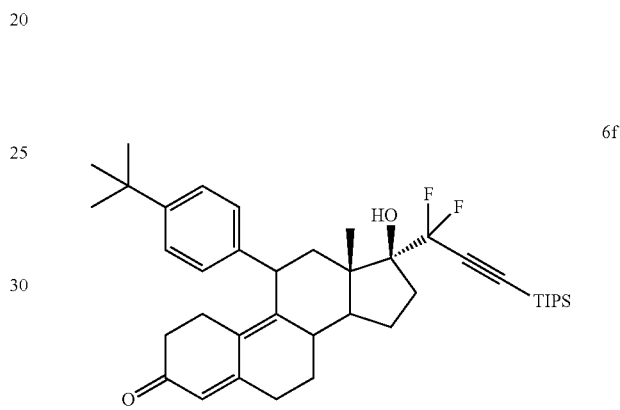

17α-[1,1-difluoro-3-[tris(1-methylethyl)silyl]-2-propyn-1-yl]-17β-hydroxy-11β-[4-p-(t-butyl) phenyl]estra-4,9-dien-3-one (6f)

This reaction was done following the same procedure described for 6a where 1.6 g of compound 4f (3.5 mmol) was reacted with 4.3 g of 3-bromo-3,3-difluoro-1-triisopropylsilylpropyne (14 mmol), and 7 mL of a 2M solution of n-BuLi (17.5 mmol). The crude obtained was hydrolysed with 2.6 mL (10.5 mmol) of a 4N solution of HCl to get 1.87 g of 6f as a brown powder, yield: 85%, mp 89-91° C. UV (nm): 222, 296. R$_f$:0.72 (5:5, Hex:EtOAc). FT IR (ATR, cm$^{-1}$): 3392, 2940, 2859, 1651.

$^1$H NMR (CDCl$_3$, 300 MHz) δ 0.59 (s, 3H, H-18), 1.08 (s, 3H, Si(CH)$_3$(CH$_3$)$_6$), 1.1 (s, 18H, Si(CH)$_3$(CH$_3$)$_6$), 1.28 (s, 9H, —C(CH$_3$)$_3$), 4.38 (d, J=6.9 Hz, H-11), 5.76 (s, 1H, H-4), 7.08 (d, J=8.4 Hz, 2H, H—Ar), 7.26 (d, J=8.7 Hz, 2H, H—Ar).

$^{13}$C NMR (CDCl$_3$, 75 MHz) δ 16.47 (C-18), 18.51 (Si(CH)$_3$(CH$_3$)$_6$), 24.39 (Si(CH)$_3$(CH$_3$)$_6$), 31.17 (—C(CH$_3$)$_3$), 34.25(—C(CH$_3$)$_3$), 86.34 (t, J=23 Hz, (CF$_2$CC)), 122.86 (C-4), 125.36 (C—Ar), 126.35 (C—Ar), 129.42 (C-10), 140.98 (C—Ar), 145.39 (C-9), 148.56 (C—Ar), 156.55 (C-5), 199.48 (C-3).

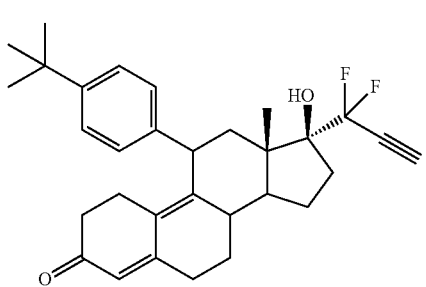 [SMILES: C#CC(F)(F)[C@]1(O)CCC2C3CCC4=CC(=O)CCC4=C3C(c3ccc(C(=C)C)cc3)C[C@@]21C]

EC357

17α-(1,1-difluoro-2-propyn-1-yl)-17β-hydroxy-11β-[4-p-(t-butyl)phenyl]estra-4,9-dien-3-one (EC357)

Following the procedure reported for EC330, 1.8 g of compound 6f (2.8 mmol) was treated with 4.5 mL of a 1M solution of TBAF to get 420 mg of EC357 as a beige powder (yield: 32%), mp 127-129° C. $R_f$ 0.43 (5:5, Hex:EtOAc). UV (nm): 222, 301. FT IR (ATR, cm$^{-1}$): 3406, 3271, 2947, 2866, 2130, 1651, 1597.

$^1$H NMR (CDCl$_3$, 300 MHz) δ 0.60 (s, 3H, H-18), 1.28 (s, 9H, —C(CH$_3$)$_3$), 2.90 (t, J=5.1 Hz, 1H, acetylenic hydrogen), 4.42 (d, J=6.9 Hz, H-11), 5.76 (s, 1H, H-4), 7.09 (d, J=8.1 Hz, 2H, H—Ar), 7.26 (d, J=7.2 Hz, 2H, H—Ar). $^{13}$C NMR (CDCl$_3$, 75 MHz) δ 16.63 (C-18), 31.33 (—C(CH$_3$)$_3$), 34.26 (—C(CH$_3$)$_3$), 85.86 (t, J=25 Hz, (CF$_2$CC)), 122.97 (C-4), 125.38 (C—Ar), 126.38 (C—Ar), 129.52 (C-10), 140.93 (C—Ar), 145.21 (C-9), 148.62 (C—Ar), 156.46 (C-5), 199.53 (C-3).

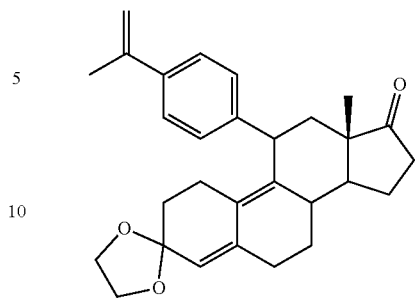

4g

3,3-Ethylendioxy-11β-[4-p-(1-methylethenyl)phenyl]estra-4,9-dien-17-one (4g)

The synthesis of compound 4g was accomplished following the procedure described 4a where 3.2 g of 4f (7.1 mmol) was heated at 70° C. with 3.78 mL of acetic anhydride (36 mmol), 87 mg of DMAP (0.7 mmol) and 35 mL of pyridine, to get 2.4 g of 4 g as a white powder (80% yield), mp 89-91° C. $R_f$ 0.57 (5:5, Hex:EtOAc). UV (nm): 203, 251. FT IR (ATR, cm$^{-1}$): 2927, 2879, 1739, 1631.

$^1$H NMR (CDCl$_3$, 300 MHz) δ 0.51 (s, 3H, H-18), 2.12 (s, 3H, —CCH$_2$CH$_3$), 3.9 (m, 4H, ketal), 4.3 (d, J=6.9 Hz, H-11), 5.04 (s, 1H, —CCH$_2$CH$_3$), 5.36 (s, 1H, —CCH$_2$CH$_3$), 5.39 (s, 1H, H-4), 7.19 (d, J=8.4 Hz, 2H, H—Ar), 7.38 (d, J=8.1 Hz, 2H, H—Ar).

$^{13}$C NMR (CDCl$_3$, 75 MHz) δ 14.44 (C-18), 21.91 (—CCH$_2$CH$_3$), 64.40 (ketal), 64.55 (ketal), 106.09 (C-3), 111.76 (—CCH$_2$CH$_3$), 121.92 (C-4), 125.42 (C—Ar), 125.47 (C—Ar), 126.97 (C—Ar), 130.28 (C-10), 137.36 (C—Ar), 138.27 (C-5), 139.25 (C-9), 142.62 (—CCH$_2$CH$_3$), 144.15 (C—Ar), 219.65 (C-17).

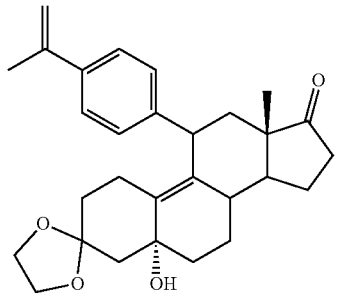

3g

3,3-Ethylendioxy-5α-hidroxy-11β-[4-p-(1-methylethenyl)phenyl]estra-9-en-17-one (3g)

Compound 3g was synthesized following the same procedure described for compound 3a, using 3 g of compound 2 (9 mmol), 875 g of Mg (36.4 mmol), 6 g of 4-bromoisopropenylbenzene (30.4 mmol) dissolved in 20 mL of THF and 300 mg of CuCl (3 mmol). The product was white powder (3.3 g), yield: 83%, mp 98-101° C. $R_f$ 0.31 (5:5, Hex:EtOAc). UV (nm): 201, 254. FT IR (ATR, cm$^{-1}$): 3500, 2933, 2866, 1739, 1624.

$^1$H NMR (CDCl$_3$, 300 MHz) δ 0.49 (s, 3H, H-18), 2.12 (s, 3H, —CCH$_2$CH$_3$), 3.9 (m, 4H, ketal), 4.3 (d, J=7.2 Hz, H-11), 4.37 (s, 1H, —OH), 5.04 (s, 1H, —CCH$_2$CH$_3$), 5.37 (s, 1H, —CCH$_2$CH$_3$), 7.19 (d, J=8.4 Hz, 2H, H—Ar), 7.38 (d, J=6.6 Hz, 2H, H—Ar).

$^{13}$C NMR (CDCl$_3$, 75 MHz) δ 14.30 (C-18), 64.02 (ketal), 64.65 (ketal), 69.98 (C-5), 108.59 (C-3), 111.74 (—CCH$_2$CH$_3$), 125.32 (C—Ar), 126.91 (C—Ar), 133.43 (C-10), 135.24 (C—Ar), 138.15 (C-9), 142.52 (—CCH$_2$CH$_3$), 145.45 (C—Ar), 219.86 (C-17).

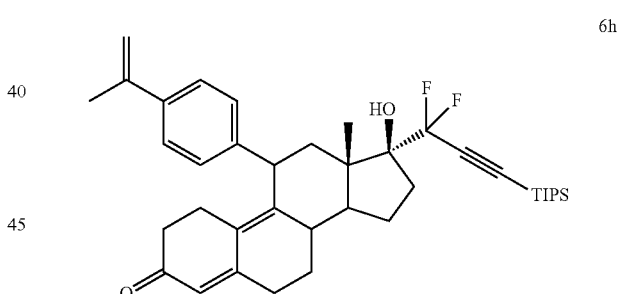

6h

17α-[1,1-difluoro-3-[tris(1-methylethyl)silyl]-2-propyn-1-yl]-17β-hydroxy-11β-[4-p-(1-methylethenyl) phenyl]estra-4,9-dien-3-one (6h)

This reaction was done following the same procedure described for the synthesis of compound 6a using 2.4 g of compound 4 g (5.6 mmol), 6.9 g of 3-bromo-3,3-difluoro-1-triisopropylsilylpropyne (22.4 mmol), and 13.3 mL of a 2M solution of n-BuLi (28 mmol). The crude obtained was hydrolyzed with 1.8 mL (7.2 mmol) of a 4N solution of HCl to get 450 mg of 6e as a brown powder, yield: 20%, mp 88-91° C. $R_f$ 0.77 (5:5, Hex:EtOAc). UV (nm): 202, 252, 296. FT IR (ATR, cm$^{-1}$): 3392, 2940, 2852, 1665, 1597.

$^1$H NMR (CDCl$_3$, 300 MHz) δ 0.61 (s, 3H, H-18), 1.03 (s, 3H, Si(CH)$_3$(CH$_3$)$_6$), 1.06 (s, 18H, Si(CH$_3$)$_3$(CH$_3$)$_6$), 2.13 (s, 3H, —CCH$_2$CH$_3$), 4.41 (s, 1H, H-11), 5.06 (s, 1H, —CCH$_2$CH$_3$), 5.37 (d, J=10.2 Hz, 1H, —CCH$_2$CH$_3$), 5.77 (s, 1H, H-4), 7.13 (d, J=8.1 Hz, 2H, H—Ar), 7.40 (d, J=8.4 Hz, 2H, H—Ar).

$^{13}$C NMR (CDCl$_3$, 75 MHz) δ 10.92 (C-18), 18.51 (Si(CH)$_3$(CH$_3$)$_6$), 21.35 (—CCH$_2$CH$_3$), 24.40 (Si(CH)$_3$(CH$_3$)$_6$), 86.30 (t, J=23.2 Hz, (CF$_2$CC)), 111.96 (—CCH$_2$CH$_3$), 123.02 (C-4), 125.59 (C—Ar), 126.65 (C—Ar), 129.62 (C-10), 138.48 (C-9), 142.51 (—CCH$_2$CH$_3$), 143.64 (C—Ar), 144.89 (C—Ar), 156.37 (C-5), 199.37 (C-3).

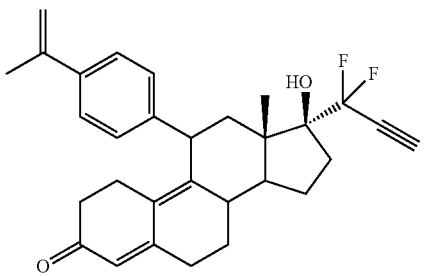

17α-(1,1-difluoro-2-propyn-1-yl)-17β-hydroxy-11β-[4-p-(1-methylethenyl) phenyl]estra-4,9-dien-3-one (EC358)

The reaction was done following the same procedure described for EC330 where 450 mg of compound 6e (0.72 mmol) was treated with 2.18 mL of a 1M solution of TBAF to get 190 mg of EC358 as a white powder, yield: 55%, mp 113-116° C. R$_f$: 0.64 (5:5, Hex:EtOAc). UV (nm): 204, 252, 300. FT IR (ATR, cm$^{-1}$): 3379, 3291, 2954, 2866, 2130, 1651, 1597.

$^1$H NMR (CDCl$_3$, 300 MHz) δ 0.62 (s, 3H, H-18), 2.9 (t, J=5.4 Hz, 1H, acetylenic hydrogen), 4.41 (d, J=7.2 Hz, 1H, H-11), 5.06 (s, 1H, —CCH$_2$CH$_3$), 5.37 (s, 1H, —CCH$_2$CH$_3$), 5.77 (s, 1H, H-4), 7.13 (d, J=8.1 Hz, 2H, H—Ar), 7.40 (d, J=8.4 Hz, 2H, H—Ar).

$^{13}$C NMR (CDCl$_3$, 75 MHz) δ 16.65 (C-18), 21.65 (—CCH$_2$CH$_3$), 85.83 (t, J=24 Hz, (CF$_2$CC)), 111.97 (—CCH$_2$CH$_3$), 123.09 (C-4), 125.6 (C—Ar), 126.65 (C—Ar), 129.7 (C-10), 138.45 (C-9), 142.49 (—CCH$_2$CH$_3$), 143.51 (C—Ar), 144.75 (C—Ar), 156.3 (C-5), 199.41 (C-3).

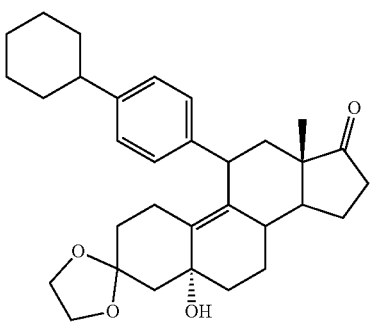

3,3-Ethylendioxy-5α-hidroxy-11β-[4-p-(cyclohexyl)phenyl]estra-9-en-17-one (3h)

Compound 3h was synthesized following the procedure described for compound 3a, where 3 g of compound 2 (9 mmol) was reacted with 875 g of Mg (36.4 mmol), 7 g of 4-bromocyclohexylbenzene (29.2 mmol) and 261 mg of CuCl (2.6 mmol) to afford 3 h as a white powder (3.46 g), yield: 80%, mp 112-113° C. Rf: 0.27 (5:5, Hex:EtOAc). UV (nm): 220. FT IR (ATR, cm$^{-1}$): 3507, 2920, 2859, 1732, 1442.

$^1$H NMR (CDCl$_3$, 300 MHz) δ 0.47 (s, 3H, H-18), 3.9 (m, 4H, ketal), 4.3 (d, J=6.9 Hz, 1H, H-11), 4.37 (s, 1H, —OH), 7.08 (d, J=8.4 Hz, 2H, H—Ar), 7.13 (d, J=8.1 Hz, 2H, H—Ar).

$^{13}$C NMR (CDCl$_3$, 75 MHz) δ 14.25 (C-18), 64.03 (ketal), 64.65 (ketal), 70.02 (C-5), 108.69 (C-3), 126.64 (C—Ar), 126.85 (C—Ar), 133.80 (C-10), 134.95 (C—Ar), 143.1 (C-9), 145.29 (C—Ar), 219.97 (C-17).

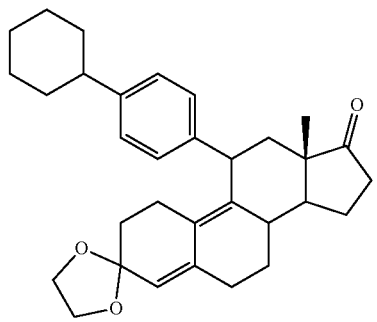

3,3-Ethylendioxy-11β-[4-p-(cyclohexyl)phenyl]estra-4,9-dien-17-one (4h)

The synthesis of compound 4h was done following the procedure described for the synthesis of compound 4a where 3.4 g of 3 h (6.9 mmol) was treated with 3.6 mL of acetic anhydride (34.6 mmol), 81.8 mg of DMAP (0.69 mmol) and 40 mL of pyridine, to get 2.5 g of 4 h as a white powder (78% yield), mp 110-112° C. RE 0.66 (5:5, Hex:EtOAc). UV (nm): 200, 220, 300. FT IR (ATR, cm$^{-1}$): 2913, 2846, 1732, 1503.

$^1$H NMR (CDCl$_3$, 300 MHz) δ 0.49 (s, 3H, H-18), 3.9 (m, 4H, ketal), 4.3 (d, J=6.9 Hz, 1H, H-11), 5.38 (s, 1H, H-4), 7.07 (d, J=8.4 Hz, 2H, H—Ar), 7.13 (d, J=8.4 Hz, 2H, H—Ar).

$^{13}$C NMR (CDCl$_3$, 75 MHz) δ 14.39 (C-18), 64.40 (ketal), 64.54 (ketal), 106.18 (C-3), 121.65 (C-4), 126.75 (C—Ar), 126.89 (C—Ar), 130.03 (C-10), 137.81 (C—Ar), 139.38 (C-5), 139.42 (C-9), 141.82 (C—Ar), 145.32 (C—Ar), 219.65 (C-17).

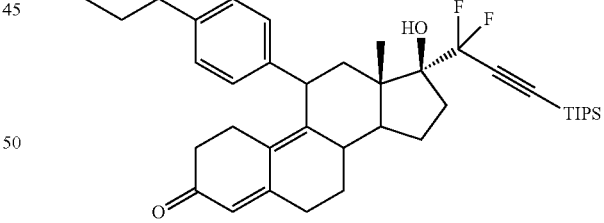

17α-[1,1-difluoro-3-[tris(1-methylethyl)silyl]-2-propyn-1-yl]-17β-hydroxy-11β-[4-p-(cyclohexyl) phenyl]estra-4,9-dien-3-one (6h)

This reaction was done following the same procedure described for the synthesis of compound 6a where 2.4 g of compound 4h (4.89 mmol) was reacted with 6.0 g of 3-bromo-3,3-difluoro-1-triisopropylsilylpropyne (19.5 mmol), and 9.78 mL of a 2M solution of n-BuLi (24.45 mmol). The crude product 5 h obtained was hydrolyzed with 3.6 mL (14.67 mmol) of a 4N solution of HCl to get 2.4 g of 6 h as a beige powder, yield: 75%, mp 99-102° C. R$_f$:0.64 (7:3, Hex:EtOAc). FT IR (ATR, cm$^{-1}$): 3406, 2920, 2859, 2184, 1651, 1597.

¹H NMR (CDCl₃, 300 MHz) δ 0.60 (s, 3H, H-18), 1.03 (s, 3H, Si(C$\underline{\text{H}}$)₃(CH₃)₆), 1.1 (s, 18H, Si(CH)₃(C$\underline{\text{H}}_3$)₆), 4.40 (d, J=4.5 Hz, 1H, H-11), 5.77 (s, 1H, H-4), 7.07 (d, J=8.7 Hz, 2H, H—Ar), 7.11 (d, J=8.4 Hz, 2H, H—Ar).

¹³C NMR (CDCl₃, 75 MHz) δ 10.82 (C-18), 18.35 (Si(CH)₃($\underline{\text{C}}$H₃)₆), 24.40 (Si($\underline{\text{C}}$H)₃(CH₃)₆), 86.34 (t, J=23.2 Hz, ($\underline{\text{C}}$F₂CC)), 122.88 (C-4), 126.58 (C—Ar), 126.88 (C—Ar), 129.43 (C-10), 141.43 (C-9), 145.38 (C—Ar), 145.51 (C—Ar), 156.55 (C-5), 199.48 (C-3).

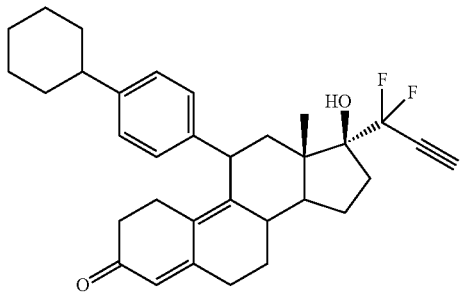

EC360

17α-(1,1-difluoro-2-propyn-1-yl)-17β-hydroxy-11β-[4-p-(cyclohexyl) phenyl]estra-4,9-dien-3-one (EC360)

The reaction was done following the same procedure as described for EC330 where 2.3 g of compound 6h (3.5 mmol) was treated with 5.22 mL of a 1M solution of TBAF to get 1.27 g of EC360 as a white powder, yield: 72%, mp 133-135° C. R$_f$: 0.77 (5:5, Hex:EtOAc). UV (nm): 200, 223, 301. FT IR (ATR, cm⁻¹): 3406, 3284, 2927, 2839, 2124, 1645, 1591.

⁻¹H NMR (CDCl₃, 300 MHz) δ 0.61 (s, 3H, H-18), 2.92 (t, J=5.4 Hz, 1H, acetylenic hydrogen), 4.42 (d, J=6.6 Hz, 1H, H-11), 5.77 (s, 1H, H-4), 7.09 (s, 4H, H—Ar).

¹³C NMR (CDCl₃, 75 MHz) δ 16.61 (C-18), 85.87 (t, J=24.9 Hz, ($\underline{\text{C}}$CF₂CC)), 122.97 (C-4), 126.60 (C—Ar), 126.90 (C—Ar), 129.53 (C-10), 141.36 (C-9), 145.24 (C—Ar), 145.56 (C—Ar), 156.49 (C-5), 199.55 (C-3).

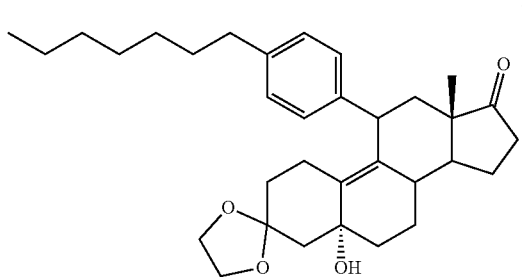

3i 3,3-Ethylendioxy-5α-hidroxy-11β-[4-p-(n-heptyl)phenyl]estra-9-en-17-one (3i)

Compound 3i was synthesized following the procedure described for compound 3a, where 4 g of compound 2 (12.10 mmol) was reacted with 1.76 g of Mg (72.6 mmol), 15.5 g of 4-bromo 4'-n-heptylbenzene (60.5 mmol) and 598 mg of CuCl (6.05 mmol) to afford 3i as a white amorphous solid (4.73 g), yield: 77%

¹H NMR (CDCl₃, 300 MHz) δ 0.48 (s, 3H, H-18), 0.85 (t, J=6 Hz, 3H, —CH₃), 1.27 (m, 10H, —CH₂), 2.54 (t, J=9 Hz, 3H, —CH₃), 3.98 (m, 4H, ketal), 4.29 (d, J=6 Hz, H-11), 4.3 (s, 1H, —OH), 7.05 (d, J=9 Hz, 2H, H—Ar), 7.11 (d, J=9 Hz, 2H, H—Ar).

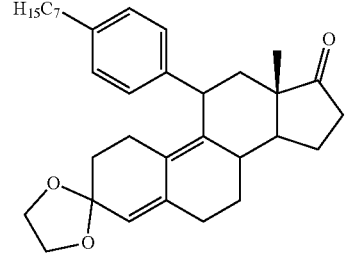

4i 3,3-Ethylendioxy-11β-[4-p-(n-heptyl)phenyl]estra-9-en-17-one (4i)

The synthesis of compound 4i was done following the procedure described for the synthesis of compound 4a where 4.5 g of 3i (8.89 mmol) was treated with 4.2 mL of acetic anhydride (44.4 mmol), 108.6 mg of DMAP (0.89 mmol) and 40 mL of pyridine, to get 1.76 g of 4i as an amorphous solid (41% yield)

¹H NMR (CDCl₃, 300 MHz) δ 0.5 (s, 3H, H-18), 0.87 (t, J=6 Hz, 3H, —CH₃), 1.27 (m, 10H, —CH₂), 3.95 (m, 4H, ketal), 4.3 (d, J=6 Hz, H-11), 5.39 (s, 1H, H-4), 7.06 (d, J=9 Hz, 2H, H—Ar), 7.11 (d, J=9 Hz, 2H, H—Ar).

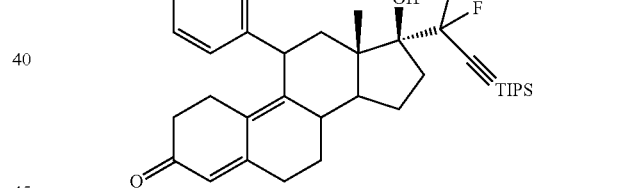

6i

17α-[1,1-difluoro-3-[tris(1-methylethyl)silyl]-2-propyn-1-yl]-17β-hydroxy-11β-[4-p-(n-heptyl) phenyl]estra-4,9-dien-3-one (6i)

This reaction was done following the same procedure described for the synthesis of compound 6a where 0.61 g of compound 4i (4.89 mmol) was reacted with 1.6 g of 3-bromo-3,3-difluoro-1-triisopropylsilylpropyne (4.9 mmol), and 2.6 mL of a 2M solution of n-BuLi (4.9 mmol). The crude product 51 obtained was hydrolyzed with 1.2 mL (4.8 mmol) of a 4N solution of HCl to get 0.52 g of 6i as an amorphous solid yield: 64%

¹H NMR (CDCl₃, 300 MHz) δ 0.6 (s, 3H, H-18), 0.87 (m, 3H, —CH₃), 1.1 (s, 18H, Si(CH)₃(CH₃)₆), 1.28 (m, 10H, —CH₂), 4.39 (m, 1H, H-11), 5.77 (s, 1H, H-4), 7.06 (d, J=9 Hz, 2H, H—Ar), 7.11 (d, J=9 Hz, 2H, H—Ar).

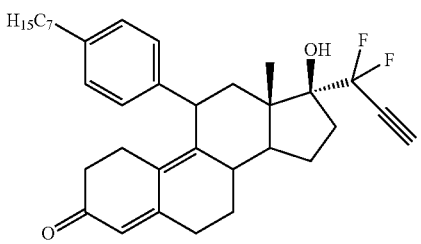

17α-(1,1-difluoro-2-propyn-1-yl)-17β-hydroxy-11β-[4-p-(n-heptyl)phenyl]estra-4,9-dien-3-one (EC362)

The reaction was done following the same procedure as described for EC330 where 513 mg of compound 6i (0.75 mmol) was treated with 1.52 mL of a 1M solution of TBAF to get 300 mg g of EC362 as a white powder, yield: 76%.

$^1$H NMR (CDCl$_3$, 300 MHz) δ 0.61 (s, 3H, H-18), 0.87 (m, 3H, —CH$_3$), 1.27 (m, 10H, —CH$_2$), 2.90 (t, J=6 Hz, 1H), 4.39 (d, J=6 Hz, 1H, H-11), 5.77 (s, 1H, H-4), 7.07 (m, 4H, H—Ar).

$^{13}$C NMR (CDCl$_3$, 75 MHz) δ 14.05, 16.50, 22.56, 24.25, 25.72, 27.60, 29.07, 29.11, 31.01, 31.28, 31.72, 38.58, 39.15, 40.26, 47.64, 51.14, 85.74 (t, J=25 Hz), 115.98 (t, J=241 Hz), 122.85, 126.56, 128.46, 129.42, 140.28, 141.25, 145.33, 156.60, 199.59

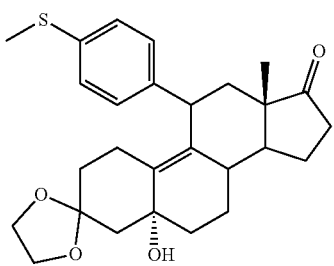

3,3-Ethylendioxy-5α-hidroxy-11β-[4-p-(methylthio)phenyl]estra-4,9-dien-17-one (3j)

Following the procedure described for compound 3a, 3 g of compound 2 (9.07 mmol) was reacted with 772 mg of Mg (31.77 mmol), 6.5 g of 4-bromo-thioanisole (31.7 mmol) and 454 mg of CuCl (4.5 mmol) to afford 3j as an amorphous solid (2.83 g), yield: 69%.

$^1$H NMR (CDCl$_3$, 300 MHz) δ 0.51 (s, 3H, H-18), 2.64 (s, 3H, —SCH$_3$), 3.97 (m, 4H, ketal), 4.28 (d, J=7 Hz, H-11), 4.38 (s, 1H, —OH), 7.14 (m, 4H, H—Ar).

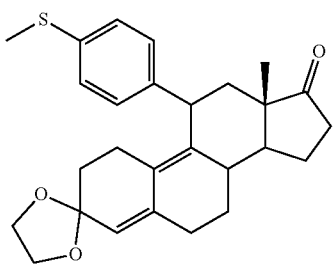

3,3-Ethylendioxy-5α-hidroxy-11β-[4-p-(methylthio)phenyl]estra-4,9-dien-17-one (4j)

The synthesis of compound 4j was done following the procedure described for compound 4a where 2.83 g of 3j (6.22 mmol) was heated at 70° C. with 2.93 mL of acetic anhydride (31.11 mmol), 380 mg of DMAP (3.11 mmol) and 30 mL of pyridine, to get 2.01 g of 4j as an off white amorphous solid. (75% yield)

$^1$H NMR (CDCl$_3$, 300 MHz) δ 0.52 (s, 3H, H-18), 2.64 (s, 3H, —SCH$_3$), 3.97 (m, 4H, ketal), 4.28 (d, J=7 Hz, H-11), 5.4 (s, 1H, H-4), 7.14 (m, 4H, H—Ar).

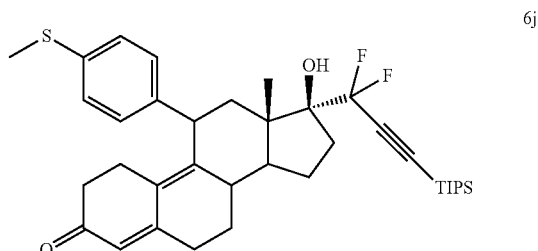

17α-[1,1-difluoro-3-[tris(1-methylethyl)silyl]-2-propyn-1-yl]-17β-hydroxy-11β-[4-p-(methylthio) phenyl]estra-4,9-dien-3-one (6j)

Following the same procedure described for 6a, 2 g of compound 4j (4.58 mmol) was reacted with 3.56 g of 3-bromo-3,3-difluoro-1-triisopropylsilylpropyne (11.4 mmol), and 5.8 mL of a 2M solution of n-BuLi (11.9 mmol). The crude 5j obtained was hydrolyzed with 4.6 mL (18.3 mmol) of a 4N solution of HCl to get 1.68 g of 6j as an amorphous solid, yield: 58%.

$^1$H NMR (CDCl$_3$, 300 MHz) δ 0.61 (s, 3H, H-18), 1.03 (m, 3H, Si(CH)$_3$(CH$_3$)$_6$), 1.11 (s, 18H, Si(CH)$_3$(CH$_3$)$_6$), 2.46 (s, 3H, —SCH$_3$), 4.37 (m, 1H, H-11), 5.77 (s, 1H, H-4), 7.08 (d, J=9 Hz, 2H, H—Ar), 7.16 (d, J=9 Hz, 2H, H—Ar).

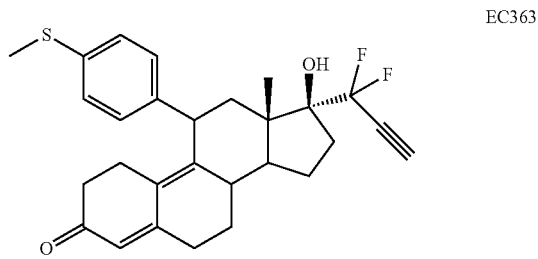 [SMILES: C#CC(F)(F)[C@]1(O)CCC2C3CCC4=CC(=O)CCC4=C3C(c3ccc(SC)cc3)C[C@@]21C]

17α-(1,1-difluoro-2-propyn-1-yl)-17β-hydroxy-11β-[4-p-(methylthio) phenyl]estra-4,9-dien-3-one (EC363)

The reaction was done following the same procedure reported for EC330 where 1.68 g of compound 6j (2.62 mmol) was treated with 5.2 mL of a 1M solution of TBAF to get 530 mg of EC356 as a beige powder, yield: 60%

$^1$H NMR (CDCl$_3$, 300 MHz) δ 0.61 (s, 3H, H-18), 2.45 (s, 3H, —SCH$_3$), 2.91 (t, J=5.4 Hz, 1H, acetylenic hydrogen), 4.39 (d, J=7.2 Hz, 1H, H-11), 5.77 (s, 1H, H-4), 7.11 (d, J=9 Hz, 2H, H—Ar), 7.16 (d, J=9 Hz, 2H, H—Ar).

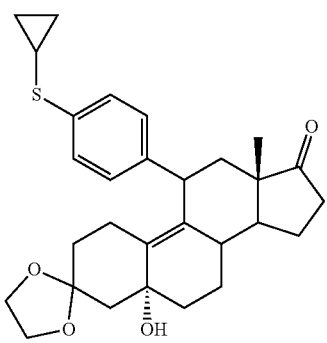

31

3,3-Ethylendioxy-5α-hidroxy-11β-[4-p-(cyclopropylthio)phenyl]estra-9-en-17-one (3l)

A three neck dried flask was charged with Mg turnings (350 mg, 14.52 mmol), a crystal of 12 was added and swirled over the Mg and kept for 5 min. 5 mL of anhydrous THF was added followed by 0.5 mL of 1,2-dibromoethane. The reaction was slightly warmed with a heat gun. When Mg starts reacting, a solution of the 4-bromophenyl-cyclopropyl sulfide (2.5 g, 10.9 mmol) in 10 mL of THF was added drop by drop, the 12 color gets discharged during the addition, after the addition was over, the reaction was stirred for 15 min and then refluxed at 60° C. (oil bath temperature) for 30 min. Afterward, the reaction was cooled to room temperature and CuCl (107.8 mg, 1.1 mmol) was added. The reaction was stirred for 6 hrs and then a solution of the epoxide 2 (1.2 g, 3.63 mmol) in THF (15 mL) was added dropwise and stirred for 1 h. The TLC showed a more polar product. The reaction was cooled and quenched by the addition of sat solution of NH$_4$Cl and extracted with ethyl acetate, the organic layer was washed with water and brine, the solvent was removed under vacuum. The crude was purified by column chromatography using 40% of ethyl acetate in hexane to get 0.85 g of white foam (44% yield), mp 93-95° C. UV (nm): 200, 257. Rr. 0.35 (5:5, Hex:EtOAc). FT IR (ATR, cm$^{-1}$): 3514, 2927, 2873, 1739, 1489. $^1$H NMR (CDCl$_3$, 300 MHz) δ 0.50 (s, 3H, H-18), 0.67 (m, 2H, cyclopropyl), 3.9 (m, 4H, ketal), 4.29 (d, J=6.9 Hz, 1H, H-11), 4.37 (s, 1H, —OH), 7.15 (d, J=8.4 Hz, 2H, H—Ar), 7.26 (d, J=10.2 Hz, 2H, H—Ar). $^{13}$C NMR (CDCl$_3$, 75 MHz) δ 8.45 (cyclopropyl), 12.04 (cyclopropyl), 14.32 (C-18), 64.05 (ketal), 64.67 (ketal), 69.97 (C-5), 108.59 (C-3), 126.47 (C—Ar), 127.53 (C—Ar), 133.37 (C-10), 135.32 (C—Ar), 135.58 (C-9), 143.05 (C—Ar), 219.82 (C-17).

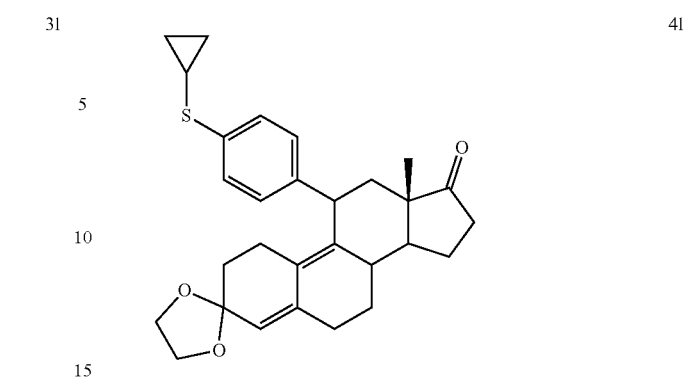

41

3,3-Ethylendioxy-11β-[4-p-(cyclopropylthio)phenyl]estra-4,9-dien-17-one (41)

The synthesis of compound 41 was done following the procedure described for the synthesis of compound 4a where 1.7 g of 31 (3.4 mmol) was reacted with 1.8 mL of acetic anhydride (17 mmol), 41 mg of DMAP (0.34 mmol) and 20 mL of pyridine, to get 1.22 g of 41 as a white powder (78% yield), mp 88-90° C. RE 0.55 (5:5, Hex:EtOAc). UV (nm): 200, 256. FT IR (ATR, cm$^{-1}$): 2933, 2873, 1739, 1638, 1489.
$^1$H NMR (CDCl$_3$, 300 MHz) δ 0.013 (s, 3H, H-18), 0.53 (m, 2H, cyclopropyl), 0.68 (m, 2H, cyclopropyl), 3.9 (m, 4H, ketal), 4.3 (d, J=6.9 Hz, H-11), 5.41 (s, 1H, H-4), 7.16 (d, J=8.4 Hz, 2H, H—Ar), 7.27 (d, J=9.3 Hz, 2H, H—Ar).
$^{13}$C NMR (CDCl$_3$, 75 MHz) δ 8.45 (cyclopropyl), 12.07 (cyclopropyl), 14.46 (C-18), 64.42 (ketal), 64.57 (ketal), 106.09 (C-3), 121.98 (C-4), 126.18 (C—Ar), 126.65 (C—Ar), 127.59 (C—Ar), 130.34 (C-10), 135.61 (C—Ar), 137.30 (C-5), 139.23 (C-9), 141.77 (C—Ar), 219.6 (C-17).

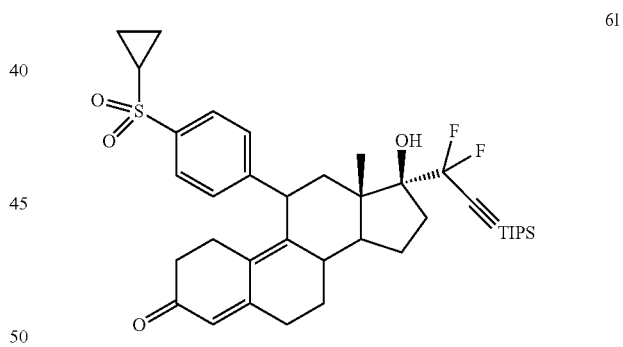

61

17α-[1,1-difluoro-3-[tris(1-methylethyl)silyl]-2-propyn-1-yl]-17β-hydroxy-11β-[4-p-(cyclopropyl sulfonyl)phenyl]estra-4,9-dien-3-one (61)

This reaction was done following the same procedure described for the synthesis of compound 6a where 1.2 g of compound 41 (2.6 mmol) was reacted with 3.2 g of 3-bromo-3,3-difluoro-1-triisopropylsilylpropyne (10.4 mmol), and 6.5 mL of a 2M solution of n-BuLi (13 mmol). The crude was used for the next step oxidation using Oxone. The crude was dissolved in a mixture of 50 mL of THF and 50 mL of methanol. A solution of 6.4 g of Oxone (20.8 mmol) in 30 mL of water was slowly added dropwise at 0° C. and was stirred for 3.5 hrs at 0° C. The TLC showed a more polar product. The reaction was quenched by adding water and extracted with ethyl acetate, the organic layer was washed with water and brine, the solvent was removed under vacuum. The crude was purified by column chromatography using 50% ethyl acetate in hexane to get 700 mg of a beige product (45% yield), mp 123-125° C. R$_f$:0.5 (7:3, Hex: EtOAc). UV (nm): 200, 230, 297. FT IR (ATR, cm$^{-1}$): 3466, 2933, 2879, 1726, 1631, 1483.

$^1$H NMR (CDCl$_3$, 300 MHz) δ 0.56 (s, 3H, H-18), 1.02 (s, 3H, Si(CH)$_3$(CH$_3$)$_6$), 1.1 (s, 18H, Si(CH)$_3$(CH$_3$)$_6$), 4.40 (d, J=5.4 Hz, 1H, H-11), 5.80 (s, 1H, H-4), 7.38 (d, J=8.4 Hz, 2H, H—Ar), 7.8 (d, J=8.4 Hz, 2H, H—Ar).

$^{13}$C NMR (CDCl$_3$, 75 MHz) δ 5.96 (cyclopropyl), 10.91 (C-18), 18.51 (Si(CH)$_3$(CH$_3$)$_6$), 24.40 (Si(CH)$_3$(CH$_3$)$_6$), 86.18 (t, J=24.3 Hz, (CF$_2$CC)), 123.57 (C-4), 127.73 (C—Ar), 127.93 (C—Ar), 130.36 (C-10), 138.31 (C-9), 143.21 (C—Ar), 151.0 (C—Ar), 155.76 (C-5), 198.93 (C-3).

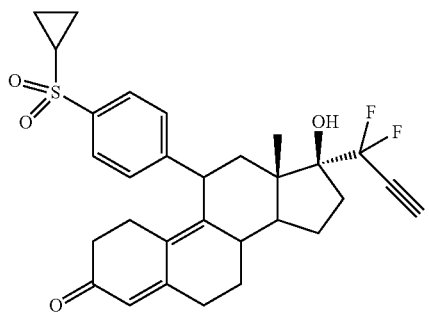

EC361

17α-(1,1-difluoro-2-propyn-1-yl)-17β-hydroxy-11β-[4-p-(cyclopropylsulfonyl) phenyl]estra-4,9-dien-3-one (EC361)

Following the same procedure reported for EC330, 700 mg of compound 61 (1.03 mmol) was treated with 1.53 mL of a 1M solution of TBAF to get 320 mg of EC361 as a white powder, yield: 59%, mp 145-148° C. R$_f$:0.23 (5:5, Hex: EtOAc). UV (nm): 200, 203, 301. FT IR (ATR, cm$^{-1}$): 3453, 3244, 2933, 2873, 2124, 1732, 1645. $^{-1}$H NMR (CDCl$_3$, 300 MHz) δ 0.54 (s, 3H, H-18), 2.92 (t, J=5.4 Hz, 1H, acetylenic hydrogen), 4.51 (d, J=6 Hz, 1H, H-11), 5.80 (s, 1H, H-4), 7.40 (d, J=8.4 Hz, 2H, H—Ar), 7.82 (d, J=8.7 Hz, 2H, H—Ar). $^{13}$C NMR (CDCl$_3$, 75 MHz) δ 5.99 (cyclopropyl), 14.16 (C-18), 85.71 (t, J=24.9 Hz, (CF$_2$CC)), 123.60 (C-4), 127.78 (C—Ar), 127.94 (C—Ar), 130.41 (C-10), 138.27 (C-9), 143.18 (C—Ar), 150.93 (C—Ar), 155.82 (C-5), 199.08 (C-3).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A cytotoxic compound having the structure (III):

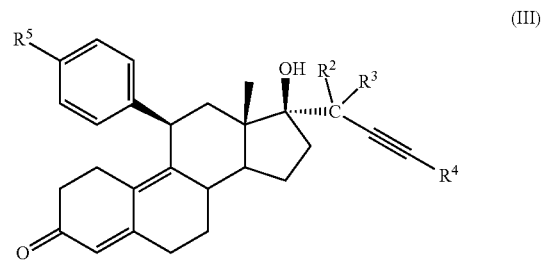

where:
R$^2$ and R$^3$ is F;
R$^4$ is H, alkyl, —CH$_2$—OH, —CO$_2$R$^6$, —CON(R$^6$)$_2$;
R$^5$ is a heterocycle; and
R$^6$ is H, alkyl, or cycloalkyl.

2. The cytotoxic compound of claim 1, wherein the cytotoxic compound has the structure (IV):

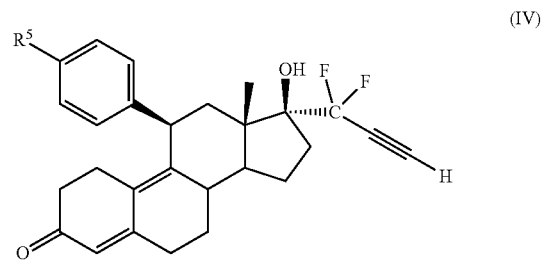

where R$^5$ is a heterocycle.

3. The compound of claim 1, wherein the cytotoxic compound has the structure (IV):

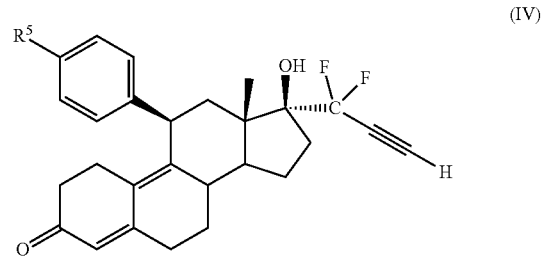

where R$^5$ is quinolinyl, isoquinolinyl, indolyl, 1,3-imidazolyl, dibenzofuranyl, and furanyl.

4. The cytotoxic compound of claim 1, wherein R$^5$ is quinolinyl.

5. The cytotoxic compound of claim 1, wherein R$^5$ is 1,3-imidazolyl.

6. The cytotoxic compound of claim 1, wherein R$^5$ is isoquinolinyl.

7. The cytotoxic compound of claim 1, wherein $R^5$ is indolyl.

8. The cytotoxic compound of claim 1, wherein $R^5$ is dibenzofuranyl.

9. The cytotoxic compound of claim 1, wherein $R^5$ is furanyl.

* * * * *